(12) United States Patent
Gallaher et al.

(10) Patent No.: US 7,452,968 B2
(45) Date of Patent: Nov. 18, 2008

(54) SECRETED PROTEIN FACTOR AND CELL MEMBRANE-BOUND SPLICE VARIANT

(75) Inventors: Timothy Kirk Gallaher, San Gabriel, CA (US); Lena A. Bealle, Tujanga, CA (US); Kai-Jin Wu, Los Angeles, CA (US); Yi Zhao, South Pasadena, CA (US); Unnati Jarlwata, Anaheim, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 10/541,086

(22) PCT Filed: Dec. 31, 2003

(86) PCT No.: PCT/US03/41742

§ 371 (c)(1),
(2), (4) Date: Mar. 11, 2007

(87) PCT Pub. No.: WO2004/060867

PCT Pub. Date: Jul. 22, 2004

(65) Prior Publication Data

US 2007/0160985 A1    Jul. 12, 2007

Related U.S. Application Data

(60) Provisional application No. 60/438,059, filed on Jan. 2, 2003.

(51) Int. Cl.
*C07K 14/435*    (2006.01)
*C07K 14/475*    (2006.01)
*C12P 21/02*    (2006.01)
*A61K 38/18*    (2006.01)

(52) U.S. Cl. .............................. 530/350; 514/2; 514/12; 536/23.5; 435/69.1

(58) Field of Classification Search ....................... None
See application file for complete search history.

(56) References Cited

U.S. PATENT DOCUMENTS

2003/0073129 A1* 4/2003 Baker et al. .................. 435/7.1

OTHER PUBLICATIONS

Wells, J.A. (1990). Additivity of mutational effects in proteins. Biochemistry. 29(37):8509-8517.*

Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

* cited by examiner

*Primary Examiner*—Christine J. Saoud
*Assistant Examiner*—Jon M Lockard
(74) *Attorney, Agent, or Firm*—Hogan & Hartson LLP

(57) ABSTRACT

A novel mammalian protein system is disclosed. This system comprises a secreted protein factor and its related membrane-bound splice variant. These novel proteins have no homology to any known protein or class or protein, yet are ubiquitously expressed in nearly all tissue types. Also disclosed are novel nucleic acids that encode the novel polypeptides of the invention. The protein system was discovered in purified populations of murine hematopoieitc stem cells. The cDNAs of the invention were cloned from a marine hematopoietic lineage negative (Lin) library.

4 Claims, 8 Drawing Sheets

HSS1 Expression in 293T Cells

1. His Tag Ladder
2. Cell Lysate pTT (Vector alone)
3. Serum Free Sup. pTT
4. Serum Sup. pTT
5. Cell Lysate pTT HSF1
6. Serum Free Sup. pTT HSF1 (20 ul)
7. Serum Free Sup. pTT HSF1 (10 ul)
8. Serum Sup. pTT HSF1 (20ul)
9. Serum Sup. pTT HSF1 (10ul)

SECRETED PROTEIN FACTOR AND CELL MEMBRANE-BOUND SPLICE VARIANT

RELATED APPLICATIONS

The present invention is related to the provisional application filed on Jan. 2, 2003, U.S. Ser. No. 60/438,059, which is incorporated by reference in its entirety.

TECHNICAL FIELD

The present invention is directed to compositions and methods related to proteins that modulate the growth, differentiation, trafficking and physiology of mammalian cells, e.g., cells of the hematopoietic system and the neuronal system of mammals

BACKGROUND OF THE INVENTION

The mammalian hematopoietic system comprises a number of protein factors that modulate cellular growth and differentiation. Included in the class of protein factors that regulate growth/differentiation are cytokines and chemokines. Some of these hematopoietic protein factors have been characterized and have provided the basis for clinically important pharmaceutical agents. Examples of hematopoietic protein factors that have been developed as pharmaceutical agents are erythropoietin (EPO) and granulocyte-colony stimulating factor (G-CSF). Other hematopoietic protein factors have found important uses in the neuronal system, such as epidermal growth factor (EGF) and fibroblast growth factor (FGF). These protein factors are used to support growth of cultured neuronal stem cells and progenitor cells. Still a host of other hematopoietic protein factors have been characterized which enable basic research efforts and support new technologies in various fields of endeavor.

Still to date, many mammalian hematopoietic protein factors remain uncharacterized. Thus, there is an important need to characterize mammalian hematopoietic protein factors that remain uncharacterized.

SUMMARY OF THE INVENTION

The present invention discloses the existence of a previously unknown protein system that possesses structural and biochemical properties associated with a cytokine/chemokine-like motif. This previously unknown system of proteins has no structural homology to any known protein or protein class in the current protein database, yet is ubiquitously expressed in nearly all tissue types. Thus, the proteins of the inventions, encoded by the nucleic acids of the invention, represent structurally unique ways to perform a biological function. The novel proteins disclosed herein reveal two related proteins, namely a secreted protein and its membrane-bound splice variant. These proteins are designated as HSS1 and HSM1, respectively.

Embodiments of the present invention provides for several compositions of matter. These compositions of matter include isolated polypeptides, nucleic acids, expression vectors, antibodies, apatmers and RNAis, as well as pharmaceutical compositions, which include one or more polypeptides of the invention as an active agent, and kits that include one or more of the compositions of matter disclosed herein. Other embodiments of the present invention include binding partners of the polypeptides disclosed. Still other embodiments of the present invention provide for several methods related to producing and using the previously undisclosed system of polypeptides and nucleic acids.

Polypeptide embodiments of the invention include isolated human and murine proteins that were first discovered in murine hematopoietic stem cells. Thus, mammalian polypeptides are disclosed to human HSS1 and HSM1, namely hHSS1 and hHSM1, and to murine HSS1 and HSM1, namely mHSS1 and mHSM1. The corresponding full immature protein sequences for these polypeptides are disclosed in SEQ ID NO: 1 (hHSS1), SEQ ED NO: 2 (hHSM1), SEQ ID NO: 3 (mHSS1) and SEQ ID NO: 4 (mHSM1). However, each of these sequences possesses a signal peptide sequence at the amino terminal end, which is not included in the full mature protein polypeptides of the invention. Examples of mature polypeptide embodiments of the present invention are disclosed in SEQ ID NOS: 21-30. Polypeptide embodiments of the invention further include variant polypeptides that are related to SEQ ID NOS: 1-4, SEQ ID NOS: 9-10, SEQ ID NOs: 13-14, SEQ ID NOS: 17-18 and SEQ ID NOS: 21-30, and retain substantially the same activity as these native proteins, but are altered in their respective amino acid sequences to yield variant human and murine HSS1 and HSM1 proteins having one or more amino acids that are replaced, deleted, inserted and/or added.

The polypeptide embodiments of the invention are encoded for by nucleic acid sequences that are also disclosed herein. Embodiments of nucleic sequences that encode for the proteins disclosed in SEQ ID NO: 1 (hHSS1), SEQ ID NO: 2 (hHSM1), SEQ ID NO: 3 (mHSS1) and SEQ ID NO: 4 (mHSM1) are disclosed in SEQ ID NO: 5 (hHSS1), SEQ ID NO: 6 (hHSM1), SEQ ID NO: 7 (mHSS1), SEQ ID NO: 8 (mHSM1), SEQ ID NO: 9 (hHSC1), SEQ ID NO: 10 (mHSC1), SEQ ID NO: 13 (hHSC2), SEQ ID NO: 14 (mHSC2), SEQ ID NO: 17 (hHSC3), SEQ ID NO: 18 (mHSC3), respectively. The present invention also discloses variant nucleic acid sequences that are related to SEQ ID NOS: 5-8, SEQ ID NOS: 11-12, 15-16, and 19-20, but are altered in their respective nucleic acid sequence to yield variant cDNA molecules having one or more codons that are replaced, deleted, inserted and/or added. These variant cDNA molecules, therefore, encode for the variant polypeptides of the invention.

Further embodiments of the polypeptides of the invention are disclosed which include human and murine core protein sequences that are related to SEQ ID NOS: 1-4 in that the core protein sequences are encompassed within these sequences. Some embodiments of the core protein sequences of the invention are disclosed in SEQ ID NO: 9 (hHSC1), SEQ ID NO: 13 (hHSC2) and SEQ ID NO: 17 (hHSC3) for the human core protein including a signal peptide, and SEQ ID NO: 10 (mHSC1), SEQ ID NO: 14 (mHSC2) and SEQ ID NO: 18 (mHSC3) for the murine core protein including a signal peptide. The core sequences depicted in SEQ ID NOS: 9-10 and SEQ ID NOS: 13-14 largely encompass exons 1-6 of the human and murine proteins of the invention and include a signal peptide sequence. The polypeptide embodiments of the invention represented by the mammalian core protein sequences further include variant polypeptides corresponding to SEQ ID NO: 9, SEQ ID NO: 10, SEQ ID NO: 13, SEQ ID NO: 14, SEQ ID NO: 17 and SEQ ID NO: 18 that retain substantially the same activity as the native core proteins, but are altered in their respective amino acid sequences to yield variant HSC1 human and murine proteins having one or more amino acids that are replaced, deleted, inserted and/or added. Examples of polypeptides of the invention without a signal peptide, i.e., mature polypeptides, are also disclosed in SEQ ID NOS: 21-30.

The core polypeptide embodiments of the invention are encoded for by nucleic acid sequences that are also disclosed herein. Embodiments of nucleic sequences that encode for the core mammalian proteins disclosed in SEQ ID NO: 9, SEQ ID NO: 10, SEQ ID NO: 13, SEQ ID NO: 14, SEQ ID NO: 17 and SEQ ID NO: 18, are disclosed in SEQ ID NO: 11, SEQ ID NO: 12, SEQ ID NO: 15, SEQ ID NO: 16, SEQ ID NO: 19 and SEQ ID NO: 20, respectively. The present invention also discloses variant nucleic acid sequences that are related to SEQ ID NOS: 11-12, 15-16 and 19-20, but are altered in their respective nucleic acid sequence to yield variant cDNA molecules having one or more codons that are replaced, deleted, inserted and/or added. These variant cDNA molecules, therefore, encode for the variant core polypeptides of the invention.

Other embodiments of the present invention include pharmaceutical compositions in which one or more of the polypeptides disclosed herein are included as an active agent, or ingredient, of the composition. Embodiments of the pharmaceutical compositions of the invention include at least one of the following polypeptides as an active agent: the polypeptide of SEQ ID NO: 21, SEQ ID NO: 22, SEQ ID NO: 23, SEQ ID NO: 24. SEQ ID NO: 25, SEQ ID NO: 26, SEQ ID NO: 27, SEQ ID NO: 28, SEQ ID NO: 29 or SEQ ID NO: 30. Still other embodiments of the pharmaceutical compositions of the invention include one or more variant polypeptides, disclosed herein, as an active agent. These variant polypeptides included as active agents in the pharmaceutical compositions of the invention are related to SEQ ID NO: 21, SEQ ID NO: 22, SEQ ID NO: 23, SEQ ID NO: 24. SEQ ID NO: 25, SEQ ID NO: 26, SEQ ID NO: 27, SEQ ID NO: 28, SEQ ID NO: 29 or SEQ ID NO: 30, and retain substantially the same activity as the native proteins, but are altered in their respective protein sequence to yield variant protein agents having one or more amino acids that are replaced, deleted, inserted and/or added.

Still other embodiments of the invention are provided. These embodiments include protein expression vectors that comprise a nucleic acid, disclosed herein, which expresses a polypeptide of the invention. These embodiments refer to transformants, carrying, in an expressible manner, one or more nucleic acids of the present invention.

Further embodiments of the invention include one or more isolated antibodies comprising an antigenic polypeptide that binds to a specific portion of a sequence disclosed in SEQ ID NOS: 14, 9-10, 13-14, 17-18 and variant polypeptides of these sequences as disclosed herein. Other embodiments of the invention include interfering nucleic acid molecules that can be used to "knock out" the expression of the polypeptides of the invention. These molecules are RNA molecules that bind to the related mRNA corresponding to the nucleic acids sequences disclosed herein. These molecules are referred to in the art as RNAi molecules. Still further embodiments of the invention include one or more isolated nucleic acid molecules that specifically bind to a portion of one or more polypeptides of the invention. These nucleic acid molecules are referred to as specific aptamers to embodiments of the polypeptides of the invention. Methods of producing aptamer embodiments of the present invention are known in the art.

Kit embodiments are also provided in the present invention including one or more polypeptides, nucleic acids, vectors and/or antibodies disclosed herein, along with instructional material for the use of the composition and/or segregation of the composition into a container.

Another embodiment of the invention includes binding partners for the various embodiments of the polypeptide and the nucleic acids of the invention. According to the invention, a binding target is a molecule, preferably a protein or nucleic acid, that binds to a polypeptide or nucleic acid of the invention, including variant polypeptides and nucleic acids of the invention, with a binding affinity of about $10^{-8}$ M or greater for the protein embodiments and a binding affinity of about $10^{-8}$ M or greater for the nucleic acid embodiments. Antibody and aptamer embodiments of the invention are included as examples of binding partners of the polypeptides of the invention.

Several methods embodiments of the present invention are also provided. These methods include methods of producing the polypeptides disclosed herein. These methods are accomplished by culturing transformed cells comprising a vector of the invention that carries one or more nucleic acids disclosed herein and isolating the polypeptide.

Other method embodiments of the invention include methods of screening for a compound that binds to a polypeptide of the invention. These methods include contacting one or more test compounds with a polypeptide of invention, determining whether a test compound binds to the polypeptide and selecting the test compound that binds to a polypeptide of the invention.

Still other method embodiments of the invention include methods of screening a polypeptide of the invention for its binding activity to one or more cell types. These methods include contacting a polypeptide of the invention with one or more cell types and determining whether the polypeptide binds to one or more cell types. Particular embodiments of these methods include hematopoietic cells or neuronal cells as the cell target. Also included are stem cells and progenitor cell types.

Further method embodiments of the present invention include methods of modulating the physiology of a cell type with a polypeptide or nucleic acid of the invention. These methods include contacting the cell type with a polypeptide or nucleic acid of the invention and monitoring the cell type for a change in physiology of the cell type.

Further embodiments of the present invention include the polypeptides disclosed herein that are modified. Modified polypeptides of the invention include proteolyzed proteins, glycoproteins, acylated proteins, methylated proteins, phosphyorylated proteins, sulfated proteins, prenylated proteins and other known modifications, including various types of lipid-modified proteins.

DETAILED DESCRIPTION

I. General

Figure 1:
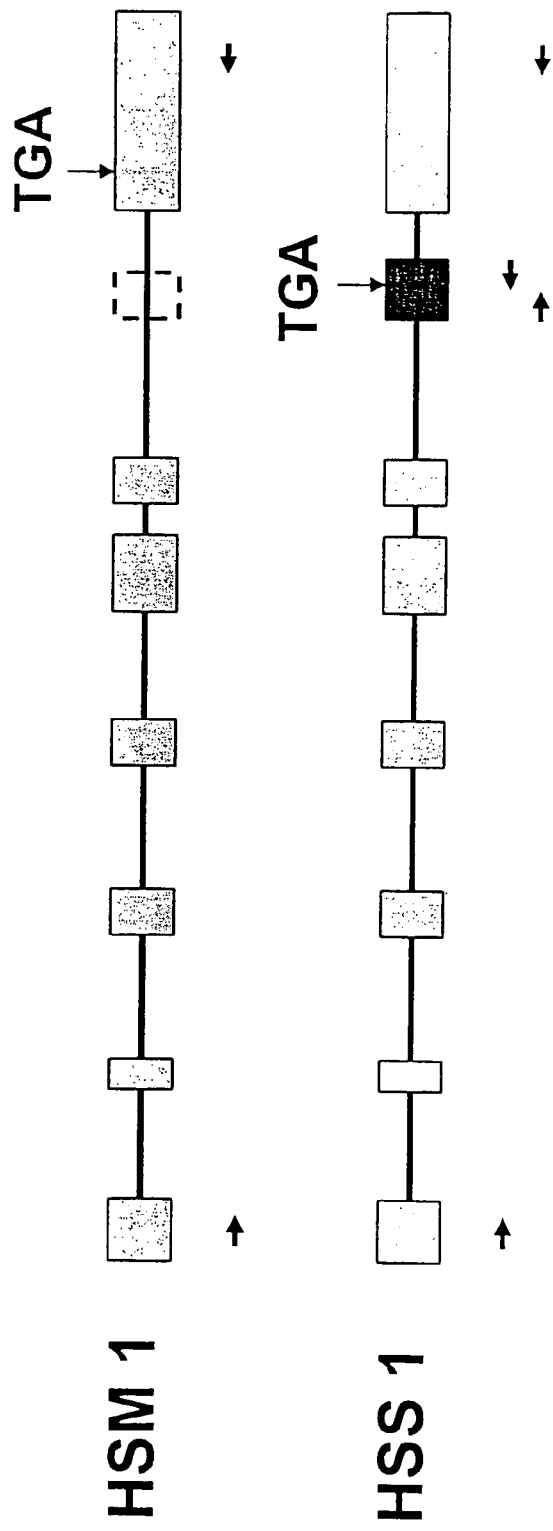
FIG. 1 illustrates the gene structures for human HSS1 and HSM1; the human proteins of the invention were cloned by PCR from human testis cDNA; the genomic location for human HSS1 and HSM1 is at chromosome 19, at locus 19q13.33.

The present invention discloses the existence of a previously unknown class of proteins that possess structural and biochemical properties associated with a cytokine/chemokine-like motif, but may include other biologically functional motifs as well. This previously unknown class of proteins has no structural homology to any known protein or protein class in the current protein database, yet is ubiquitously expressed in nearly all tissue types. Thus, the proteins of the invention, as encoded for by the nucleic acids molecules of the invention, represent structurally unique ways to perform a biological function. Suggestive of a cytokine-like motif is the fact that the cDNAs corresponding to polypeptides of the invention have a 3' non-coding region that includes several mRNA destabilizing sequences (Lagnando C A, Brown C Y, Goodall G J (1994) Mol. Cell. Biol. 14, 7984-7995) called ARE (AT Rich element), often seen in cytokine mRNAs. Table 1 shows the complete amino acid sequences for human HSM1, comprising 262 amino acids, and human HSS1, comprising 254 amino acids. Each amino acid sequence corresponds to the translation of 7 exons, six of which are identical. The portions of these two proteins which are different are underlined and are found in the 7$^{th}$ exon of the corresponding gene products. Approximately the first 27 amino acids of both proteins represent the signal peptide, which is cleaved in the mature proteins. Most notable is a polyglycine stretch at the carboxyl terminal end of HSM1, which is predicted to be located at the intracellular membrane and may play a role in intracellular signaling.

TABLE 1

SEQ ID No. 3: Human HSM 1, 262 aa

MAAASAGATRLLLLLLMAVAAPSRARGSGCRAGTGARGAGAEGREGEACG
TVGLLLEHSFEIDDSANFRKRGSLLWNQQDGTLSLSQRQLSEEERGRLRD
VAALNGLYRVRIPRRPGALDGLEAGGYVSSFVPACSLVESHLSDQLTLHV
DVAGNVVGVSVVTHPGGCRGHEVEDVDLELFNTSVQLQPPTTAPGPETAA
FIERLEMEQAQKAKNPQEQKSFFAKYWMYIIPVVLFLMMSGAPDAGGQGG
GGGGGGGGSGR

SEQ ID No. 1: Human HSS 1, 254 aa

MAAASAGATRLLLLLLMAVAAPSRARGSGCRAGTGARGAGAEGREGEACG
TVGLLLEHSFEIDDSANFRKRGSLLWNQQDGTLSLSQRQLSEEERGRLRD
VAALNGLYRVRIPRRPGALDGLEAGGYVSSFVPACSLVESHLSDQLTLHV
DVAGNVVGVSVVTHPGGCRGHEVEDVDLELFNTSVQLQPPTTAPGPETAA
FIERLEMEQAQKAKNPQEQKSFFAKYWHIILGGAVLLTALRPAAPGPAPP
PQEA

The novel proteins disclosed herein reveal two related proteins, namely a secreted protein and its related membrane-bound splice variant. These proteins are designated as HSS1 and HSM1, respectively. The invention further discloses several mammalian forms of these proteins, namely the human and murine forms of HSS1 and HSM1. Thus, the present invention provides mammalian protein sequences, as well as nucleic acid sequences encoding the disclosed mammalian proteins, which exhibit structural properties or motifs characteristic of a cytokine or chemokine. Table 2 shows a listing of exemplary forms of protein and nucleic embodiments of the invention with nomenclature used herein. The descriptions below are directed, for exemplary purposes, to primate and rodent embodiments, e.g., human and mouse, but are likewise applicable to related embodiments from other, e.g., natural, sources. These sources include various vertebrates, typically warm blooded animals, e.g., birds and mammals, particularly domestic animals, and primates.

TABLE 2

Full length coding for human and mouse HSS1 and HSM1

1. hHSS1 P 254 aa
2. mHSS1 P 254 aa
3. hHSM1 P 262 aa
4. mHSM1 P 258 aa
5. hHSS1 N 1962 nt
6. mHSS1 N 988 nt
7. hHSM1 N 1875 nt
8. mHSM1 N 1540 nt

Core sequence, full length, i.e. includes signal peptide - three core proteins and corresponding nucleic acids 9. hHSC1 P 227 aa
10. mHSC1 P 227 aa
11. hHSC1 N
12. mHSC1 N
13. hHSC2 P 225 aa
14. mHSC2 P 225 aa
15. hHSC2 N
16. mHSC2 N
17. hHSC3 P 221 aa
18. mHSC3 P 221 aa
19. hHSC3 N
20. mHSC3 N Mature proteins i.e. no signal peptide for HSS1, HSM1 and three core proteins 21. mhHSS1 P 227 aa
22. mmHSS1 P 227 aa
23. mhHSM1 P 235 aa
24. mmHSM1 P 231 aa
25. mhHSC1 P 200 aa
26. mmHSC1 P 200 aa
27. mhHSC2 P 198 aa
28. mmHSC2 P 198 aa
29. mhHSC3 P 194 aa
30. mmHSC3 P 194 aa

* P = protein; N = nucleic acid

"HSS" and "HSM" are shorthand references to some of the features of the polypeptides of the invention. The polypeptides of the invention are referred to as hHSS1 and hHSM1 for the human proteins and mHSS1 and mHSM1 for the murine proteins. The secreted forms of the polypeptides of the invention are designated as "HSS", and this designation refers to the fact these proteins were discovered in hematopoietic stem cells, possess a signal sequence and are secreted from the cell. The cell membrane-bound splice variant polypeptides of the invention are designated "HSM", and this designation refers to the fact that these proteins were found in hematopoietic stem cells, possess a signal sequence and a membrane-binding region, i.e., a transmembrane domain. Embodiments of the present invention also include the corresponding cDNAs encoding these proteins.

Figure 2:
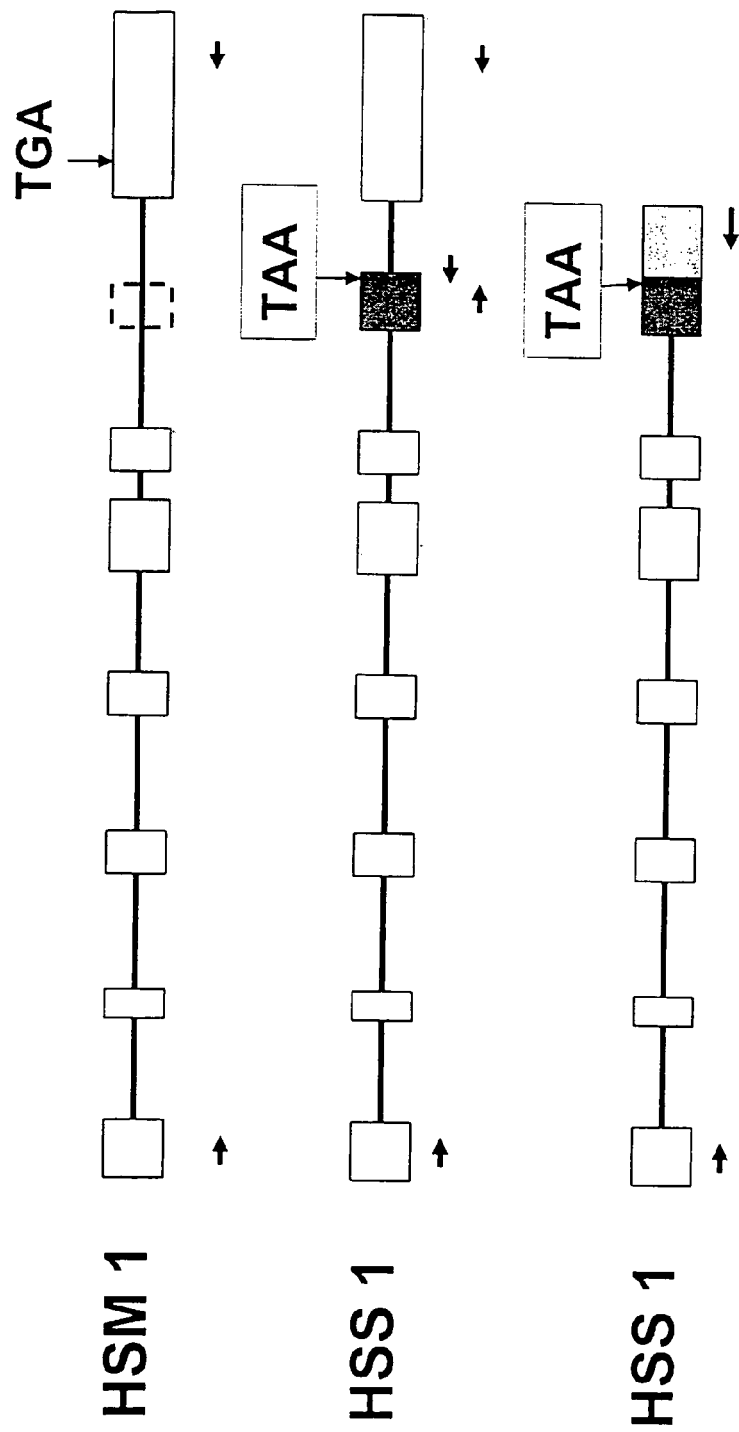
FIG. 2 illustrates the gene structures for murine HSS1 and HSM1; the murine proteins of the invention were cloned by PCR from murine bone marrow Lin⁻ cDNA library; the genomic location for murine HSS1 and HSM1 is at chromosome 7.

FIG. 1 and FIG. 2 show the exon arrangement of the genes associated with the secreted forms and membrane-bound forms of the polypeptides of the invention. As depicted in the figures, various embodiments of the secreted form and membrane-bound form of the invention are related to each other in that these forms include the same first six exons, but differ from each other in the their respective $7^{th}$ exon. The $7^{th}$ exon of the secreted forms of the polypeptides of the invention does not form a transmembrane domain, but since these polypeptides possess a signal peptide sequence, they are largely secreted from the cell after they are expressed. See FIG. 3 and FIG. 4.

On the other hand, the $7^{th}$ exon of the transmembrane forms of the polypeptides of invention possess a predicted transmembrane domain at the carboxyl terminal region. The transmembrane domain of the HSM1 polypeptide forms of the invention function to anchor the protein to the cell membrane. Thus, these two protein forms of the invention form a system with one form being secreted from the cell and the other form being bound to the cell membrane. However, the membrane-bound form may be cleaved to yield a soluble various soluble forms of the polypeptides of the invention.

Figure 5:
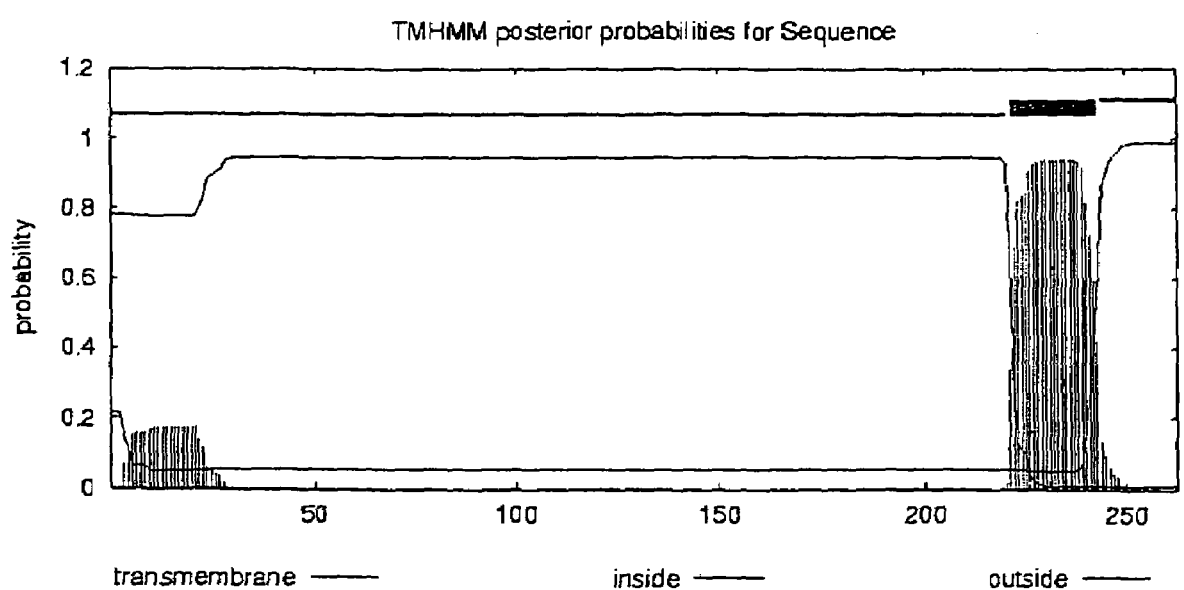
FIG. 5 depicts the results of the analysis of human HSM1 which indicates that HSM1 includes a transmembrane domain located at the carboxyl-terminal end of the polypeptide; the probability of forming a transmembrane domain is approximately 1.0; shaded areas in the figure represent hydrophobic regions of HSM1.
Figure 6:
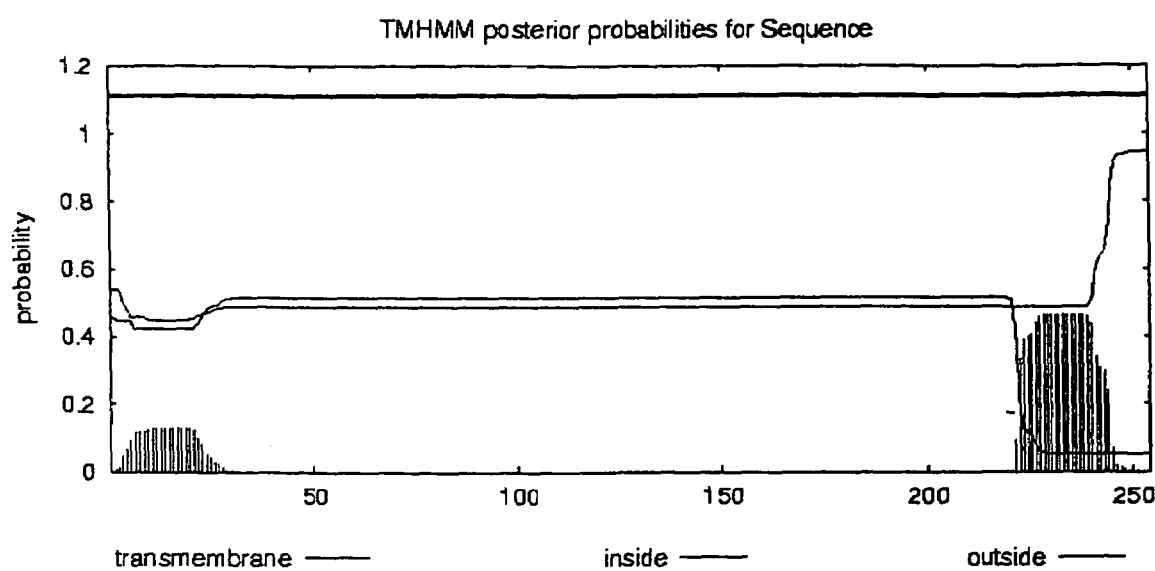
FIG. 6 depicts the results of the analysis of human HSS1 which indicates that HSS1 does not possess a transmembrane domain; the probability of forming a transmembrane domain is approximately 0.4; shaded areas in the figure represent hydrophobic regions of HSM1.

The transmembrane domains found in hHSM1 and mHSM1 are predicted using the hidden Markov model (TM-HMM) algorithm, which predicts the presence of a transmembrane domain sequence at, or near, the C-terminal end of these proteins. FIG. 5 and FIG. 6 reveal the graphic representation of the predictive algorithm for hHSM1 (FIG. 5) as compared with hHSS1 (FIG. 6). As seen from the comparison of FIGS. 7 and 8, hHSM1 is predicted to include one transmembrane domain at its C-terminal end, whereas the presence of a transmembrane domain is not predicted for hHSS1. Additionally, these analyses predict the presence of one transmembrane domain at the C-terminal end of mHSM1 (data not shown). Thus, the splice variants of hHSS1 and mHSS1 are predicted to be membrane-bound proteins located on cell surfaces.

The simultaneous existence of a secreted protein form and a corresponding cell membrane-bound protein form of the polypeptides of the invention, which are produced from differential splicing of the immature RNA product of a gene, is a biologically relevant functional motif that has been reported in other systems that have important growth and regulatory functions in vivo. These systems include stem cell factor (SCF), a hematopoietic growth modulator/regulator, Delta-1, a hematopoietic stem cell expansion factor, and Flt3 ligand, another hematopoietic growth modulator/regulator. In the case of Flt3 ligand, three protein forms of the growth factor are actually observed. These Flt3 splice variants include an obligatory secreted protein form, a secreted form that is first expressed at the cell surface as a membrane-bound form, and a true membrane-bound form. For Flt3 ligand, the predominant form is the transmembrane form, which is biologically active. The transmembrane form of Flt3 ligand is cleaved in vivo to form a soluble form, which is also biologically active. The splice variant protein forms observed for Flt3 ligand also may be observed for the protein embodiments of the present invention.

Figure 3:
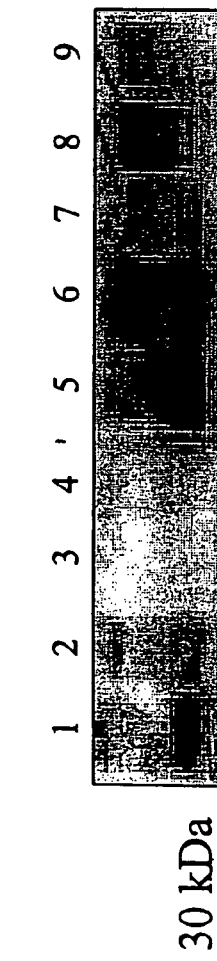
FIG. 3 depicts the result of a western blot analysis that reveals the expression of murine HSS1 in 293T cells; the analysis also reveals that HSS1 is found to be secreted into the supernatant following precipitation of the 293T cells.
Figure 4:
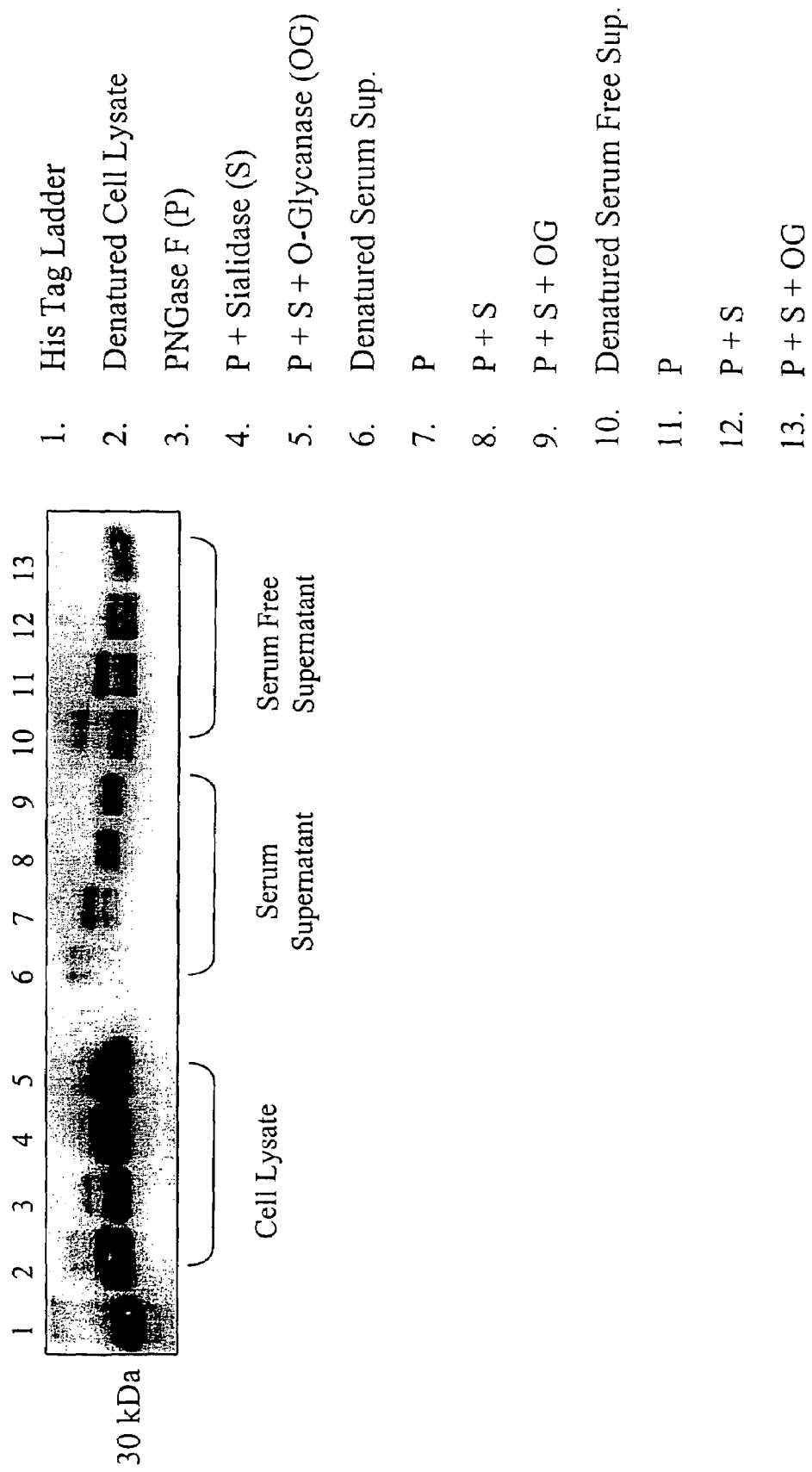
FIG. 4 depicts the result of a western blot analysis that reveals that murine HSS1 is a secreted and multi-glycosylated polypeptide.

The polypeptide forms disclosed herein for human and murine HSS1 and HSM1 were predicted to be secreted and membrane-bound forms, respectively, based on predictive algorithms. The fact that murine HSS1 is actually secreted in vivo was subsequently proven, as shown in FIG. 3 and FIG. 4. Both the secreted and membrane-bound forms of the polypeptides of the invention may be produced at the membrane surface and subsequently released, either over a period of time, or cleaved enzymatically, to yield secreted forms of HSS1 and HSM1. In the biological scenario where the protein is released over a period of time, HSS1 should be released from the membrane more quickly than the membrane-bound splice variant, HSM1. In still other biological scenarios, both HSS1 and HSM1 may be at least transiently membrane-bound with HSM1 predicted to be less transiently membrane-bound than HSS1.

Further, mHSS1, mHSM1, hHSS1 and hHSM1 each contains at least one glycoslyation site, predicted to be at N182 (N155 in mature human protein), which is further evidence of their growth and regulatory functions in vivo. The fact that the secreted form of the polypeptides of the invention actually is glycosylated has been confirmed by the data shown in FIG. 4. Moreover, the glycoslyation pattern appears to be extensive for HSS1 and includes various structural forms in a complex network of sugar units.

mHSS1 and mHSM1 were discovered by the inventors in one of the most highly purified population of murine hematopoietic stem cells known as of the date of this disclosure. See Zhao, et al, *Blood*. 2000; 96(9):3016-22. The inventors purified these murine hematopoietic stem cells into three distinct stem cell populations, designated as +/−, +/+ and −/+ where the first notation refers to the presence of the CD38 cell surface marker and the second notation refers to the presence the CD34 cell surface markers. ("+" refers to the presence of the marker and "−" refers to the absence of the marker.) Beside the presence or absence of CD38 and CD34, these murine hematopoietic stem cells were also identified as Lin⁻, Sca⁺ and kit⁺. All three cellular populations are considered to be stem cells, but the +/− population contains the most primitive stem cells, with the +/+ population being intermediate and the −/+ population being somewhat less primitive. Thus, the most primitive and long-repopulating stem cells were identified as Lin⁻, Sca⁺, kit⁺, CD38⁺ and CD34⁻; the next intermediate population was identified as Lin⁻, Sca⁺, kit⁺, CD38⁺ and CD38⁺ and CD34⁺; and the third population, identified Lin⁻, Sca⁺, kit⁺, CD38⁻ and CD34⁺, was still less primitive and possessed only short-term repopulating ability. By analysis of the mRNA taken from each of these cell populations, the inventors found that mHSS-1 and mHSM-1 are expressed in all three hematopoietic stem cell populations with the highest expression being found in the "−/+" cell population. The probe used cannot distinguish between these two forms as it was generic to both the HSS form and the HSM form. The actual expression values obtained were as follows: +/−=1185.5; +/+=1302.3; −/+=1921.1.

The genes encoding hHSS1 and hHSM1 reside on chromosome 19 at 19q13.33. Interestingly, chromosome 19 is found to be replete with hematopoietic growth regulators/modulators. For example, FLt3 ligand, a hematopoietic stem cell growth factor, resides on human chromosome 19 near the 19q13.33 locus, and stem cell growth factor (SCGF), an early progenitor hematopoietic growth factor, resides two genes downstream from the 19q13.33 locus. The genes encoding mHSS1, and mHSM1 reside on chromosome 7 at approximately 34 million base pairs. Interestingly, Flt3 ligand, a hematopoietic stem cell growth regulator/modulator, also resides on chromosome 7 in the murine system.

Further, the locus at 19q13.3, which contains the genes for hHSS1 and hHSM1, is known as a tumor suppressor region, as allele losses of the q13.3 region of human chromosome 19 have been documented in malignant gliomas, neuroblastomas and ovarian cancers. More specifically, the deletion of the region of human chromosome 19 that encompasses the genes encoding hHSS1 and hHSM1 is associated with the presence of ovarian cancer. Thus, hHSS1 and hHSM1 have a function in the modulation/regulation of tumor growth and suppression. Additionally, hHSM1 can function as a diagnostic marker for the above-mentioned cancers, particularly ovarian cancer.

Figure 7:
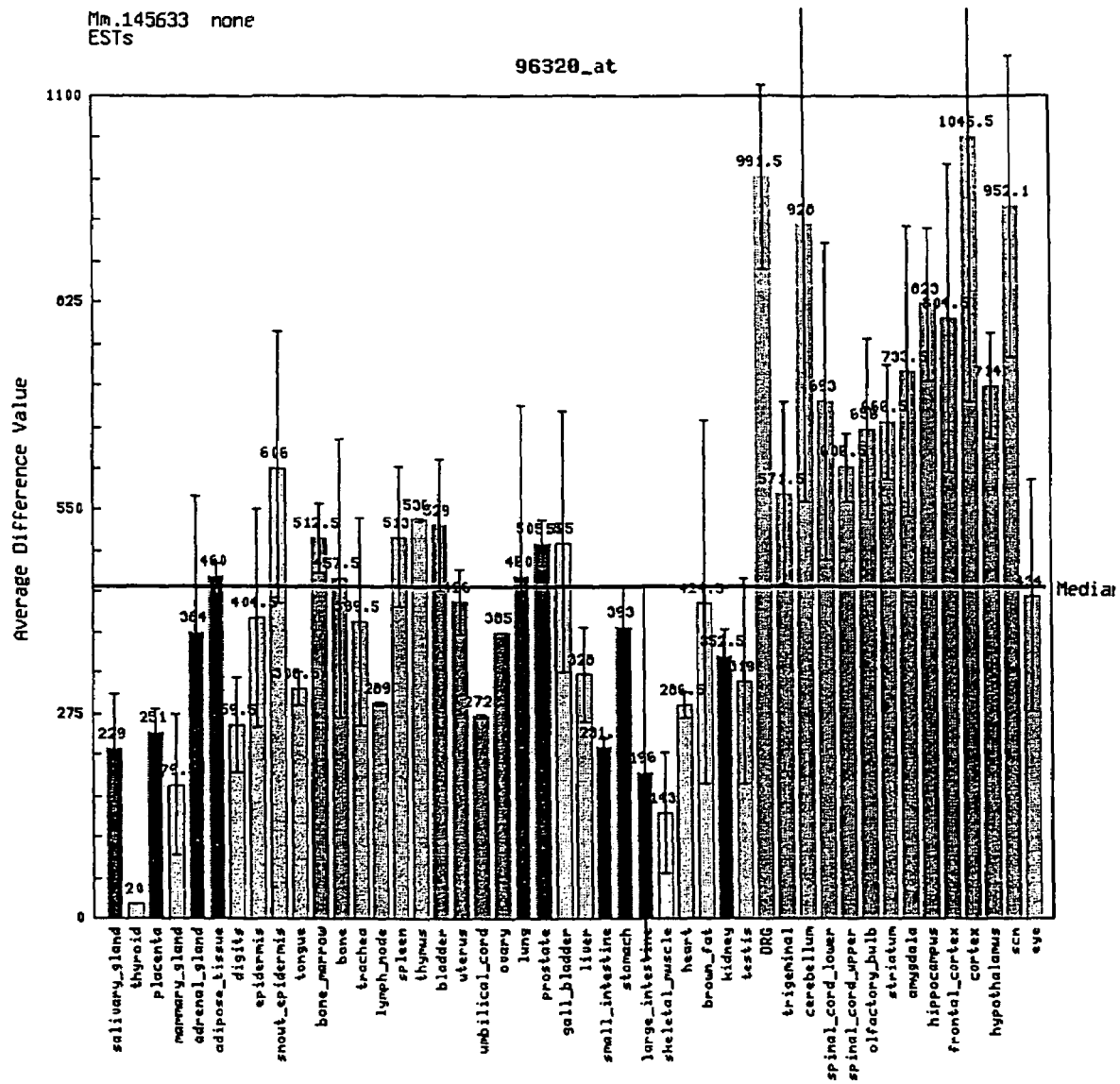
FIG. 7 depicts the mRNA expression levels of murine embodiments of the invention that encode for the polypeptide embodiments of the invention, in various tissue samples.

FIG. 7 depicts the mRNA expression pattern of the murine polypeptides of the invention in various tissue types. The probe used to identify the polypeptides of the invention in the tissue types shown was directed to a portion of the polypeptides that does not allow for distinction of mHSS and mHSM, specifically the 3'untranslated region. Thus, the expression profiles represent the sum of mHSS and mHSM in the various tissue types. FIG. 7 shows a ubiquitous mRNA expression pattern for the murine polypeptides of the invention. Above median expression of the murine polypeptides of the invention, i.e., high expression levels, are observed in the following tissues: epidermis, bone marrow, spleen, thymus, bladder, prostate, and gall bladder. Further, very high expression levels of the polypeptides of the invention are observed in neural tissue, as compared with the other tissue types tested.

The mRNA expression patterns, corresponding to the human polypeptides of the invention, i.e., hHSS1 and hHSM1, in various tissue types was determined using the Human Immune System MTC Panel (Clontech, Palo Alto, Calif. US; Cat# K1426-1) and the Human MTC Panel II (Clontech, Palo Alto, Calif. US; Cat# K1421-1). As seen with the murine homologous proteins, the mRNA corresponding to the human polypeptides of the invention were also found to be ubiquitously expressed. Specifically, the mRNA corresponding to the polypeptides of the invention were found to be expressed in bone marrow, colon with mucosal lining, fetal liver, leukocyte (peripheral blood), lymph node, ovary, prostate, small intestine, spleen, testis, thymus and tonsil.

Further, although, hHSS1 and hHSM1, were found to be widely expressed in human tissue, the expression of the secreted protein, hHSS1, or its corresponding membrane-bound splice variant, HSM1, may vary with tissue type. This notion is supported by the sequence analyses of cDNA clones derived from testis mRNA, where it was found that the relative abundance of hHSS1 to that of hHSM1 is approximately 1:7.2. The expression of mHSS1 and mHSM1 also were analyzed using a cDNA library derived from murine hematopoietic Lin⁻ bone marrow cells. This analysis revealed that the expression ratio of mHSS1 and mHSM1 was approximately 1:1. Taken together, these data indicate that the relative abundance of the secreted and membrane-bound forms of polypeptides of the invention may vary with tissue type. These data also suggest that the relative abundance of the different forms of the polypeptides of the invention may be involved in the modulation or regulation of tissue specific growth and differentiation. Moreover, the ubiquitous expression patterns of the polypeptides of the invention in both human and murine tissue appear to reinforce this notion.

II. Definitions

The term "binding partner" refers to molecules that bind with specificity to a polypeptide or nucleic acid of the invention, e.g., in an antibody-antigen interaction, in a ligand-receptor interaction, aptamer-target interaction or in a RNA-RNA interference interaction. Typically, the association will be in a natural physiologically relevant protein-protein, protein-nucleic and nucleic acid-nucleic acid interactions, but non-natural interactions are also included, such protein-nucleic acid interactions where the nucleic acid is an aptamer or nucleic acid-nucleic acid interactions, where one of the nucleic acid is an RNAi interference molecule. These binding interactions may be covalent or non-covalent, and may include members of a multimolecule complex, including carrier compounds or dimerization/oligomerization partners. The binding partner molecules may be a polymer, or chemical reagent. The term binding partner also includes molecules that possess a specific binding site that recognized a site on the polypeptides or nucleic acids of the invention.

An "isolated" polypeptide or nucleic acid is a protein, peptide, or nucleic acid, e.g., an RNA, DNA, or a mixed polymer, which is substantially separated from other biologic components which naturally accompany a native sequence, e.g., proteins and flanking genomic sequences from the originating species for a isolated nucleic acid. The term embraces a nucleic acid sequence which has been removed from its naturally occurring environment, and includes recombinant or cloned DNA isolates and chemically synthesized analogs, or analogs biologically synthesized by heterologous systems. A substantially pure molecule includes isolated forms of the molecule. An isolated nucleic acid will usually contain homogeneous nucleic acid molecules, but will, in some embodiments, contain nucleic acids with minor sequence heterogeneity. This heterogeneity is typically found at the polymer ends or portions not critical to a desired biological function or activity.

The term "polypeptide" or "protein" as used herein includes a significant fragment or segment of a "HSS", "HSM" or "HSC" molecule, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., 35, 40, 45, 50, 60, 70, 80, etc.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants. Mutation of protease cleavage sites may also be accomplished.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) Physical Biochemistry (2d ed.) W.H. Freeman & Co., San Francisco, Calif.; and Cantor and Schimmel (1980) Biophysical Chemistry parts 1-3, W.H. Freeman & Co., San Francisco, Calif. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4 S, and more preferably less than about 3 S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4.degree. C. to about 650.degree. C. Usually the temperature at use is greater than about 18.degree. C. and more usually greater than about 22.degree. C. For diagnostic purposes, the temperature will usually be about room temperature or warmer, but less than the denaturation temperature of components in the assay. For therapeutic purposes, the temperature will usually be body temperature, typically about 37.degree. C. for humans, though under certain situations the temperature may be raised or lowered in situ or in vitro. The size and structure of the polypeptide should generally be evaluated in a substantially stable state, and usually not in a denatured state. The polypeptide may be associated with other polypeptides in a quaternary structure, e.g., to confer solubility, or associated with lipids or detergents in a manner which approximates natural lipid bilayer interactions. The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein.

"Substantially pure" in a protein context typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. Similar concepts apply, e.g., to antibodies or nucleic acids.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 5-8, 11-12, 15-16 or 19-20. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See Kanehisa (1984) Nuc. Acids Res. 12:203-213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 150, 200, etc.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. Stringent temperature conditions will usually include temperatures in excess of about 30.degree.0 C., more usually in excess of about 37.degree. C., typically in excess of about 45.degree. C., more typically in excess of about 55.degree. C., preferably in excess of about 65.degree. C., and more preferably in excess of about 70.degree. C. Stringent salt conditions will ordinarily be less than about 1000 mM, usually less than about 500 mM, more usually less than about 400 mM, typically less than about 300 mM, preferably less than about 200 mM, and more preferably less than about 150 mM. See, e.g., Wetmur and Davidson (1968) J. Mol. Biol. 31:349-370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions. "HSS", "HSM" or "HSC" molecules from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human HSS1 or HSM1 protein immunogen with the amino acid sequence depicted in SEQ ID NO: 1, 2, 3 or 4 can be selected to obtain antibodies specifically immunoreactive with "HSS", "HSM" or "HSC" proteins and not with other proteins.

"Variant" nucleic acid or polypeptide sequences, when compared, exhibit significant similarity or homology. The standards for homology in nucleic acids are either measures for homology generally used in the art by sequence comparison and/or phylogenetic relationship, or based upon hybridization conditions. Hybridization conditions are described in greater detail below. Variant polypeptide sequences are defined as exhibiting significant homology and retaining substantially the same activity as the native protein.

III. Nucleic Acids

Human HSS1 and HSM1 are exemplary of a larger class of structurally and functionally related proteins. The preferred embodiments, as disclosed, will be useful in standard procedures to isolate genes from different individuals or other species, e.g., warm blooded animals, such as birds and mammals. Cross hybridization will allow isolation of related genes encoding proteins from individuals, strains, or species. A number of different approaches are available to successfully isolate a suitable nucleic acid clone based upon the information provided herein. Southern blot hybridization studies can qualitatively determine the presence of homologous genes in human, monkey, rat, dog, cow, and rabbit genomes under specific hybridization conditions.

Complementary sequences will also be used as probes or primers. Based upon identification of the likely amino terminus, other peptides should be particularly useful, e.g., coupled with anchored vector or poly-A complementary PCR techniques or with complementary DNA of other peptides. Moreover, reverse translation using the redundancy in the genetic code may provide synthetic genes which may encode essentially identical proteins.

Techniques for nucleic acid manipulation of genes encoding "HSS", "HSM" and "HSC" polypeptides, such as subcloning nucleic acid sequences encoding polypeptides into expression vectors, labelling probes, DNA hybridization, and the like are described generally in Sambrook, et al. (1989) Molecular Cloning: A Laboratory Manual (2nd ed.) Vol. 1-3, Cold Spring Harbor Laboratory, Cold Spring Harbor Press, NY, which is incorporated herein by reference. This manual is hereinafter referred to as "Sambrook, et al."

There are various methods of isolating DNA sequences encoding "HSS", "HSM" and "HSC" polypeptides. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding a "HSS", "HSM" or "HSC" polypeptide, or primers can be designed, e.g., using flanking sequence, for use in amplification techniques such as PCR, for the isolation of DNA encoding "HSS", "HSM" and "HSC" polypeptides.

To prepare a cDNA library, mRNA is isolated from cells which express a "HSS", "HSM" or "HSC" polypeptide. cDNA is prepared from the mRNA and ligated into a recombinant vector. The vector is transfected into a recombinant host for propagation, screening, and cloning. Methods for making and screening cDNA libraries are well known. See Gubler and Hoffman (1983) Gene 25:263-269 and Sambrook, et al.

For a genomic library, the DNA can be extracted from tissue and either mechanically sheared or enzymatically digested to yield fragments, e.g., of about 12-20 kb. The fragments are then separated by gradient centrifugation and cloned in bacteriophage lambda vectors. These vectors and phage are packaged in vitro, as described in Sambrook, et al. Recombinant phage are analyzed by plaque hybridization as described in Benton and Davis (1977) Science 196:180-182. Colony hybridization is carried out as generally described in e.g., Grunstein, et al. (1975) Proc. Natl. Acad. Sci. USA. 72:3961-3965.

DNA encoding a "HSS", "HSM" or "HSC" polypeptide can be identified in either cDNA or genomic libraries by its ability to hybridize with the nucleic acid probes described herein, e.g., in colony or plaque hybridization assays. The corresponding DNA regions are isolated by standard methods familiar to those of skill in the art. See, e.g., Sambrook, et al. Alternatively, sequence databases, e.g., GenBank, may be evaluated for similar or corresponding sequences.

Various methods of amplifying target sequences, such as the polymerase chain reaction, can also be used to prepare DNA encoding "HSS", "HSM" or "HSC" polypeptides. Polymerase chain reaction (PCR) technology is used to amplify such nucleic acid sequences directly from mRNA, from cDNA, and from genomic libraries or cDNA libraries. The isolated sequences encoding a "HSS", "HSM" or "HSC" polypeptide may also be used as templates for PCR amplification.

Typically, in PCR techniques, oligonucleotide primers complementary to two 5' regions in two strands of the DNA region to be amplified are synthesized. The polymerase chain reaction is then carried out using the two opposite primers. See Innis, et al. (eds.) (1990) PCR Protocols: A Guide to Methods and Applications Academic Press, San Diego, Calif. Primers can be selected to amplify the entire regions encoding a full-length "HSS", "HSM", or "HSC" protein or to amplify smaller DNA segments as desired. Once such regions are PCR-amplified, they can be sequenced and oligonucleotide probes can be prepared from sequence obtained using standard techniques. These probes can then be used to isolate DNA's encoding "HSS", "HSM" and "HSC" polypeptides.

Oligonucleotides for use as probes are usually chemically synthesized according to the solid phase phosphoramidite triester method first described by Beaucage and Carruthers (1983) Tetrahedron Lett. 22(20):1859-1862, or using an automated synthesizer, as described in Needham-VanDevanter, et al. (1984) Nucleic Acids Res. 12:6159-6168. Purification of oligonucleotides is performed, e.g., by native acrylamide gel electrophoresis or by anion-exchange HPLC as described in Pearson and Regnier (1983) J. Chrom. 255:137-149. The sequence of the synthetic oligonucleotide can be verified using, e.g., the chemical degradation method of Maxam, A. M. and Gilbert, W. in Grossman, L. and Moldave (eds.) (1980) Methods in Enzymology 65:499-560 Academic Press, New York.

Isolated nucleic acids encoding human HSS1 and human HSM1 polypeptides were identified. The nucleotide sequences and corresponding open reading frames are provided in SEQ ID NO: 5 and 7; with further sequences provided in SEQ ID NOS: 11-12, 15-16, and 19-20. Correspondingly, murine sequences were also identified and their nucleotide and corresponding open reading frames are provided as SEQ ID NO: 6 and 8.

The present invention provides isolated DNA or fragments to encode a "HSS", "HSM" or "HSC" polypeptide. In addition, this invention provides isolated or recombinant DNA which encodes a protein or polypeptide which is capable of hybridizing under appropriate conditions, e.g., high stringency, with the DNA sequences described herein. The biologically active protein or polypeptide can be an intact ligand, or fragment, and have an amino acid sequence as disclosed in SEQ ID NO: 1-4, 9-10, 13-14, 17-18, 21-30 or variant "HSS", "HSM" and "HSC" amino acid sequences, as disclosed herein. Preferred embodiments will be full length natural sequences, from isolates, e.g., about 20,000 to 30,000 daltons in size when unglycosylated, or fragments of at least about 8,000 daltons, more preferably at least about 10,000 daltons. In glycosylated form, a polypeptide of the invention may exceed 20,000 to 30,000 daltons. Further, the invention contemplates the use of isolated or recombinant DNA, or fragments thereof, which encode proteins which are homologous to a "HSS", "HSM" or "HSC" polypeptide or which were isolated using cDNA encoding a "HSS", "HSM" or "HSC" polypeptide as a probe. The isolated DNA can have the respective regulatory sequences in the 5' and 3' flanks, e.g., promoters, enhancers, poly-A addition signals, and others.

IV. Making "HSS", "HSM" and "HSC" Proteins

DNAs which encode a "HSS", "HSM" or "HSC" polypeptide or fragments thereof can be obtained by chemical synthesis, screening cDNA libraries, or by screening genomic libraries prepared from a wide variety of cell lines or tissue samples. The redundancy of the genetic code provides a number of polynucleotide sequences which should encode the same protein.

These DNAs can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies. Each "HSS", "HSM" or "HSC" polypeptide or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., "HSS", "HSM" and "HSC" polypeptides, or portions thereof, may be expressed as fusions with other proteins or possessing an epitope tag. Such is applicable also to antigen binding sites.

Expression vectors are typically self-replicating DNA or RNA constructs containing the desired antigen gene or its fragments, usually operably linked to appropriate genetic control elements that are recognized in a suitable host cell. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of the present invention encompass DNAs which encode a "HSS", "HSM" or "HSC" polypeptide, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a "HSS", "HSM" or "HSC" polypeptide in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a "HSS", "HSM" or "HSC" gene or its fragments into the host DNA by recombination, or to integrate a promoter which controls expression of an endogenous gene.

Vectors, as used herein, contemplate plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector, but many other forms of vectors which serve an equivalent function are suitable for use herein. See, e.g., Pouwels, et al. (1985 and Supplements) Cloning Vectors: A Laboratory Manual Elsevier, N.Y.; and Rodriquez, et al. (eds.) (1988) Vectors: A Survey of Molecular Cloning Vectors and Their Uses Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express "HS S", "HSM" or "HSC" polypeptides and fragments include, but are not limited to, such vectors as those containing the lac promoter (pUC-series); trp promoter (pBR322-trp); lpp promoter (the pIN-series); lambda-pp or pR promoters (pOTS); or hybrid promoters such as ptac (pDR540). See Brosius, et al. (1988) "Expression Vectors Employing Lambda-, trp-, lac-, and lpp-derived Promoters", in Rodriguez and Denhardt (eds.) Vectors: A Survey of Molecular Cloning Vectors and Their Uses 10:205-236 Buttersworth, Boston, Mass.

Lower eukaryotes, e.g., yeasts and *Dictyostelium*, may be transformed with A "HSS", "HSM", or "HSC" sequence containing vectors. For purposes of this invention, the most common lower eukaryotic host is the baker's yeast, *Saccharomyces cerevisiae*. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are typically the preferred host cells for expression of the functionally active "HSS", "HSM" and "HSC" polypeptides. In principle, many higher eukaryotic tissue culture cell lines may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) Mol. Cell. Biol. 5:1136-1142; pMC1neo Poly-A, see Thomas, et al. (1987) Cell 51:503-512; and a baculovirus vector such as pAC 373 or pAC 610.

It is likely that "HSS", "HSM" and "HSC" polypeptides need not be glycosylated to elicit biological responses. However, it will occasionally be desirable to express a "HSS", "HSM" or "HSC" polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, the "HSS", "HSM" or "HSC" gene may be co-transformed with one or more genes encoding mammalian or other glycosylating enzymes. It is further understood that over or under glycosylation may be detrimental to "HSS", "HSM" and "HSC" biological activity, and that one of skill may perform routine testing to optimize the degree of glycosylation which confers optimal biological activity.

A "HSS", "HSM", "HSC" polypeptide, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) Biochem. Biophys. Acta. 988:427-454; Tse, et al. (1985) Science 230:1003-1008; and Brunner, et al. (1991) J. Cell Biol. 114:1275-1283.

Now that "HSS", "HSM" and "HSC" polypeptides have been characterized, fragments or derivatives thereof can be prepared by conventional processes for synthesizing peptides. These include processes such as are described in Stewart and Young (1984) Solid Phase Peptide Synthesis Pierce Chemical Co., Rockford, Ill.; Bodanszky and Bodanszky (1984) The Practice of Peptide Synthesis Springer-Verlag, New York, N.Y.; and Bodanszky (1984) The Principles of Peptide Synthesis Springer-Verlag, New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The "HSS", "HSM" and "HSC" polypeptides of this invention can be obtained in varying degrees of purity depending upon its desired use. Purification can be accomplished by use of known protein purification techniques or by the use of the antibodies or binding partners herein described, e.g., in immunoabsorbant affinity chromatography. See, e.g., Coligan, et al. (eds.) (1995 and periodic supplements) Current Protocols in Protein Science, John Wiley and Sons, New York, N.Y. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the "HSS", "HSM" and "HSC" polypeptides as a result of recombinant DNA techniques, see below.

Multiple cell lines may be screened for one which expresses a "HSS", "HSM" or "HSC" polypeptide at a high level compared with other cells. Various cell lines, e.g., a mouse thymic stromal cell line TA4, is screened and selected for its favorable handling properties. Natural "HSS" and "HSM" polypeptides can be isolated from natural sources, or by expression from a transformed cell using an appropriate expression vector. Purification of the expressed protein is achieved by standard procedures, or may be combined with engineered means for effective purification at high efficiency from cell lysates or supernatants. Epitope or other tags, e.g., FLAG or His.sub.6 segments, can be used for such purification features.

V. Antibodies

Antibodies can be raised to various "HSS", "HSM" and "HSC" polypeptides, including individual, polymorphic, allelic, strain, or species variants, and fragments thereof, both in their naturally occurring (full-length) forms and in their recombinant forms. Additionally, antibodies can be raised to "HSS", "HSM" and "HSC" polypeptides in either their active or native forms or in their inactive or denatured forms. Anti-idiotypic antibodies may also be used.

a. Antibody Production

A number of immunogens may be used to produce antibodies specifically reactive with "HSS", "HSM", and "HSC" proteins. Recombinant protein is a preferred immunogen for the production of monoclonal or polyclonal antibodies. Naturally occurring protein may also be used either in pure or impure form. Synthetic peptides, made using a human or mouse "HSS", "HSM" or "HSC" protein sequence described herein, may also used as an immunogen for the production of antibodies to "HSS", "HSM" and "HSC" polypeptides. Recombinant protein can be expressed in eukaryotic or prokaryotic cells as described herein, and purified as described. Naturally folded or denatured material can be used, as appropriate, for producing antibodies. Either monoclonal or polyclonal antibodies may be generated for subsequent use in immunoassays to measure the protein.

Methods of producing polyclonal antibodies are known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the "HSS", "HSM" or "HSC" protein or fragment of interest. When appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) Eur. J. Immunol. 6:511-519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275-1281.

Antibodies, including binding fragments and single chain versions, against predetermined fragments of "HSS", "HSM" or "HSC" polypeptides can be raised by immunization of animals with conjugates of the fragments with carrier proteins as described above. Monoclonal antibodies are prepared from cells secreting the desired antibody. These antibodies can be screened for binding to normal or defective "HSS", "HSM" or "HSC" polypeptides, or screened for agonistic or antagonistic activity, e.g., mediated through a receptor. These monoclonal antibodies will usually bind with at least a Kd of about 1 mM, more usually at least about 300 µM, typically at least about 10 µM more typically at least about 30 µM, preferably at least about 10 µM, and more preferably at least about 3 µM or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) Basic and Clinical Immunology (4th ed.) Lange Medical Publications, Los Altos, Calif., and references cited therein; Harlow and Lane (1988) Antibodies: A Laboratory Manual CSH Press; Goding (1986) Monoclonal Antibodies: Principles and Practice (2d ed.) Academic Press, New York, N.Y.; and particularly in Kohler and Milstein (1975) Nature 256:495-497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," Science 246: 1275-1281; and Ward, et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) Proc. Nat'l Acad. Sci. USA 86:10029-10033.

The antibodies of this invention are useful for affinity chromatography in isolating a "HSS", "HSM" or "HSC" protein. Columns can be prepared where the antibodies are linked to a solid support, e.g., particles, such as agarose, SEPHADEX, or the like, where a cell lysate or supernatant may be passed through the column, the column washed, followed by increasing concentrations of a mild denaturant, whereby a purified "HSS", "HSM" or "HSC" protein will be released.

The antibodies may also be used to screen expression libraries for particular expression products. Usually the antibodies used in such a procedure will be labeled with a moiety allowing easy detection of presence of antigen by antibody binding.

Antibodies to "HSS", "HSM" or "HSC" polypeptides may be used for the identification of cell populations expressing a "HSS", "HSM" or "HSC" polypeptide. By assaying the expression products of cells expressing a "HSS", "HSM" or "HSC" polypeptide it is possible to diagnose disease, e.g., immune-compromised conditions.

Antibodies raised against each "HSS", "HSM" or "HSC" polypeptide will also be useful to raise anti-idiotypic antibodies. These will be useful in detecting or diagnosing various immunological conditions related to expression of the respective antigens.

b. Immunoassays

A particular protein can be measured by a variety of immunoassay methods. For a review of immunological and immunoassay procedures in general, see Stites and Terr (eds.) (1991) Basic and Clinical Immunology (7th ed.). Moreover, the immunoassays of the present invention can be performed in many configurations, which are reviewed extensively in Maggio (ed.) (1980) Enzyme Immunoassay CRC Press, Boca Raton, Fla.; Tijan (1985) "Practice and Theory of Enzyme Immunoassays," Laboratory Techniques in Biochemistry and Molecular Biology, Elsevier Science Publishers B. V., Amsterdam; and Harlow and Lane Antibodies. A Laboratory Manual, supra, each of which is incorporated herein by reference. See also Chan (ed.) (1987) Immunoassay: A Practical Guide Academic Press, Orlando, Fla.; Price and Newman (eds.) (1991) Principles and Practice of Immunoassays Stockton Press, NY; and Ngo (ed.) (1988) Non-isotopic Immunoassays Plenum Press, NY.

Immunoassays for measurement of "HSS", "HSM" and "HSC" polypeptides can be performed by a variety of methods known to those skilled in the art. In brief, immunoassays to measure the protein can be competitive or noncompetitive binding assays. In competitive binding assays, the sample to be analyzed competes with a labeled analyte for specific binding sites on a capture agent bound to a solid surface. Preferably the capture agent is an antibody specifically reactive with a "HSS", "HSM" or "HSC" polypeptide produced as described above. The concentration of labeled analyte bound to the capture agent is inversely proportional to the amount of free analyte present in the sample.

In a competitive binding immunoassay, the "HSS", "HSM" or "HSC" polypeptide present in the sample competes with labeled protein for binding to a specific binding agent, for example, an antibody specifically reactive with the "HSS", "HSM" or "HSC" polypeptide. The binding agent may be bound to a solid surface to effect separation of bound labeled protein from the unbound labeled protein. Alternatively, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

"HSS", "HSM" and "HSC" polypeptides may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of "HSS", "HSM" and "HSC" polypeptides in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above employ labeled assay components. The label may be coupled directly or indirectly to the desired component of the assay according to methods well known in the art. A wide variety of labels and methods may be used. Traditionally, a radioactive label incorporating $H^3$, $I^{125}$, $S^{35}$, $C^{14}$, or 32 $P^{32}$ are used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) Basic and Clinical Immunology (7th ed.) supra, Maggio (ed.) Enzyme Immunoassay, supra; and Harlow and Lane Antibodies, A Laboratory Manual, supra.

In brief, immunoassays to measure antisera reactive with "HSS", "HSM" or "HSC" polypeptides can be competitive or noncompetitive binding assays. In competitive binding assays, the sample analyte competes with a labeled analyte for specific binding sites on a capture agent bound to a solid surface. Preferably the capture agent is a purified recombinant HSS", "HSM" or "HSC" polypeptide produced as described above. Other sources of "HSS", "HSM" and "HSC" polypeptides, including isolated or partially purified naturally occurring protein, may also be used. Noncompetitive assays include sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labeled binding agent can be used. A variety of different immunoassay formats, separation techniques, and labels can be also be used similar to those described above for the measurement of "HSS", "HSM" and "HSC" polypeptides.

VI. Purified "HSS", "HSM" and "HSC" Proteins

Human "HSS", "HSM" and "HSC" amino acid sequences are provided in SEQ ID NOS: 1, 3, 9, 13, 17, 21, 23, 25, 27 and 29. Murine amino acid sequences are provided in SEQ ID NO: 5, 6, 7, and 8.

Purified protein or defined peptides are useful for generating antibodies by standard methods, as described above. Synthetic peptides or purified protein can be presented to an immune system to generate polyclonal and monoclonal antibodies. See, e.g., Coligan (1991) Current Protocols in Immunology Wiley/Greene, NY; and Harlow and Lane (1989) Antibodies: A Laboratory Manual Cold Spring Harbor Press, NY, which are incorporated herein by reference. Alternatively, a "HSS", "HSM" or "HSC" receptor can be useful as a specific binding reagent, and advantage can be taken of its specificity of binding, for, e.g., purification of a "HSS", "HSM" or "HSC" ligand.

The specific binding composition can be used for screening an expression library made from a cell line which expresses a "HSS", "HSM" or "HSC" polypeptide. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library, including natural allelic an polymorphic variants.

The peptide sequences allow preparation of peptides to generate antibodies to recognize such segments, and allow preparation of oligonucleotides which encode such sequences. The sequence also allows for synthetic preparation, e.g., see Dawson, et al. (1994) Science 266:776-779. Since "HSS" and "HSC" polypeptides appear to be soluble proteins, the gene will normally possess an N-terminal signal sequence, which is removed upon processing and secretion. The putative cleavage site for the proteins of the invention is between amino acids 27 (gly) and 28 (ser) in SEQ ID NOS: 1-4, 9-10, 13-14 and 17-18 though it may be slightly altered in either direction.

VII. Physical Variants

The present invention also encompasses proteins (polypeptides) or peptides having substantial amino acid sequence similarity with an amino acid sequence of a "HSS", "HSM" or "HSC" molecule. Natural variants include individual, polymorphic, allelic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural polymorphic, allelic, and interspecies variations in each respective protein sequence. Typical homologous proteins or peptides will have from 50-100% similarity (if gaps can be introduced), to 75-100% similarity (if conservative substitutions are included) with the amino acid sequence of a "HSS", "HSM" or "HSC" polypeptide. Similarity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham, et al. (1970) J. Mol. Biol. 48:443-453; Sankoff, et al. (1983) Time Warps, String Edits, and Macromolecules: The Theory and Practice of Sequence Comparison Chapter One, Addison-Wesley, Reading, Mass.; and software packages from IntelliGenetics, Mountain View, Calif.; and the University of Wisconsin Genetics Computer Group, Madison, Wis.

Nucleic acids encoding mammalian "HSS", "HSM" and "HSC" polypeptides will typically hybridize to the nucleic acid sequence of SEQ ID NOS: 5-8 under stringent conditions. For example, nucleic acids encoding human HSS1 proteins will normally hybridize to the nucleic acid of SEQ ID NO: 1 under stringent hybridization conditions. Generally, stringent conditions are selected to be about 10.degree. C. lower than the thermal melting point (Tm) for the probe sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 50.degree. C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 mM NaCl at 42.degree. C.

An isolated "HSS", "HSM", or "HSC" DNA can be readily modified by nucleotide substitutions, nucleotide deletions, nucleotide insertions, and short inversions of nucleotide stretches. These modifications result in novel DNA sequences which encode "HSS", "HSM" and "HSC" antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant "HS S", "HSM" and "HSC" derivatives include predetermined or site-specific mutations of the respective protein or its fragments. "Mutant "HSS", "HSM" and "HSC"" encompasses a polypeptide otherwise falling within the homology definition of the human or murine HSS", "HSM" and "HSC" as set forth above, but having an amino acid sequence which differs from that of a HSS", "HSM" and "HSC" as found in nature, whether by way of deletion, substitution, or insertion. In particular, "site specific mutant "HSS", "HSM" and "HSC"" generally includes proteins having significant similarity with a protein having a sequence of SEQ ID NO: 1-4, 9-10, 13-14, 17-18 or 21-30, and as sharing various biological activities, e.g., antigenic or immunogenic, with those sequences, and in preferred embodiments contain most or all of the disclosed sequence. This applies also to polymorphic variants from different individuals. Similar concepts apply to different "HSS", "HSM" and "HSC" proteins (polypeptides), particularly those found in various warm blooded animals, e.g., mammals and birds. As stated before, it is emphasized that descriptions are generally meant to encompass other "HSS", "HSM" and "HSC" proteins, not limited to the human or murine embodiments specifically disclosed herein.

Although site specific mutation sites are predetermined, mutants need not be site specific. "HSS", "HSM" and "HSC" mutagenesis can be conducted by making amino acid insertions or deletions. Substitutions, deletions, insertions, or any combinations may be generated to arrive at a final construct. These include amino acid residue substitution levels from none, one, two, three, five, seven, ten, twelve, fifteen, etc. Insertions include amino- or carboxyl-terminal fusions, e.g. epitope tags. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins, both the "HSS" and "HSM" or antigen binding sites. A heterologous fusion protein is a fusion of proteins or segments which are naturally not normally fused in the same manner. Thus, the fusion product of an immunoglobulin with a "HSS", "HSM" and "HSC" polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, protein-binding or other segments may be "swapped" between different new fusion polypeptides or fragments. See, e.g., Cunningham, et al. (1989) Science 243:1330-1336; and O'Dowd, et al. (1988) J. Biol. Chem. 263:15985-15992. Thus, new chimeric polypeptides exhibiting new combinations of specificities will result from the functional linkage of protein-binding specificities and other functional domains.

VIII. Binding Agent: "HSS", "HSM" and "HSC" Protein Complexes

A "HSS", "HSM" and "HSC" protein (polypeptide) that specifically binds to or that is specifically immunoreactive with an antibody generated against a defined immunogen, such as an immunogen consisting of the amino acid sequence of SEQ ID NO: 1. 2, 3, 4 or variant proteins as described herein is typically determined in an immunoassay. The immunoassay uses a polyclonal antiserum which was raised to a protein of SEQ ID NO: 1. 2, 3, 4 or a variant protein. This antiserum is selected to have low crossreactivity against other like proteins and any such crossreactivity is removed by immunoabsorbtion prior to use in the immunoassay. In order to produce antisera for use in an immunoassay, the protein of SEQ ID NO: 1. 2, 3, 4, or related protein is isolated as described herein. For example, recombinant protein may be produced in a mammalian cell line. An inbred strain of mice such as balb/c is immunized with the protein of SEQ ID NO: 1. 2, 3, 4, or related protein using a standard adjuvant, such as Freund's adjuvant, and a standard mouse immunization protocol (see Harlow and Lane, supra). Alternatively, a synthetic peptide, preferably near full length, derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of 10.sup.4 or greater are selected and tested for their cross reactivity against functionally related proteins, using a competitive binding immunoassay such as the one described in Harlow and Lane, supra, at pages 570-573.

Immunoassays in the competitive binding format can be used for the crossreactivity determinations. For example, a protein of SEQ ID NO: 1. 2, 3, 4 or a related protein can be immobilized to a solid support. Proteins added to the assay compete with the binding of the antisera to the immobilized antigen. The ability of the above proteins to compete with the binding of the antisera to the immobilized protein is compared to the protein of SEQ ID NO: 1, 2, 3, 4 or a related protein. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (e.g., a portion of SEQ ID NO: 1. 2, 3, 4 or a related protein). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2, for example, that is required, then the second protein is said to specifically bind to an antibody generated to the immunogen.

It is understood that "HSS", "HSM" and "HSC" proteins are a family of homologous proteins. For a particular gene product, such as the human "HSS", "HSM" and "HSC" proteins, the term refers not only to the amino acid sequences disclosed herein, but also to other proteins that are polymorphic, allelic, non-allelic, or species variants. It is also understood that the term "human "HSS", "HSM" and "HSC"" or "mouse "HSS", "HSM" and "HSC"" includes nonnatural mutations introduced by deliberate mutation using conventional recombinant technology such as single site mutation, or by excising short sections of DNA encoding HSS", "HSM" and "HSC" proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring "HSS", "HSM" and "HSC" protein, for example, the human HSS", "HSM" and "HSC" protein shown in SEQ ID NO: 1 or 3. The biological properties of the altered proteins can be determined by expressing the protein in an appropriate cell line and measuring, e.g., a modulation effect of a "HSS", "HSM" and "HSC" polypeptide. Particular protein modifications considered minor would include conservative substitution of amino acids with similar chemical properties, as described above for the "HSS", "HSM" and "HSC" family as a whole.

IX. Functional Variants

The blocking of physiological response to "HSS", "HSM" and "HSC" proteins may result from the inhibition of binding of the protein to its receptor, e.g., through competitive inhibition. Thus, in vitro assays of the present invention will often use isolated protein, membranes from cells expressing a recombinant membrane associated protein of the invention, namely HSM1 forms and variant HSM1 forms, soluble fragments comprising receptor binding segments of these proteins, or fragments attached to solid phase substrates. These assays will also allow for the diagnostic determination of the effects of either binding segment mutations and modifications, or protein mutations and modifications, e.g., protein analogs. The present invention also contemplates the use of competitive drug screening assays, e.g., where neutralizing antibodies to antigen or receptor fragments compete with a test compound for binding to the protein. In this manner, the antibodies can be used to detect the presence of a polypeptide which shares one or more antigenic binding sites of the protein and can also be used to occupy binding sites on the protein that might otherwise interact with a receptor.

"Derivatives" of "HSS", "HSM" and "HSC" antigens include amino acid sequence mutants, glycosylation variants, and covalent or aggregate conjugates with other chemical moieties. Covalent derivatives can be prepared by linkage of functionalities to groups which are found in "HSS", "HSM" and "HSC" amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. See, e.g., Coligan, et al. (eds.) (1995 and periodic supplements) Current Protocols in Protein Science, John Wiley and Sons, New York, N.Y. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the "HSS", "HSM" and "HSC" or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between "HSS", "HSM" and "HSC" proteins and other homologous or heterologous proteins are also provided. Many growth factors and cytokines are homodimeric entities, and a repeat construct may have various advantages, including lessened susceptibility to proteolytic degradation. Moreover, many receptors require dimerization to transduce a signal, and various dimeric proteins or domain repeats can be desirable. Heterologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial .beta.-galactosidase, trpE, Protein A, .beta.-lactamase, alpha amylase, alcohol dehydrogenase, and yeast alpha mating factor. See, e.g., See, e.g., Dawson, et al. (1994) Science 266:776-779; and Godowski, et al. (1988) Science 241:812-816. In particular, fusion proteins with portions from the related genes will be useful. Similar concepts of fusions with antigen binding sites are contemplated.

Such polypeptides may also have amino acid residues which have been chemically modified by phosphorylation, sulfonation, biotinylation, acylation, lipidation or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of HSS", "HSM" and "HSC" proteins other than variations in amino acid sequence or glycosylation. Such derivatives may involve covalent or aggregative association with chemical moieties. These derivatives include: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a "HSS", "HSM" and "HSC" antigen can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-"HSS", anti-"HSM" and anti-"HSC" antibodies or its receptor. The HSS", "HSM" and "HSC" polypeptides can also be labeled with a detectable group, e.g., radioiodinated by the chloramine T procedure, covalently bound to rare earth chelates, or conjugated to another fluorescent moiety for use in diagnostic assays. Purification of HSS", "HSM" and "HSC" proteins may be effected by immobilized antibodies or receptor.

Isolated "HSS", "HSM" and "HSC" genes will allow transformation of cells lacking expression of corresponding "HSS", "HSM" and "HSC" proteins, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of "HSS", "HSM" and "HSC" receptor proteins. Subcellular fragments, e.g., cytoplasts or membrane fragments, can be isolated and used.

X. Uses

The present invention provides reagents which will find use in diagnostic applications as described herein, e.g., below in the description of kits for diagnosis.

The "HSS", "HSM" and "HSC" nucleotides, e.g., human or mouse "HSS", "HSM" and "HSC" DNA or RNA, may be used as a component in a forensic assay. For instance, the nucleotide sequences provided may be labeled using, e.g., $P^{32}$ or biotin and used to probe standard restriction fragment polymorphism blots, providing a measurable character to aid in distinguishing between individuals. Such probes may be used in well-known forensic techniques such as genetic fingerprinting. In addition, nucleotide probes made from "HSS", "HSM" and "HSC" sequences may be used in in situ assays to detect chromosomal abnormalities. For instance, rearrangements in human chromosome 19 encoding a "HSS", "HSM" and "HSC" gene may be detected via well-known in situ techniques, using "HSS", "HSM" and "HSC" probes in conjunction with other known chromosome markers.

Antibodies, aptamers, RNAi molecules and other binding agents directed towards HSS", "HSM" and "HSC" proteins or nucleic acids may be used to purify the corresponding HSS", "HSM" and "HSC" molecule. Antibody purification of "HSS", "HSM" and "HSC" proteins is both possible and practicable. Antibodies and other binding agents may also be used in a diagnostic fashion to determine whether "HSS", "HSM" and "HSC" proteins are present in a tissue sample or cell population using well-known techniques described herein. The ability to attach a binding agent to a "HSS", "HSM" and "HSC" protein provides a means to diagnose disorders associated with "HSS", "HSM" and "HSC" dysregulation. Antibodies and other "HSS", "HSM" and "HSC" binding agents may also be useful as histological markers. As described above, "HSS", "HSM" and "HSC" mRNA expression is limited to specific tissue types. By directing a probe, such as an antibody or nucleic acid to a "HSS", "HSM" and "HSC" mRNA, it is possible to use the probe to distinguish tissue and cell types in situ or in vitro.

This invention also provides reagents with significant therapeutic value. The "HSS", "HSM" and "HSC" proteins (naturally occurring or recombinant), fragments thereof, and antibodies thereto, along with compounds identified as having binding affinity to a "HSS", "HSM" or "HSC" protein (polypeptide) or fragment are useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a "HSS", "HSM" or "HSC" polypeptide is a target for an agonist or antagonist of the protein.

The "HSS", "HSM" and "HSC" proteins(polypeptides) likely play a role in regulation or development of hematopoietic cells or neuronal cells, e.g., hematopoietic stem and progenitor cells, which affect hematological responses directly or indirectly. An example of a direct role for "HSS", "HSM" and "HSC" proteins(polypeptides) is that these protein factors may act in an autocrine fashion to regulate, hematopoietic stem cells as self-renewal factor, growth factor of differentiation factor. Hematopoietic stem cells are known to express autocrine factors, as such an autocrine role for "HSS", "HSM" and "HSC" proteins (polypeptides) is consistent with known stem cell properties. Hematopoietic stem cells produce for example all three hedgehog proteins, a number of wnt molecules and also receptors for these molecules (inventor's unpublished data). Other examples of signaling factors expressed in hematopoietic stem cells (inventor's unpublished data) are interferons, interleukins, chemokines and cytokines and small peptides such as apelin. Another example is "HSS", "HSM" and "HSC" proteins or related polypeptides may modulate non-hematopoietic cells in the stem cell niche, such as osteoclast, endothelial or stromal cells. Recent reports have shown the importance of osteoclasts (or osteoblasts) in the stem cell niche and that their numbers and association with stem cells in the bone marrow contribute to stem cell self renewal. "HSS", "HSM", "HSC" and related polypeptides may act upon associated bone marrow cells in close proximity to the stem cells to maintain and support osteoclast, stromal, endothelial or other cell growth which in turn support stem cell self renewal or other forms of hematopoiesis. An example of this type of stem cell niche regulation is the following. Stem cells are seen to express high levels of CCL9 (aka Mipγ) but not its corresponding receptor, CXCR9. But Mipγ and its receptor are a major growth factor system for osteoclasts. In this way stem cells and associated niche cells are seen to regulate each other. "HSS", "HSM" and "HSC" may act on niche cell types that in turn support hematopoiesis. As such, "HSS", "HSM" and "HSC" proteins would be likely factors for the maintenance and expansion of stem cells in an ex vivo system reconstituting the stem cell niche of bone marrow. Similarly "HSS", "HSM" and "HSC" proteins can act as factors for self renewal in an ex vivo artificial bone marrow system as have been developed or are under development (MIT, U. Michigan). Further, "HSS", "HSM" and "HSC" proteins may act as extracellular molecules involved in binding cytokines or other extracellular signaling molecules. Such properties would contribute to maintaining local concentrations of factors which act on stem cells or local concentration gradients necessary for polar mechanisms associated with hematopoiesis, such as cell asymmetric division in the stem cell niche. As such "HSS", "HSM" and "HSC" proteins contribute to hematopoiesis as an adjunct molecule necessary for proper factor initiated activation of stem cells and subsequent maturation. Related to these roles in hematopoiesis are aspects of glycosylation. Glycosylation states of extracellular proteins are known to be of importance for support of hematopoiesis. HSS1, as depicted in FIG. 4, is seen to be glycosylated and have a number of glycosylic isoforms and glycosyl moieties. Moreover, specific moieties are known to support hematopoiesis whereas others do not. Another role for the polypeptides of the invention in hematopoietic stem cells is as marker that can be used to further identify hematopoietic stem cells. For this use "HSM" forms of the proteins of the invention would be useful as a membrane-bound component of hematopoietic stem cells.

In addition, abnormal developmental conditions are known in cell types shown to possess "HSS", "HSM" and "HSC" mRNAs by northern blot analysis. See Berkow (ed.) The Merck Manual of Diagnosis and Therapy, Merck & Co., Rahway, N.J.; and Thorn, et al. Harrison's Principles of Internal Medicine, McGraw-Hill, N.Y. Developmental or functional abnormalities, e.g., of the neuronal or hematopoietic system, cause significant medical abnormalities and conditions which may be susceptible to prevention or treatment using compositions provided herein. For instance, leukemia is an abnormality in hematopoiesis and hematopoietic stem cells that may be prevented or treated using "HSS", "HSM" and "HSC" proteins (polypeptides) or fragments thereof.

Recombinant "HSS", "HSM" and "HSC" proteins (polypeptides) or fragments thereof, or "HSS", "HSM" and "HSC" antibodies can be purified and then administered to a patient, e.g., in sterile form. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to "HSS", "HSM" and "HSC" proteins, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity can activate the receptor and is thus an agonist in that it simulates the activity of a "HSS", "HSM" and "HSC" protein. The present invention further contemplates the therapeutic use of antibodies to "HSS", "HSM" and "HSC" as antagonists. This approach should be particularly useful with other "HSS", "HSM" and "HSC" species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) Goodman and Gilman's: The Pharmacological Bases of Therapeutics (8th ed.) Pergamon Press; and (1990) Remington's Pharmaceutical Sciences (17th ed.) Mack Publishing Co., Easton, Pa. Methods for administration are discussed therein and below, e.g., for oral, intravenous, intraperitoneal, or intramuscular administration, transdermal diffusion, inhalation and others. Pharmaceutically acceptable carriers will include water, saline, buffers, and other compounds described, e.g., in the Merck Index, Merck & Co., Rahway, N.J. Dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

"HSS", "HSM" and "HSC" proteins (polypeptides), fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) Goodman and Gilman's: The Pharmacological Bases of Therapeutics (8th ed.) Pergamon Press; and (1990) Remington's Pharmaceutical Sciences (17th ed.) Mack Publishing Co., Easton, Pa.; Avis, et al. (eds.) (1993) Pharmaceutical Dosage Forms: Parenteral Medications Dekker, N.Y.; Lieberman, et al. (eds.) (1990) Pharmaceutical Dosage Forms: Tablets Dekker, N.Y.; and Lieberman, et al. (eds.) (1990) Pharmaceutical Dosage Forms: Disperse Systems Dekker, N.Y. The therapy of this invention may be combined with or used in association with other therapeutic agents.

Both the naturally occurring and the recombinant forms of the "HSS", "HSM" and "HSC" proteins and nucleic acids of the present invention are particularly useful in kits and assay methods which are capable of screening compounds for binding activity to the proteins or nucleic acids. Several methods of automating assays have been developed in recent years so as to permit screening of tens of thousands of compounds in a short period. See, e.g., Fodor, et al. (1991) Science 251:767-773; and other descriptions of chemical diversity libraries, which describe means for testing of binding affinity by a plurality of compounds. The development of suitable assays can be greatly facilitated by the availability of large amounts of purified, soluble "HSS" and "HSC" as provided by the present invention.

For example, antagonists can normally be found once the protein has been structurally defined. Testing of potential protein analogs is now possible upon the development of highly automated assay methods using a purified receptor. In particular, new agonists and antagonists will be discovered by using screening techniques described herein.

The present invention is particularly useful for screening compounds by using recombinant protein in a variety of drug screening techniques. The advantages of using a recombinant protein in screening for specific ligands include: (a) improved renewable source of "HSS", "HSM" and "HSC" proteins (polypeptides) from a specific source; (b) potentially greater number of ligands per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a "HSS", "HSM" or "HSC" receptor. Cells may be isolated which express a receptor in isolation from any others. Such cells, either in viable or fixed form, can be used for standard ligand/receptor binding assays. See also, Parce, et al. (1989) Science 246:243-247; and Owicki, et al. (1990) Proc. Nat'l Acad. Sci. USA 87:4007-4011, which describe sensitive methods to detect cellular responses. Competitive assays are particularly useful, where the cells (source of "HSS", "HSM" and "HSC" proteins (polypeptides)) are contacted and incubated with a labeled receptor or antibody having known binding affinity to the ligand, such as $I^{125}$-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on "HSS", "HSM" and "HSC" proteins (polypeptides)-mediated functions, e.g., second messenger levels, i.e., $Ca^{2+}$; cell proliferation; inositol phosphate pool changes; and others. Some detection methods allow for elimination of a separation step, e.g., a proximity sensitive detection system. Calcium sensitive dyes will be useful for detecting $Ca^{2+}$ levels, with a fluorimeter or a fluorescence cell sorting apparatus.

Another method utilizes membranes from transformed eukaryotic or prokaryotic host cells as the source of a "HSS", "HSM" and "HSC" proteins (polypeptides). These cells are stably transformed with DNA vectors directing the expression of a "HSS", "HSM" or "HSC" protein (polypeptide), e.g., an engineered membrane bound form. Essentially, the membranes would be prepared from the cells and used in a receptor/ligand binding assay such as the competitive assay set forth above.

Still another approach is to use solubilized, unpurified or solubilized, purified "HSS", "HSM" or "HSC" proteins (polypeptides) from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to a "HSS", "HSM" or "HSC" antibody and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified "HSS", "HSM" and "HSC" antibody, and washed. The next step involves detecting bound "HSS", "HSM" and "HSC" antibody.

Rational drug design may also be based upon structural studies of the molecular shapes of the "HSS", "HSM" and "HSC" proteins (polypeptides) and other effectors or analogs. See, e.g., Methods in Enzymology vols 202 and 203. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) Protein Crystallography Academic Press, NY.

A purified "HSS", "HSM" or "HSC" protein (polypeptide) can be coated directly onto plates for use in the aforementioned drug screening techniques. However, non-neutralizing antibodies to these ligands can be used as capture antibodies to immobilize the respective ligand on the solid phase.

XI. Kits

The present invention also contemplates use of "HSS", "HSM" and "HSC" proteins, fragments thereof, peptides, and their fusion products in a variety of diagnostic kits and methods for detecting the presence of "HSS", "HSM", "HSC" proteins (polypeptides) or fragments thereof or a "HSS", "HSM" or "HSC" receptor. Typically the kit will have a compartment containing either a defined "HSS", "HSM" or "HSC" protein (polypeptide) or fragments thereof, peptide or gene segment or a reagent which recognizes one or the other, e.g., receptor fragments or antibodies.

A kit for determining the binding affinity of a test compound to a "HSS", "HSM" or "HSC" protein (polypeptide) or fragments thereof would typically comprise a test compound; a labeled compound, e.g., a receptor or antibody having known binding affinity for the particular "HSS", "HSM" and "HSC" protein (polypeptide) or fragments thereof; a source of "HSS", "HSM" and "HSC" proteins (polypeptides) or fragments thereof (naturally occurring or recombinant); and a means for separating bound from free labeled compound, such as a solid phase for immobilizing the "HSS", "HSM" and "HSC" proteins (polypeptides) or fragments thereof. Once compounds are screened, those having suitable binding affinity to the "HSS", "HSM" and "HSC" proteins (polypeptides) or fragments thereof can be evaluated in suitable biological assays, as are well known in the art, to determine whether they act as agonists or antagonists to the receptor. The availability of recombinant "HSS", "HSM" and "HSC" proteins (polypeptides) also provide well defined standards for calibrating such assays.

A preferred kit for determining the concentration of, for example, a "HSS", "HSM" or "HSC" protein (polypeptide) or fragments thereof in a sample would typically comprise a labeled compound, e.g., receptor or antibody, having known binding affinity for "HSS", "HSM" and "HSC" proteins (polypeptides) or fragments thereof, a source of "HSS", "HSM" or "HSC" proteins (polypeptides) (naturally occurring or recombinant), and a means for separating the bound from free labeled compound, for example, a solid phase for immobilizing the "HSS", "HSM" or "HSC" protein (polypeptide) or fragments thereof. Compartments containing reagents, and instructions, will normally be provided.

Antibodies, including antigen binding fragments, specific for "HSS", "HSM" and "HSC" proteins (polypeptides) or ligand fragments are useful in diagnostic applications to detect the presence of elevated levels of "HSS", "HSM" and "HSC" proteins polypeptides) and/or its fragments. Such kits may allow diagnosis of the amounts of differently processed forms of "HSS", "HSM" and "HSC" proteins (polypeptides). Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and antigen-"HSS", antigen-"HSM" and antigen-"HSC" complex) or heterogeneous (with a separation step). Various commercial assays exist, such as radioimmunoassay (RIA), enzyme-linked immunosorbentassay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a "HSS", "HSM" or "HSC" proteins (polypeptides) or to a particular fragment thereof. Similar assays have also been extensively discussed in the literature. See, e.g., Harlow and Lane (1988) Antibodies: A Laboratory Manual, CSH Press, NY; Chan (ed.) (1987) Immunoassay: A Practical Guide Academic Press, Orlando, Fla.; Price and Newman (eds.) (1991) Principles and Practice of Immunoassay Stockton Press, NY; and Ngo (ed.) (1988) Nonisotopic Immunoassay Plenum Press, NY.

Anti-idiotypic antibodies may have similar use to diagnose presence of antibodies against a "HSS", "HSM" and "HSC" proteins (polypeptides) or fragments thereof, as such may be diagnostic of various abnormal states. For example, overproduction of "HSS", "HSM" and "HSC" proteins (polypeptides) may result in production of various immunological or other medical reactions which may be diagnostic of abnormal physiological states, e.g., in cell growth, activation, or differentiation.

Frequently, the reagents for diagnostic assays are supplied in kits, so as to optimize the sensitivity of the assay. For the present invention, depending upon the nature of the assay, the protocol, and the label, either labeled or unlabeled antibody or receptor, or labeled "HSS", "HSM" or "HSC" protein (polypeptide) or fragments thereof is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification, or may be modified in a variety of ways. For example, labeling may be achieved by covalently or non-covalently joining a moiety which directly or indirectly provides a detectable signal. In any of these assays, the protein, test compound, "HSS", "HSM" or "HSC" proteins (polypeptides) or fragments thereof, or antibodies thereto can be labeled either directly or indirectly. Possibilities for direct labeling include label groups: radiolabels such as 1125, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. One or more "HSS", "HSM" and "HSC" proteins (polypeptides) or fragments thereof can be immobilized on various matrices followed by washing. Suitable matrices include plastic such as an ELISA plate, filters, and beads. Methods of immobilizing "HSS", "HSM" and "HSC" proteins (polypeptides) or fragments thereof to a matrix include, without limitation, direct adhesion to plastic, use of a capture antibody, chemical coupling, and biotin-avidin. The last step in this approach involves the precipitation of ligand/receptor or ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) Clin. Chem. 30:1457-1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a "HSS", "HSM" or "HSC" protein (polypeptide) or fragment thereof. These sequences can be used as probes for detecting levels of a "HSS", "HSM" or "HSC" proteins (polypeptides) or fragments thereof message in samples from natural sources, or patients suspected of having an abnormal condition, e.g., cancer or developmental problem. The preparation of both RNA and DNA nucleotide sequences, the labeling of the sequences, and the preferred. size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $P^{32}$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out using many conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) Progress in Growth Factor Res. 1:89-97.

Additionally, diagnostic kits for use of "HSS", "HSM" and "HSC" proteins (polypeptides) or fragments thereof as factors for the modulation of hematopoiesis or neurogenesis can be assembled where "HSS", "HSM" and "HSC" proteins (polypeptides) or fragments thereof are prepared in separate containers with instructions for the use of the proteins or fragments in hematopoietic or neuronal modulation assays.

XII. Receptor Isolation

Having isolated a binding partner of a specific interaction, methods exist for isolating the counter-partner. See, Gearing, et al. (1989) EMBO J. 8:3667-3676. For example, means to label a "HSS", "HSM" or "HSC" protein (polypeptide) or fragments thereof without interfering with the binding to its receptor can be determined. For example, an affinity label or epitope tag can be fused to either the amino- or carboxyl-terminus of the ligand. An expression library can be screened for specific binding of "HSS", "HSM" and "HSC" proteins (polypeptides) or fragments thereof, e.g., by cell sorting, or other screening to detect subpopulations which express such a binding component. See, e.g., Ho, et al. (1993) Proc. Nat'l Acad. Sci. USA 90:11267-11271. Alternatively, a panning method may be used. See, e.g., Seed and Aruffo (1987) Proc. Nat'l Acad. Sci. USA 84:3365-3369. A two-hybrid selection system may also be applied making appropriate constructs with the available BAS-1 sequences. See, e.g., Fields and Song (1989) Nature 340:245-246.

Protein cross-linking techniques with label can be applied to isolate binding partners of a "HSS", "HSM" or "HSC" protein (polypeptide) or fragments thereof. This would allow identification of proteins which specifically interact with a "HSS", "HSM" or "HSC" proteins (polypeptides), e.g., in a ligand-receptor like manner.

XIII. Aptamers

Specific aptamers can be generated to HSS", "HSM" or "HSC" proteins (polypeptides) or fragments thereof and variant molecules as disclosed herein. Aptamers are macromolecules composed of nucleic acid, such as RNA or DNA, that bind tightly to a specific molecular target. See C. Tuerk and L. Gold. Systematic evolution of ligands by exponential enrichment: RNA ligands to bacteriophage T4 DNA polymerase, Science, 249:505-10, 1990. Like all nucleic acids, a particular aptamer may be described on paper by a linear sequence of nucleotides (A, U or T, C and G), typically 15-60 letters long. In the real world, however, the chain of nucleotides forms intramolecular interactions that fold the molecule into a complex three-dimensional shape. The shape of the aptamer allows it to bind tightly against the surface of its target molecule. The term "aptamer" derives from the Latin aptus, "to fit", and was chosen to emphasize this lock-and-key relationship between aptamers and their binding partners. Because an extraordinary diversity of molecular shapes exist within the universe of all possible nucleotide sequences, aptamers may be obtained for a wide array of molecular targets, including most proteins, such as HSS", "HSM" or "HSC" proteins (polypeptides) or fragments thereof.

Aptamers are generally used as a diagnostic—or prognostic, since it will yield information before symptoms arise—arrays of aptamers are bound to a solid support, and a body fluid sample applied. Unbound protein is washed off, and stains that tag proteins but not nucleic acids used to generate protein profiles. See E. N. Brody et al., "The use of aptamers in large arrays for molecular diagnostics," *Molecular Diagnostics*, 4:381-8, 1999.

Aptamers have therapeutic potential too because they block receptors and other protein activities. For example, an aptamer called NX1838, for example, that inhibits vascular endothelial growth factor (VEGF). NX1838 appears to function as an antagonist in an angiogenic disease model—excess blood vessels. The aptamer inhibits VEGF activity, binding it tightly, so that the protein cannot bind its receptor. In this manner, aptamers directed to or against HSS", "HSM" or "HSC" proteins (polypeptides) or fragments thereof can be generated that may inhibit the activity of these proteins and fragments in vitro and in vivo.

Aptamers are generally discovered through the SELEX method. See C. Tuerk and L. Gold. "Systematic evolution of ligands by exponential enrichment: RNA ligands to bacteriophage T4 DNA polymerase," Science, 249:505-10, 1990. SELEX is an iterative process used to identify an aptamer to a chosen molecular target. Since that time, it has been used to identify high-affinity aptamers against hundreds of targets.

The method relies on standard molecular biological techniques and can be carried out manually or in an automated fashion. The process can be broken down conceptually into four steps: (1) pool preparation, (2) selection, (3) amplification and (4) aptamer isolation.

a. Pool Preparation

To begin, a large "library" of nucleic acid molecules is generated. Each molecule in the library (often as many as $10^{15}$ different compounds) contains a unique nucleotide sequence that can, in principle, adopt a unique three-dimensional shape. A very few of these molecules—the aptamers—present a surface that is complementary to the target molecule.

b. Selection Partitioning

The selection step is designed to find those molecules with the greatest affinity for the target of interest. The library of nucleotide sequences is exposed to the target (a protein, small molecule, or supramolecular structure) and allowed to incubate for a period of time. The molecules in the library with weak or no affinity for the target will, on average, remain free in solution while those with some capacity to bind will tend to associate with it.

Any one of several methods is used to physically isolate the aptamer target complexes from the unbound molecules in the mixture, effectively separating the wheat from the chaff on a molecular scale. The unbound molecules are discarded. The target-bound molecules, among which are the highest affinity aptamers, are purified away from the target and used for the subsequent steps in the SELEX process.

c. Amplification

The captured, purified sequences are copied enzymatically, or "amplified", to generate a new library of molecules that is substantially enriched for those that can bind to the target. The enriched library is used to initiate a new cycle of selection, partitioning and amplification.

d. Aptamer Isolation

After 5-15 cycles of the complete process, the library of molecules is reduced from $10^{15}$ of unique sequences to a small number that bind tightly to the target of interest. Individual molecules in the mixture are then isolated, their nucleotide sequences are determined, and their properties with respect to binding affinity and specificity are measured and compared. In most cases, isolated aptamers are further refined to eliminate any nucleotides that do not contribute to target binding or aptamer structure. Aptamers truncated to their core binding domain typically range in length from 15 to 60 nucleotides. Using this process, it is possible to develop new aptamers in as little as two weeks. Experience over the past 10 years has shown that it is possible to select aptamers against virtually any molecular target, including proteins (acidic proteins, basic proteins, membrane proteins, enzymes . . . ), peptides, and is used to discover new aptamers.

The surface area of interaction between an aptamer and its molecular target is relatively large, so even small changes in the target molecule can disrupt aptamer association. Thus, aptamers can distinguish between closely related but non-identical members of a protein family, or between different functional or conformational states of the same protein. In a striking example of specificity, an aptamer to the small molecule theophylline (1,3-dimethylxanthine) binds with 10,000-fold lower affinity to caffeine (1,3,7-trimethylxanthine) that differs from theophylline by a single methyl group.

In addition to high specificity, aptamer have very high affinities to their targets. Typically aptamers generated against proteins have affinities in the picomolar to low nanomolar range. A representative set of aptamer-protein binding affinities is shown on the right.

Aptamers are chemically stable to all but the harshest environmental conditions and can be boiled or frozen without loss of activity. They may be produced on the benchtop using standard molecular biological techniques or they may be chemically synthesized at microgram to kilogram scales. As synthetic molecules, they are amenable to a nearly infinite variety of modifications designed to optimize their properties for a specific application. They may be circularized, linked together in pairs, or clustered onto the surface of a fat globule.

For in vivo applications, aptamers can be modified to dramatically reduce their sensitivity to degradation by enzymes in the blood. Other chemical appendages can alter their biodistribution or plasma residence time following intravenous injection. This plasticity is a distinct advantage of aptamers over other types of molecular ligands, such as monoclonal antibodies, where chemical modification is often variable, difficult to control, and may harm the function of the molecule.

XIV. Antisense Molecules RNAi Molecules

In accordance with the present invention, an antisense oligonucleotide is preferably an antisense oligonucleotide against at least 15 continuous nucleotides in the nucleotide sequence of SEQ ID NO: 5, 6, 7 or 8. The antisense oligonucleotide, which contains an initiation codon and is at least 15 continuous nucleotides, is even more preferred.

Derivatives or modified products of antisense oligonucleotides can be used as antisense oligonucleotides. Examples are, lower class alkyl phosphate modifications such as methyl-phosphonate-type or ethyl-phosphonate-type and phosphothioate or phosphoramidate.

The term "antisense oligonucleotides" as used herein means, not only those in which the nucleotides corresponding to those constituting a specified region of a DNA or mRNA are complementary, but also those having a mismatch of one or more nucleotides, as long as DNA or mRNA and an oligonucleotide can specifically hybridize with the nucleotide sequence of SEQ ID NO:5, 6, 7, or 8.

Such DNAs are indicated as those having, in the "at least 15 continuous nucleotide sequence region", a homology of at least 70% or higher, preferably at 80% or higher, more preferably 90% or higher, even more preferably 95% or higher to the nucleotide sequence of SEQ ID NO:5, 6, 7, or 8.

The antisense oligonucleotide derivative of the present invention, acts upon cells producing the protein of the invention by binding to the DNA or mRNA encoding the protein and inhibits its transcription or translation, promotes the degradation of the mRNA, inhibiting the expression of the proteins, polypeptides, or fragments thereof, of the invention resulting in the inhibition of function.

The antisense oligonucleotide derivative of the present invention can be made into an external preparation such as a liniment and a poultice by mixing with a suitable base material, which is inactive against the derivatives. Also, as needed, the derivatives can be formulated into tablets, powders, granules, capsules, liposome capsules, injections, solutions, nose-drops and freeze-drying agents by adding excipients, isotonic agents, dissolving auxiliaries, stabilizers, preservatives and pain-killers. These can be prepared using usual methods. The antisense oligonucleotide derivative is given to the patient by, directly applying onto the ailing site or by injecting into a blood vessel so that it will reach the site of ailment. An antisense-mounting medium can also be used to increase durability and membrane-permeability. Examples are, liposome, poly-L lysine, lipid, cholesterol, lipofectin or derivatives of these. The dosage of the antisense oligonucleotide derivative of the present invention can be adjusted suitably according to the patient's condition and used in desired amounts. For example, a dose range of 0.1 to 100 µg/kg, preferably 0.1 to 50 µg/kg can be administered.

Also included within the anti-sense embodiment of the present invention is RNAi molecules. RNAi (RNA interference) refers to the introduction of homologous double stranded RNA (dsRNA) to specifically target a gene's product, resulting in null or hypomorphic phenotypes. The use of antisense RNA to interfere with a gene's activity in C. elegans was first utilised by Su Guo and Ken Kemphues to study par-1; however, it has been reported that control sense RNA also produced apar-1 mutant phenotype (Cell 81: 611-20, 1995). Subsequently, it was discovered that it is the presence of dsRNA, formed from the annealing of sense and antisense strands present in the in vitro RNA preps, that is responsible for producing the interfering activity. Introduction of dsRNA into an adult worm results in the loss of the targeted endogenous mRNA from both the adult and its progeny. This phenomenon has been effectively harnessed to study an ever increasing number of maternal and zygotic genes in C. elegans.

The mechanism of how dsRNA results in the loss of the targeted homologous mRNA is as follows. A number of observations indicate that the primary interference effects are post-transcriptional. First it was observed that only dsRNA targeting exon sequences was effective (promoter and intron sequences could not produce an RNAi effect). Additional evidence supporting mature messages as the most likely target of RNA-mediated interference is described in et al. 1998, PNAS 95: 15502-07. Because RNAi is remarkably potent (i.e., only a few dsRNA molecules per cell are required to produce effective interference), the dsRNA must be either replicated and/or work catalytically. The current model favors a catalytic mechanism by which the dsRNA unwinds slightly, allowing the antisense strand to base pair with a short region of the target endogenous message and marking it for destruction. "Marking" mechanisms could involve covalent modification of the target (e.g. by adenosine deaminase) or any number of other mechanisms. Potentially, a single dsRNA molecule could mark hundreds of target mRNAs for destruction before it itself is "spent."

The broad scope of this invention is best understood with reference to the following examples, which are not intended to limit the invention to specific embodiments shown.

EXAMPLES

I. General Methods

Many of the standard methods below are described or referenced, e.g., in Maniatis, et al. (1982) Molecular Cloning, A Laboratory Manual Cold Spring Harbor Laboratory, Cold Spring Harbor Press, NY; Sambrook, et al. (1989) Molecular Cloning: A Laboratory Manual (2d ed.) Vols. 1-3, CSH Press, NY; Ausubel, et al., Biology Greene Publishing Associates, Brooklyn, N.Y.; or Ausubel, et al. (1987 and Supplements) Current Protocols in Molecular Biology Wiley/Greene, NY; Innis, et al. (eds.) (1990) PCR Protocols: A Guide to Methods and Applications Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," Methods in Enzymology vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, NY; Crowe, et al. (1992) QIAexpress: The High Level Expression & Protein Purification System QIAGEN, Inc., Chatsworth, Calif., and Coligan, et al. (eds.) (1995 and periodic supplements) Current Protocols in Protein Science, John Wiley and Sons, New York, N.Y.

Standard immunological techniques are described, e.g., in Coligan (1991) Current Protocols in Immunology Wiley/Greene, NY; and Methods in Enzymology volumes. 70, 73, 74, 84, 92, 93, 108, 116, 121, 132, 150, 162, and 163. Assays for neural cell biological activities are described, e.g., in Wouterlood (ed. 1995) Neuroscience Protocols modules 10, Elsevier; Methods in Neurosciences Academic Press; and Neuromethods Humana Press, Totowa, N.J. Methodology of developmental systems is described, e.g., in Meisami (ed.) Handbook of Human Growth and Developmental Biology CRC Press; and Chrispeels (ed.) Molecular Techniques and Approaches in Developmental Biology Interscience.

FACS analyses are described in Melamed, et al. (1990) Flow Cytometry and Sorting Wiley-Liss, Inc., New York, N.Y.; Shapiro (1988) Practical Flow Cytometry Liss, New York, N.Y.; and Robinson, et al. (1993) Handbook of Flow Cytometry Methods Wiley-Liss, New York, N.Y.

II. Isolation of HSS" and "HSM" Genes

HSS1 and HSM1, both human and mouse, are splice variants of the same locus (human locus ID=284361, mouse locus ID=69683). The two genes were discovered by analysis of the genes corresponding to Affymetrix probe 96320_at which covers the 3' untranslated region of Riken clone 2310044H10.

Primers for polymerase chain reaction were designed to amplify each splice variant. Products generated corresponded to the membrane bound form (HSM1) and secreted form (HSS1). The two forms are generated by alternative splicing of the seventh exon which is the last exon. The PCR and subsequent cloning and sequencing were done using mouse bone marrow lin– cDNA library and human testis cDNA library.

III. Vector Construction, Overexpression and Purification of HSS1

A subclone of the HSS1 gene was created from murine hematopoietic stem cells. The HSS1 gene was amplified from a murine cDNA library by PCR. PCR primers were designed to add EcoR I and Hind III cut sites (underlined below) at two terminal and a 6xHis (Histidine) tag was added at its C-terminal end. The following are the primers used to generate the subclone:

```
Forward primer:
5'CCGGAATTC GCCGTCCCTTCGCTGGTG3',

Reverse primer:
5'GGGAAGCTT TCA GTG GTG ATG ATG ATG ATG GGC CTC
CTG TGG CGG TGG CG3'.
```

The PCR amplication procedure was as follows: 94° C. 1 minute; 60° C. 1.5 minutes, 72° C. 1 minute. The amplified HSS1 cDNA was inserted into pTT3 vector between EcoR I and Hind III sites driven by a CMV promoter. This vector construct allows for high level of expression of proteins. See Durocher, et al., *High-level and high-throughput recombinant protein production by transient transfection of suspension-growing human 293-EBNA1 cells*, Nucleic Acids Res. 2002, Vol 30(2):E9.

The HSS1 cDNA construct was confirmed by restriction enzyme cut size and sequencing. The construct pTT3-HSS1 is transiently transfected into 293T cells to detect the expression level. Using the 6×His tag antibody, a Western blot analysis detected the presence of HSS1 in the cell lysate and also in the supernatant medium. From the Western blot analysis the molecular weight of HSF1 protein appeared to be about 30 kD.

FIG. 3 shows the results of the Western blot analysis. In this experiment, 293T cells harboring the HSS1 gene were grown in either serum free medium or serum supplemented medium, as indicated in the figure. 80-90% confluent 293T cells were transfected with 10 ug pTT or 10 ug pTT HSS1 using Lipofectamine Plus (Invitrogen, Carlsbad, Calif.). Serum, serum free supernatant and whole cell lysate were collected 24, 48 and 72 hours respectively post transfection. Cells were lysed in TNE Buffer (25 mM Tris-HCL, 150 mM NaCl, 5 mM EDTA, 1% Triton X-100 and protease inhibitors(Roche, Nutley, N.J.)).

10-20 ul volume of cell lysate and supernatants was used to detect HSS1 expression upon transfection. Samples were boiled in SDS buffer for 10' and loaded on 12% novex precast gels (Invitrogen, Carlsbad, Calif.). Membranes were blocked overnight in 3% BSA in 1×TBS. Primary antibody, Penta His Antibody (Qiagen, Valencia, Calif.), was used at a dilution of 1:2000 in 3% BSA in 1×TBS. Secondary antibody, goat anti mouse HRP (Santa Cruz Biotechnology, Santa Cruz, Calif.), was used at a dilution of 1:10,000 in 10% dry milk in 1 TBS. ECL plus (Ahmersham, Piscataway, N.J.) was used to detect signals.

From FIG. 3 it is observed that serum supplemented medium yields predominatly a higher molecular weight form of HSS1, which is most likely indicative of a fully processed, i.e., glycoslyated, form of the secreted protein embodiment of the present invention The 6×His tagged HSS1 protein can then be purified using nickel based column material. The histidine tag binds to the nickel column to yield relatively pure protein in one or more steps. The nickel based column materials can be purchased from InVitrogen and the manufacturers instructions are followed to yield purified HSS1. Other known purification techniques can also be used.

The above described vector construction, overexpression and purification methods can be used to generated any form of the polypeptides of the invention. For overexpression of the membrane-bound forms of the polypeptides of the invention, it is expected that the proteins will be found predominately in the cell lysate.

IV. Analysis of the Gylcoslyation States of HSS1

HSS1 has predicted glycosylation sites as described above. Glycosylation of the HSS1 protein was assessed by using a fusion protein with a His-6 tag at its carboxyl terminal as a marker. HSS1 was expressed in 293T cells. The results of this experiment are shown in FIG. 4.

Supernatant and cell lysate were collected and run on SDS-PAGE followed by western blot using anti-His6 antibodies. Prior to SDS-PAGE and western blot, samples were subjected to glycolytic digestion by three different enzymes either alone or together. Molecular weights determined by western blot of the various samples indicated multiple glycosylation states are present for HSS1. Cell lysate and supernatants from cells transfected with HSF1 were subjected to enzymatic de-glycosylation (Kit # GK80110) according to the manufacturer's recommendations (Prozyme, San Leandro, Calif.). Western blots were performed as described above.

V. Colony Forming Cell (CFC) Assay

A Colony Forming Cell (CFC) assay was performed using concentrated conditioned medium containing the His tagged form of HSS1, as described above. For the CFC analysis, a kit from Stem Cell Technologies, Inc. was used and the manufacturer's instructions were followed. The cells used in the CFC assay were $Lin^-$, $Sca^+$, $Kit^+$ hematopoietic cells. The cells were FACS purified from bone marrow. The hematopoietic cell population of Lin; $Sca^+$, $Kit^+$ hematopoietic cells contains progenitor cells and stem cells.

The CFC assay involves first mixing the $Lin^-$, $Sca^+$, $Kit^+$ hematopoietic cells at room temperature with methylcellulose that is provided in the Stem Cell Technologies kit. The cells are then plated and incubated at 37 deg C. for 12-14 days.

Figure 8:
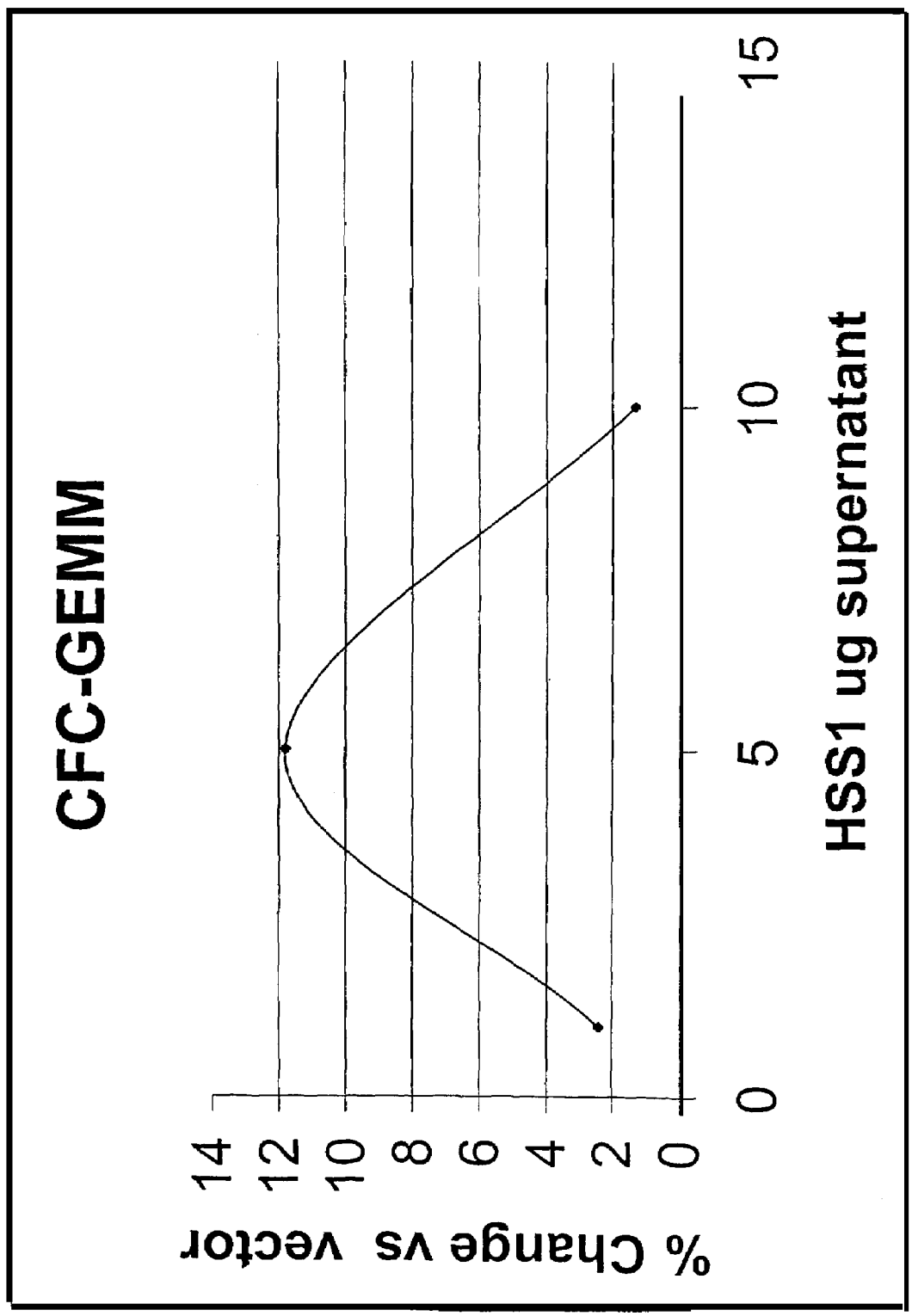
FIG. 8 shows the results of a CFC assay using hematopoietic progenitor/stem cells; as shown in the figure the more primitive colony population, i.e., GEMM colonies, are observed to preferentially expanded or increased as compared to total colony number.

The results of the CFC assay are shown in FIG. 8. Two concentrated supernatants from 293T cells, as described above, were used for the experiment. These supernatants are: 1) the supernatant containing HSS1 and 2) a control supernatant containing only the pTT vector. The points on the plot shown in FIG. 8 were generated from a ratio of the number of GEMM colonies as compared with the number of total colonies, which includes GEMM colonies for both HSS1 containing supernatant and vector only supernatant. The ratio of the HSS1 containing supernatant was then subtracted from the ratio obtained for the vector only supernatant. All plates also contained a panel of growth factors, namely 50 ng of SCF, 10 ng of IL-3, 10 ng IL-6 and 3 U/ml EPO.

As observed from inspection of FIG. 8, using 1 μg and 5 μg of HSS1 containing supernatant, it appears that GEMM colonies, which are a more primitive form of progenitor/stem cells that are revealed in the CFC assay, were preferentially expanded, or increased, as compared with the control vector containing supernatant. However, at higher levels of HSS1 containing supernatant, the reverse was observed, i.e., the total colonies were expanded preferentially relative to GEMM colonies. Thus, it appears that at lower concentrations of HSS1, GEMM colonies are preferentially expanded, or increased, relative to the number of total colonies, but at higher concentrations the effect became less specific. These observations suggest that HSS1 may play a role in expansion of primitive hematopoietic progenitor cells and stem cells. This role is consistent with the fact that the protein was first discovered in hematopoietic stem cells and appears to have a cytokine-like motif of at least two biological forms, namely a secreted form and its related membrane-bound splice variant.

VI. Monoclonal Antibody Production

Five 8-week male Balb/c mice are immunized 2 mg/head with aluminum hydroxide gel as the adjuvant, and 20 .mu.g/ head of a "HSS", "HSM" or "HSC" protein or the partial peptide as the antigen by injection into the peritoneal cavity. Re-immunization is done six times in every 2 weeks by injecting 20 μg/head of one of the above mentioned proteins or the partial peptides. After the 3.sup.rd immunization, blood is drawn from the eye-ground venous plexus and anti-"HSS", anti-"HSM" or anti-"HSC" antibody titer in the serum is examined.

Three days after the final immunization, spleen cells are prepared from mice, and used for cell fusion. $1 \times 10^8$ splenocytes from the immunized mice washed well with MEM (Nissui Pharmaceuticals), and murine myeloma P3-U 1.times.108 are mixed and centrifuged for 5 min at 1000 rpm. 2 g Polyethylene glycol-1500 (PEG-1500), and 2 ml MEM are added while mixing well at 37.degree. C. and centrifuged after 1 min at 600 rpm for 5 min. Further, 5 ml HBSS solution and 5 ml 20% FBS/MEM solution are added calmly, cells are suspended well, and centrifuged at 1000 rpm after 1 min, and the culture supernatant is discarded. The cells are re-suspended by adding 5 ml HAT medium (10–4M hypoxanthine, 4.times.10–7M aminopterin, and 1.5.times.10-SM thymidine supplemented medium). The cell suspension is seeded in 1 ml/well into a 24-well culture plate (Nunc), and cultivated for 24 hr in a CO.sub.2 incubator at 37.degree. C., 5% CO.sub.2, 95% air. 1 ml/well HAT medium is added and cultured further for another 24 hr. Then, 1 ml of culture supernatant is discarded, 1 ml HAT medium is newly added and cultivated further for another 12 days.

For those wells in which colonized fusion cells can be detected, 1 ml culture supernatant is discarded, 1 ml HAT medium (aminopterin-excluded, above-mentioned HAT medium) added and cultured at 37.degree. C. Exchange of the HAT medium is similarly done for the next two days and after culturing for 4 days, a portion of the culture supernatant is collected to measure the anti-"HSS", anti-"HSM" or anti-"HSC" antibody titer by ELISA.

For wells in which the antibody titer was detected, cloning is performed by limiting dilution twice more, and clones for which a stable antibody titer was detected, are selected as hybridomas producing anti-"HSS", anti-"HSM" or anti-"HSC" monoclonal antibodies.

A number of embodiments of the invention have been described. Nevertheless, it will be understood that various modifications may be made without departing from the spirit and scope of the invention. Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference to their entirety. As used herein, the term "comprise" and variations of the term, such as "comprising" "comprises" and "comprise," are not intended to exclude other additives, components integers or steps.

What is claimed is:

1. An isolated mammalian polypeptide comprising the sequence of SEQ ID NO: 1, or SEQ ID NO:21.

2. An isolated mammalian polypeptide encoded by the nucleic acid sequence of SEQ ID NO: 5.

3. A composition comprising the polypeptide of claim 1 and a pharmaceutically acceptable carrier.

4. An isolated polypeptide produced by a method comprising: (a) culturing an isolated recombinant host cell comprising a vector that comprises a nucleotide sequence encoding the polypeptide of claim 2 under conditions such that the polypeptide of claim 2 is expressed; and (b) recovering said polypeptide.

* * * * *

UNITED STATES PATENT AND TRADEMARK OFFICE
CERTIFICATE OF CORRECTION

PATENT NO. : 7,452,968 B2  Page 1 of 1
APPLICATION NO. : 10/541086
DATED : November 18, 2008
INVENTOR(S) : Timothy Kirk Gallaher et al.

It is certified that error appears in the above-identified patent and that said Letters Patent is hereby corrected as shown below:

Title page, Item (75) should read:

(75) Inventors: Timothy Kirk Gallaher, San Gabriel, CA (US); Lena A Basile ~~Bealle~~, Tujanga, CA (US); Kai-Jin Wu, Los Angeles, CA (US); Yi Zhao, South Pasadena, CA (US); Unnati Jariwata, Anaheim, CA (US)

Signed and Sealed this

Thirtieth Day of November, 2010

David J. Kappos
*Director of the United States Patent and Trademark Office*

SEQUENCE LISTING

<160> NUMBER OF SEQ ID NOS: 30

<210> SEQ ID NO 1
<211> LENGTH: 254
<212> TYPE: PRT
<213> ORGANISM: Homo sapiens

<400> SEQUENCE: 1

```
Met Ala Ala Ala Ser Ala Gly Ala Thr Arg Leu Leu Leu Leu Leu Leu
1               5                   10                  15

Met Ala Val Ala Ala Pro Ser Arg Ala Arg Gly Ser Gly Cys Arg Ala
            20                  25                  30

Gly Thr Gly Ala Arg Gly Ala Gly Ala Glu Gly Arg Glu Gly Glu Ala
        35                  40                  45

Cys Gly Thr Val Gly Leu Leu Leu Glu His Ser Phe Glu Ile Asp Asp
    50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95

Arg Leu Arg Asp Val Ala Ala Leu Asn Gly Leu Tyr Arg Val Arg Ile
            100                 105                 110

Pro Arg Arg Pro Gly Ala Leu Asp Gly Leu Glu Ala Gly Gly Tyr Val
        115                 120                 125

Ser Ser Phe Val Pro Ala Cys Ser Leu Val Glu Ser His Leu Ser Asp
    130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175
```

Asp Leu Glu Leu Phe Asn Thr Ser Val Gln Leu Gln Pro Thr Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys Tyr Trp His Ile Ile Leu Gly Gly Ala Val Leu Leu Thr Ala Leu
225                 230                 235                 240

Arg Pro Ala Ala Pro Gly Pro Ala Pro Pro Gln Glu Ala
                245                 250

<210> SEQ ID NO 2
<211> LENGTH: 254
<212> TYPE: PRT
<213> ORGANISM: Mus musculus

<400> SEQUENCE: 2

Met Val Ala Ala Gly Ala Gly Val Thr Arg Leu Leu Val Leu Leu Leu
1               5                   10                  15

Met Val Ala Ala Ala Pro Ser Arg Ala Arg Gly Ser Gly Cys Arg Val
            20                  25                  30

Gly Ala Ser Ala Arg Gly Thr Gly Ala Asp Gly Arg Glu Ala Glu Gly
        35                  40                  45

Cys Gly Thr Val Ala Leu Leu Leu Glu His Ser Phe Glu Leu Gly Asp
    50                  55                  60

Gly Ala Asn Phe Gln Lys Arg Gly Leu Leu Leu Trp Asn Gln Gln Asp
65                  70                  75                  80

Gly Thr Leu Ser Ala Thr Gln Arg Gln Leu Ser Glu Glu Glu Arg Gly
                85                  90                  95

Arg Leu Arg Asp Val Ala Ala Val Asn Gly Leu Tyr Arg Val Arg Val
            100                 105                 110

Pro Arg Arg Pro Gly Thr Leu Asp Gly Ser Glu Ala Gly Gly His Val
        115                 120                 125

Ser Ser Phe Val Pro Ala Cys Ser Leu Val Glu Ser His Leu Ser Asp
    130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Pro Ser Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys Tyr Trp His Leu Ile Leu Gly Gly Ala Val Leu Leu Thr Ala Leu
225                 230                 235                 240

Arg Pro Ala Ala Pro Gly Pro Ala Pro Ala Pro Thr Glu Ala
                245                 250

<210> SEQ ID NO 3
<211> LENGTH: 262
<212> TYPE: PRT
<213> ORGANISM: Homo sapiens

<400> SEQUENCE: 3

-continued

```
Met Ala Ala Ala Ser Ala Gly Ala Thr Arg Leu Leu Leu Leu Leu
1               5                   10                  15

Met Ala Val Ala Ala Pro Ser Arg Ala Arg Gly Ser Gly Cys Arg Ala
            20                  25                  30

Gly Thr Gly Ala Arg Gly Ala Gly Ala Glu Gly Arg Glu Gly Glu Ala
        35                  40                  45

Cys Gly Thr Val Gly Leu Leu Leu Glu His Ser Phe Glu Ile Asp Asp
    50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Arg Gly
            85                  90                  95

Arg Leu Arg Asp Val Ala Ala Leu Asn Gly Leu Tyr Arg Val Arg Ile
                100                 105                 110

Pro Arg Arg Pro Gly Ala Leu Asp Gly Leu Glu Ala Gly Gly Tyr Val
            115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys Tyr Trp Met Tyr Ile Ile Pro Val Val Leu Phe Leu Met Met Ser
225                 230                 235                 240

Gly Ala Pro Asp Ala Gly Gln Gly Gly Gly Gly Gly Gly Gly Gly Gly
            245                 250                 255

Gly Gly Gly Ser Gly Arg
            260

<210> SEQ ID NO 4
<211> LENGTH: 258
<212> TYPE: PRT
<213> ORGANISM: Mus musculus

<400> SEQUENCE: 4

Met Val Ala Ala Gly Ala Gly Val Thr Arg Leu Leu Val Leu Leu Leu
1               5                   10                  15

Met Val Ala Ala Ala Pro Ser Arg Ala Arg Gly Ser Gly Cys Arg Val
            20                  25                  30

Gly Ala Ser Ala Arg Gly Thr Gly Ala Asp Gly Arg Glu Ala Glu Gly
        35                  40                  45

Cys Gly Thr Val Ala Leu Leu Leu Glu His Ser Phe Glu Leu Gly Asp
    50                  55                  60

Gly Ala Asn Phe Gln Lys Arg Gly Leu Leu Leu Trp Asn Gln Gln Asp
65                  70                  75                  80

Gly Thr Leu Ser Ala Thr Gln Arg Gln Leu Ser Glu Glu Arg Gly
            85                  90                  95

Arg Leu Arg Asp Val Ala Ala Val Asn Gly Leu Tyr Arg Val Arg Val
```

```
              100                 105                 110
Pro Arg Arg Pro Gly Thr Leu Asp Gly Ser Glu Ala Gly Gly His Val
        115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Pro Ser Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys Tyr Trp Met Tyr Ile Ile Pro Val Val Leu Phe Leu Met Met Ser
225                 230                 235                 240

Gly Ala Pro Asp Ala Gly Gly Gln Gly Gly Gly Gly Gly Gly Gly Ser
                245                 250                 255

Ser Arg

<210> SEQ ID NO 5
<211> LENGTH: 1962
<212> TYPE: DNA
<213> ORGANISM: Homo sapiens
<220> FEATURE:
<221> NAME/KEY: CDS
<222> LOCATION: (47)..(811)

<400> SEQUENCE: 5
ggctcttggc tcacagccgt cccttcgctg gtgggaagaa gccgag atg gcg gca          55
                                                 Met Ala Ala
                                                   1 gcc agc gct ggg gca acc cgg ctg ctc ctg ctc ttg ctg atg gcg gta        103
Ala Ser Ala Gly Ala Thr Arg Leu Leu Leu Leu Leu Leu Met Ala Val
     5                  10                  15 gca gcg ccc agt cga gcc cgg ggc agc ggc tgc cgg gcc ggg act ggt        151
Ala Ala Pro Ser Arg Ala Arg Gly Ser Gly Cys Arg Ala Gly Thr Gly
 20                  25                  30                  35 gcg cga ggg gct ggg gcg gaa ggt cga gag ggc gag gcc tgt ggc acg        199
Ala Arg Gly Ala Gly Ala Glu Gly Arg Glu Gly Glu Ala Cys Gly Thr
                 40                  45                  50 gtg ggg ctg ctg ctg gag cac tca ttt gag atc gat gac agt gcc aac        247
Val Gly Leu Leu Leu Glu His Ser Phe Glu Ile Asp Asp Ser Ala Asn
             55                  60                  65 ttc cgg aag cgg ggc tca ctg ctc tgg aac cag cag gat ggt acc ttg        295
Phe Arg Lys Arg Gly Ser Leu Leu Trp Asn Gln Gln Asp Gly Thr Leu
         70                  75                  80 tcc ctg tca cag cgg cag ctc agc gag gag gag cgg ggc cga ctc cgg        343
Ser Leu Ser Gln Arg Gln Leu Ser Glu Glu Glu Arg Gly Arg Leu Arg
     85                  90                  95 gat gtg gca gcc ctg aat ggc ctg tac cgg gtc cgg atc cca agg cga        391
Asp Val Ala Ala Leu Asn Gly Leu Tyr Arg Val Arg Ile Pro Arg Arg
100                 105                 110                 115 ccc ggg gcc ctg gat ggc ctg gaa gct ggt ggc tat gtc tcc tcc ttt        439
Pro Gly Ala Leu Asp Gly Leu Glu Ala Gly Gly Tyr Val Ser Ser Phe
                 120                 125                 130 gtc cct gcg tgc tcc ctg gtg gag tcg cac ctg tcg gac cag ctg acc        487
```

```
                Val Pro Ala Cys Ser Leu Val Glu Ser His Leu Ser Asp Gln Leu Thr
                            135                 140                 145 ctg cac gtg gat gtg gcc ggc aac gtg gtg ggc gtg tcg gtg gtg acg        535
Leu His Val Asp Val Ala Gly Asn Val Val Gly Val Ser Val Val Thr
        150                 155                 160 cac cct ggg ggc tgc cgg ggc cat gag gtg gag gac gtg gac ctg gag        583
His Pro Gly Gly Cys Arg Gly His Glu Val Glu Asp Val Asp Leu Glu
        165                 170                 175 ctg ttc aac acc tcg gtg cag ctg cag ccg ccc acc aca gcc cca ggc        631
Leu Phe Asn Thr Ser Val Gln Leu Gln Pro Pro Thr Thr Ala Pro Gly
180                 185                 190                 195 cct gag acg gcg gcc ttc att gag cgc ctg gag atg gaa cag gcc cag        679
Pro Glu Thr Ala Ala Phe Ile Glu Arg Leu Glu Met Glu Gln Ala Gln
                200                 205                 210 aag gcc aag aac ccc cag gag cag aag tcc ttc ttc gcc aaa tac tgg        727
Lys Ala Lys Asn Pro Gln Glu Gln Lys Ser Phe Phe Ala Lys Tyr Trp
                215                 220                 225 cac atc atc ctg ggg ggg gcc gtg ttg ctc aca gcc ctg cgt cct gct        775
His Ile Ile Leu Gly Gly Ala Val Leu Leu Thr Ala Leu Arg Pro Ala
                230                 235                 240 gcg cca ggg ccc gcg cca ccg cca cag gag gcc tga tggatgtaca             821
Ala Pro Gly Pro Ala Pro Pro Gln Glu Ala
            245                 250
```
tcattcccgt cgtcctgttc ctcatgatgt caggagcgcc agacgccggg ggccagggtg        881
ggggtggggg tgggggtggt ggtgggggta gtggccggtg agggcccagg ctggtcagcg        941
tcccgtcttg cacacccagg ggcctccctt tctgctggag tccctgtgt cctcagccat       1001 cccaagaagg gtttgctagt ccctcctttc ccccgtccc acgaggccac ctgggccagc       1061
cccttgtcct ctgccttctg ctggcagagg agcagctgga ctggggcctt tggcacagca       1121
gccggtgtct cctgcgcccg cctcccccat ggccccatgc agcccaggg gcttccaccc       1181 tgcccatgga gtagagcccg agatcctggc cactatgcca gttctgacct cgcatccccc       1241
taccccgagc ccatgcagtc tgggaacatg ccgccttctc tccagcctct gtgcctttgt       1301
tccaggtggt ctcaccctcc tgtccctggc tgggctaggt ggtcctgtcc aggctcctgc       1361
agcgcccccc tcactttgac actggactag gatgcagcct cccttctgtg tccccttgag       1421
ggtaccctgg gtcccctcat caggggcaga ggcatgaaag agtcggggct ggatggccgg       1481
gggcttctgg gcccgatgcc tagtgcagcc actggggtcg tggtttgaca tttgtctgcc       1541
tggtgcaaac aaggaatcct tgcctttaag gtgacaggcc ctccacaggc ttccagactt       1601
gaaggaaaag gtttaagaaa gaaaacaaaa ccaacagtta gtggagtcaa agcccagaca       1661
ctgtaaatag aaccccctcc accaccccc gccgcccagc atcctacctg gactgcggtg       1721
ctacgagggc ctgcgggcct tgctgtgtg ccaccctccc tgtaagtcta tttaaaaaca       1781
tcgacgatac attgaaatgt gtgaacgttt tgaaaagcta cagcttccag cagccaaaag       1841
caactgttgt tttggcaaga cggtcctgat gtacaagctt gattgaaatt cactgctcac       1901
ttgatacgtt attcagaaac ccaaggaatg gctgtcccca tcctcatgtg gctgtgtgga       1961
g                                                                      1962

```
<210> SEQ ID NO 6
<211> LENGTH: 988
<212> TYPE: DNA
<213> ORGANISM: Mus musculus
<220> FEATURE:
<221> NAME/KEY: CDS
<222> LOCATION: (38)..(802)
```

<400> SEQUENCE: 6

```
gggctgtatg gctctcggtt tttctcaacg ctcccgt atg gtg gcc gcg ggt gcc         55
                                        Met Val Ala Ala Gly Ala
                                        1               5 ggg gtg acc cgg ctg cta gtg ctc ttg ctg atg gta gcc gcg gct cct         103
Gly Val Thr Arg Leu Leu Val Leu Leu Leu Met Val Ala Ala Ala Pro
        10                  15                  20 agc aga gcc cga ggc agc ggc tgc cgg gtc ggg gcc tcc gcg cgt ggg         151
Ser Arg Ala Arg Gly Ser Gly Cys Arg Val Gly Ala Ser Ala Arg Gly
    25                  30                  35 acc ggg gcc gat ggc cgt gaa gct gag ggc tgt ggc acc gtg gct ttg         199
Thr Gly Ala Asp Gly Arg Glu Ala Glu Gly Cys Gly Thr Val Ala Leu
40                  45                  50 ctg ctg gag cat tca ttt gag ctc ggt gat gga gcc aac ttc cag aag         247
Leu Leu Glu His Ser Phe Glu Leu Gly Asp Gly Ala Asn Phe Gln Lys
55                  60                  65                  70 cga ggc ttg ctg ctc tgg aac cag cag gat ggc acc ctg tcg gca aca         295
Arg Gly Leu Leu Leu Trp Asn Gln Gln Asp Gly Thr Leu Ser Ala Thr
            75                  80                  85 cag cga cag ctc agt gag gag gag cgt ggc cga ctc cgg gat gtg gct         343
Gln Arg Gln Leu Ser Glu Glu Glu Arg Gly Arg Leu Arg Asp Val Ala
        90                  95                  100 gct gtc aat ggc ctc tac agg gtc cgg gtc ccg agg cgg cct ggg aca         391
Ala Val Asn Gly Leu Tyr Arg Val Arg Val Pro Arg Arg Pro Gly Thr
    105                 110                 115 ctt gat ggt tca gaa gct ggc ggc cat gtg tct tcc ttc gtc cca gcg         439
Leu Asp Gly Ser Glu Ala Gly Gly His Val Ser Ser Phe Val Pro Ala
120                 125                 130 tgc tcc ctg gtg gag tcg cac ctt tcg gac cag ctg acc ttg cac gtg         487
Cys Ser Leu Val Glu Ser His Leu Ser Asp Gln Leu Thr Leu His Val
135                 140                 145                 150 gat gtg gct ggc aac gtg gtg ggc ctg tct gtg gtg gtg tac cct ggg         535
Asp Val Ala Gly Asn Val Val Gly Leu Ser Val Val Val Tyr Pro Gly
            155                 160                 165 ggc tgc cgg ggc tcc gag gtg gaa gat gag gac ctg gag ctg ttc aat         583
Gly Cys Arg Gly Ser Glu Val Glu Asp Glu Asp Leu Glu Leu Phe Asn
        170                 175                 180 aca tct gtg cag ctg cgg cct ccc agc act gct cca ggc ccc gag act         631
Thr Ser Val Gln Leu Arg Pro Pro Ser Thr Ala Pro Gly Pro Glu Thr
    185                 190                 195 gca gcc ttc att gag cgc ctg gag atg gag cag gcc cag aag gcc aag         679
Ala Ala Phe Ile Glu Arg Leu Glu Met Glu Gln Ala Gln Lys Ala Lys
200                 205                 210 aac cca cag gag cag aag tct ttc ttt gcc aaa tac tgg cac ctc atc         727
Asn Pro Gln Glu Gln Lys Ser Phe Phe Ala Lys Tyr Trp His Leu Ile
215                 220                 225                 230 ctg ggg ggg gcc gtg ttg ctc aca gcc cta cgt cct gct gcc cca ggg         775
Leu Gly Gly Ala Val Leu Leu Thr Ala Leu Arg Pro Ala Ala Pro Gly
            235                 240                 245 cct gca cca gcg cca acg gag gcc taa gtgaggacac agtcccctgc              822
Pro Ala Pro Ala Pro Thr Glu Ala
            250 ccgccttgcc ctctgccat gccctcctgt ccctcctgtc ccctgccctg gccctgcctg       882 tagtgactag gggacccagc ccctccctc tgtggccctg gccctgggcc atcctcatca       942 cttacctccc ttcctctctg cctgtctctg tgtccacctg tcctgc                    988
```

<210> SEQ ID NO 7

<211> LENGTH: 1875
<212> TYPE: DNA
<213> ORGANISM: Homo sapiens
<220> FEATURE:
<221> NAME/KEY: CDS
<222> LOCATION: (47)..(835)

<400> SEQUENCE: 7

```
ggctcttggc tcacagccgt cccttcgctg gtgggaagaa gccgag atg gcg gca         55
                                                 Met Ala Ala
                                                   1 gcc agc gct ggg gca acc cgg ctg ctc ctg ctc ttg ctg atg gcg gta       103
Ala Ser Ala Gly Ala Thr Arg Leu Leu Leu Leu Leu Leu Met Ala Val
  5                  10                  15 gca gcg ccc agt cga gcc cgg ggc agc ggc tgc cgg gcc ggg act ggt       151
Ala Ala Pro Ser Arg Ala Arg Gly Ser Gly Cys Arg Ala Gly Thr Gly
 20                  25                  30                  35 gcg cga ggg gct ggg gcg gaa ggt cga gag ggc gag gcc tgt ggc acg       199
Ala Arg Gly Ala Gly Ala Glu Gly Arg Glu Gly Glu Ala Cys Gly Thr
                 40                  45                  50 gtg ggg ctg ctg ctg gag cac tca ttt gag atc gat gac agt gcc aac       247
Val Gly Leu Leu Leu Glu His Ser Phe Glu Ile Asp Asp Ser Ala Asn
 55                  60                  65 ttc cgg aag cgg ggc tca ctg ctc tgg aac cag cag gat ggt acc ttg       295
Phe Arg Lys Arg Gly Ser Leu Leu Trp Asn Gln Gln Asp Gly Thr Leu
         70                  75                  80 tcc ctg tca cag cgg cag ctc agc gag gag gag cgg ggc cga ctc cgg       343
Ser Leu Ser Gln Arg Gln Leu Ser Glu Glu Glu Arg Gly Arg Leu Arg
 85                  90                  95 gat gtg gca gcc ctg aat ggc ctg tac cgg gtc cgg atc cca agg cga       391
Asp Val Ala Ala Leu Asn Gly Leu Tyr Arg Val Arg Ile Pro Arg Arg
100                 105                 110                 115 ccc ggg gcc ctg gat ggc ctg gaa gct ggt ggc tat gtc tcc tcc ttt       439
Pro Gly Ala Leu Asp Gly Leu Glu Ala Gly Gly Tyr Val Ser Ser Phe
                120                 125                 130 gtc cct gcg tgc tcc ctg gtg gag tcg cac ctg tcg gac cag ctg acc       487
Val Pro Ala Cys Ser Leu Val Glu Ser His Leu Ser Asp Gln Leu Thr
            135                 140                 145 ctg cac gtg gat gtg gcc ggc aac gtg gtg ggc gtg tcg gtg gtg acg       535
Leu His Val Asp Val Ala Gly Asn Val Val Gly Val Ser Val Val Thr
        150                 155                 160 cac cct ggg ggc tgc cgg ggc cat gag gtg gag gac gtg gac ctg gag       583
His Pro Gly Gly Cys Arg Gly His Glu Val Glu Asp Val Asp Leu Glu
    165                 170                 175 ctg ttc aac acc tcg gtg cag ctg cag ccg ccc acc aca gcc cca ggc       631
Leu Phe Asn Thr Ser Val Gln Leu Gln Pro Pro Thr Thr Ala Pro Gly
180                 185                 190                 195 cct gag acg gcg gcc ttc att gag cgc ctg gag atg gaa cag gcc cag       679
Pro Glu Thr Ala Ala Phe Ile Glu Arg Leu Glu Met Glu Gln Ala Gln
                200                 205                 210 aag gcc aag aac ccc cag gag cag aag tcc ttc ttc gcc aaa tac tgg       727
Lys Ala Lys Asn Pro Gln Glu Gln Lys Ser Phe Phe Ala Lys Tyr Trp
            215                 220                 225 atg tac atc att ccc gtc gtc ctg ttc ctc atg atg tca gga gcg cca       775
Met Tyr Ile Ile Pro Val Val Leu Phe Leu Met Met Ser Gly Ala Pro
        230                 235                 240 gac acc ggg ggc cag ggt ggg ggt ggg ggt ggt ggt ggg ggt               823
Asp Thr Gly Gly Gln Gly Gly Gly Gly Gly Gly Gly Gly Gly
    245                 250                 255 agt ggc cgg tga gggcccaggc tggtcagcgt cccgtcttgc acacccaggg           875
Ser Gly Arg
```

-continued

```
260 gcctcccttt ctgctggagt ccctgtgtc ctcagccatc caagaaggg tttgctggtc      935 cctcctttcc ccccgtccca cgaggccacc tgggccagcc ccttgtcctc tgccttctgc    995 tggcagagga gcagctggac tggggccttt ggcacagcag ccggtgtctc ctgcgcccgc    1055 ctcccccatg gccccatgca gccccagggg cttcccccct gcccatggag tagagcccga    1115 gatcctggcc actatgccag ttctgacctc gcatccccct accccgagcc catgcagtct    1175 gggaacatgc cgccttctct ccagcctctg tgcctttgtt ccaggtggtc tcaccctcct    1235 gtccctggct gggctaggtg gtcctgtcca ggctcctgca gcgccccct cactttgaca     1295 ctggactagg atgcagcctc ccttctgtgt cccttgagg gtaccctggg tcccctcatc     1355 aggggcagag gcatgaaaga gtcggggctg gatggccggg ggcttctggg cccgacgcct    1415 agtgcagccc ctggggtcgt ggtttgacat ttgtctgcct ggtgcaaaca aggaatcctt    1475 gcctttaagg tgacaggccc tccacaggct tccagacttg aaggaaaagg tttaagaaag    1535 aaaacaaaac caacagttag tggagtcaaa gcccagacac tgtaaataga accccctcca    1595 ccacccccg ccgcccagca tcctacctgg actgcggtgc tacagagggcc tgcgggcctt    1655 tgctgtgtgc cacctcct gtaagtctat ttaaaaacat cgacgataca ttgaaatgtg      1715 tgaacgtttt gaaagctac agcttccagc agccaaaagc aactgttgtt ttggcaagac     1775 ggtcctgatg tacaagcttg attgaaattc actgctcact tgatacgtta ttcagaaacc    1835 caaggaatgg ctgtccccat cctcatgtgg ctgtgtggag                          1875
```

<210> SEQ ID NO 8
<211> LENGTH: 1540
<212> TYPE: DNA
<213> ORGANISM: Mus musculus
<220> FEATURE:
<221> NAME/KEY: CDS
<222> LOCATION: (38)..(814)

<400> SEQUENCE: 8

```
gggctgtatg gctctcggtt tttctcaacg ctcccgt atg gtg gcc gcg ggt gcc     55
                                         Met Val Ala Ala Gly Ala
                                          1               5 ggg gtg acc cgg ctg cta gtg ctc ttg ctg atg gta gcc gcg gct cct      103
Gly Val Thr Arg Leu Leu Val Leu Leu Leu Met Val Ala Ala Ala Pro
         10                  15                  20 agc aga gcc cga ggc agc ggc tgc cgg gtc ggg gcc tcc gcg cgt ggg      151
Ser Arg Ala Arg Gly Ser Gly Cys Arg Val Gly Ala Ser Ala Arg Gly
     25                  30                  35 acc ggg gcc gat ggc cgt gaa gct gag ggc tgt ggc acc gtg gct ttg      199
Thr Gly Ala Asp Gly Arg Glu Ala Glu Gly Cys Gly Thr Val Ala Leu
 40                  45                  50 ctg ctg gag cat tca ttt gag ctc ggt gat gga gcc aac ttc cag aag      247
Leu Leu Glu His Ser Phe Glu Leu Gly Asp Gly Ala Asn Phe Gln Lys
55                  60                  65                  70 cga ggc ttg ctg ctc tgg aac cag cag gat ggc acc ctg tcg gca aca      295
Arg Gly Leu Leu Leu Trp Asn Gln Gln Asp Gly Thr Leu Ser Ala Thr
                 75                  80                  85 cag cga cag ctc agt gag gag gag cgt ggc cga ctc cgg gat gtg gct      343
Gln Arg Gln Leu Ser Glu Glu Glu Arg Gly Arg Leu Arg Asp Val Ala
         90                  95                 100 gct gtc aat ggc ctc tac agg gtc cgg gtc ccg agg cgg cct ggg aca      391
Ala Val Asn Gly Leu Tyr Arg Val Arg Val Pro Arg Arg Pro Gly Thr
    105                 110                 115
```

| | | | | | | | | | | | | | | | | |
|---|---|---|---|---|---|---|---|---|---|---|---|---|---|---|---|---|
| ctt | gat | ggt | tca | gaa | gct | ggc | ggc | cat | gtg | tct | tcc | ttc | gtc | cca | gcg | 439 |
| Leu | Asp | Gly | Ser | Glu | Ala | Gly | Gly | His | Val | Ser | Ser | Phe | Val | Pro | Ala | |
| | 120 | | | | 125 | | | | 130 | | | | | | | |
| tgc | tcc | ctg | gtg | gag | tcg | cac | ctt | tcg | gac | cag | ctg | acc | ttg | cac | gtg | 487 |
| Cys | Ser | Leu | Val | Glu | Ser | His | Leu | Ser | Asp | Gln | Leu | Thr | Leu | His | Val | |
| 135 | | | | | 140 | | | | 145 | | | | | 150 | | |
| gat | gtg | gct | ggc | aac | gtg | gtg | ggc | ctg | tct | gtg | gtg | gtg | tac | cct | ggg | 535 |
| Asp | Val | Ala | Gly | Asn | Val | Val | Gly | Leu | Ser | Val | Val | Val | Tyr | Pro | Gly | |
| | | | | 155 | | | | | 160 | | | | | 165 | | |
| ggc | tgc | cgg | ggc | tcc | gag | gtg | gaa | gat | gag | gac | ctg | gag | ctg | ttc | aat | 583 |
| Gly | Cys | Arg | Gly | Ser | Glu | Val | Glu | Asp | Glu | Asp | Leu | Glu | Leu | Phe | Asn | |
| | | | 170 | | | | | 175 | | | | | 180 | | | |
| aca | tct | gtg | cag | ctg | cgg | cct | ccc | agc | act | gct | cca | ggc | ccc | gag | act | 631 |
| Thr | Ser | Val | Gln | Leu | Arg | Pro | Pro | Ser | Thr | Ala | Pro | Gly | Pro | Glu | Thr | |
| | | 185 | | | | | 190 | | | | | 195 | | | | |
| gca | gcc | ttc | att | gag | cgc | ctg | gag | atg | gag | cag | gcc | cag | aag | gcc | aag | 679 |
| Ala | Ala | Phe | Ile | Glu | Arg | Leu | Glu | Met | Glu | Gln | Ala | Gln | Lys | Ala | Lys | |
| | 200 | | | | 205 | | | | 210 | | | | | | | |
| aac | cca | cag | gag | cag | aag | tct | ttc | ttt | gcc | aaa | tac | tgg | atg | tac | atc | 727 |
| Asn | Pro | Gln | Glu | Gln | Lys | Ser | Phe | Phe | Ala | Lys | Tyr | Trp | Met | Tyr | Ile | |
| 215 | | | | | 220 | | | | 225 | | | | | 230 | | |
| att | cca | gtt | gtg | ctg | ttc | ctc | atg | atg | tcg | gga | gcg | ccg | gac | gct | ggg | 775 |
| Ile | Pro | Val | Val | Leu | Phe | Leu | Met | Met | Ser | Gly | Ala | Pro | Asp | Ala | Gly | |
| | | | | 235 | | | | | 240 | | | | | 245 | | |
| ggc | cag | ggc | ggc | ggt | ggg | ggc | ggg | ggc | agc | agc | cgg | tga | gcagctgtgc | | | 824 |
| Gly | Gln | Gly | Gly | Gly | Gly | Gly | Gly | Gly | Ser | Ser | Arg | | | | | |
| | | | 250 | | | | | 255 | | | | | | | | |

| | |
|---|---|
| cacctagagc ccccccagga gccagcccaa gaaggagttc ctgtcccac atttccctat | 884 |
| tgcatgaata tggaaggctg tcccttcagt gagccctctg gccttcctgt aagcccctct | 944 |
| ttctgtccct gagcctctct ctcatcctgt tgactgagag cttgggtgga cctccctgta | 1004 |
| gccagctcac tgcaactgtg tcccaccatg tggcactgtg ctcctctgtc tgctaaacac | 1064 |
| ccaccagcct gccccacccc accccaccat acactttggg aacttgccaa gctctctcca | 1124 |
| gcctctgtgc ctttgccctg caggcccccgt gcgcccctca ctgtcactct ccagcccttt | 1184 |
| gccaaggatc tgtgcccag aggcctctgc tcttagtggc taggtcagcc tccagcccac | 1244 |
| tgtccaggtg gcatgctgtc ttctttgccc ccctctctgg tgcccagaa taccatggtg | 1304 |
| acctaccact atcctttctg cctttggatg tcatagcctg gatctgtcac caggagagga | 1364 |
| ttgtgggcct ccacgttagt ctgtgaatgc acacttcgag tgacttgtgt gcaggttttg | 1424 |
| agagccggtt ttgcactagc tgctcgacag ctgctggcat ggccgtgctc ttgcacatgc | 1484 |
| gccgctgtgg gcatggggat tgctgtgcag cctcagctgt gttgtgtggc tgctga | 1540 |

<210> SEQ ID NO 9
<211> LENGTH: 227
<212> TYPE: PRT
<213> ORGANISM: Homo sapiens

<400> SEQUENCE: 9

Met Ala Ala Ala Ser Ala Gly Ala Thr Arg Leu Leu Leu Leu Leu
1               5                   10                  15

Met Ala Val Ala Ala Pro Ser Arg Ala Arg Gly Ser Gly Cys Arg Ala
                20                  25                  30

Gly Thr Gly Ala Arg Gly Ala Gly Ala Glu Gly Arg Glu Gly Glu Ala
            35                  40                  45

Cys Gly Thr Val Gly Leu Leu Leu Glu His Ser Phe Glu Ile Asp Asp
        50                  55                  60

```
Ser Ala Asn Phe Arg Lys Arg Gly Ser Leu Leu Trp Asn Gln Gln Asp
 65                  70                  75                  80

Gly Thr Leu Ser Leu Ser Gln Arg Gln Leu Ser Glu Glu Arg Gly
                 85                  90                  95

Arg Leu Arg Asp Val Ala Ala Leu Asn Gly Leu Tyr Arg Val Arg Ile
                100                 105                 110

Pro Arg Arg Pro Gly Ala Leu Asp Gly Leu Glu Ala Gly Gly Tyr Val
                115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Thr Thr
                180                 185                 190

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser Phe Phe Ala
210                 215                 220

Lys Tyr Trp
225

<210> SEQ ID NO 10
<211> LENGTH: 227
<212> TYPE: PRT
<213> ORGANISM: Mus musculus

<400> SEQUENCE: 10

Met Val Ala Ala Gly Ala Gly Val Thr Arg Leu Leu Val Leu Leu Leu
 1               5                  10                  15

Met Val Ala Ala Ala Pro Ser Arg Ala Arg Gly Ser Gly Cys Arg Val
                20                  25                  30

Gly Ala Ser Ala Arg Gly Thr Gly Ala Asp Gly Arg Glu Ala Glu Gly
             35                  40                  45

Cys Gly Thr Val Ala Leu Leu Leu Glu His Ser Phe Glu Leu Gly Asp
 50                  55                  60

Gly Ala Asn Phe Gln Lys Arg Gly Leu Leu Leu Trp Asn Gln Gln Asp
 65                  70                  75                  80

Gly Thr Leu Ser Ala Thr Gln Arg Gln Leu Ser Glu Glu Arg Gly
                 85                  90                  95

Arg Leu Arg Asp Val Ala Ala Val Asn Gly Leu Tyr Arg Val Arg Val
                100                 105                 110

Pro Arg Arg Pro Gly Thr Leu Asp Gly Ser Glu Ala Gly Gly His Val
                115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Ser Thr
                180                 185                 190

Ala Pro Gly Pro Glu Thr Ala Ala Phe Ile Glu Arg Leu Glu Met Glu
```

-continued

```
                195                 200                 205
Gln Ala Gln Lys Ala Lys Asn Pro Gln Glu Gln Lys Ser Phe Phe Ala
    210                 215                 220
Lys Tyr Trp
225

<210> SEQ ID NO 11
<211> LENGTH: 730
<212> TYPE: DNA
<213> ORGANISM: Homo sapiens
<220> FEATURE:
<221> NAME/KEY: CDS
<222> LOCATION: (47)..(730)

<400> SEQUENCE: 11
ggctcttggc tcacagccgt cccttcgctg gtgggaagaa gccgag atg gcg gca         55
                                                Met Ala Ala
                                                  1 gcc agc gct ggg gca acc cgg ctg ctc ctg ctc ttg ctg atg gcg gta       103
Ala Ser Ala Gly Ala Thr Arg Leu Leu Leu Leu Leu Leu Met Ala Val
      5                  10                  15 gca gcg ccc agt cga gcc cgg ggc agc ggc tgc cgg gcc ggg act ggt       151
Ala Ala Pro Ser Arg Ala Arg Gly Ser Gly Cys Arg Ala Gly Thr Gly
 20                  25                  30                  35 gcg cga ggg gct ggg gcg gaa ggt cga gag ggc gag gcc tgt ggc acg       199
Ala Arg Gly Ala Gly Ala Glu Gly Arg Glu Gly Glu Ala Cys Gly Thr
                 40                  45                  50 gtg ggg ctg ctg ctg gag cac tca ttt gag atc gat gac agt gcc aac       247
Val Gly Leu Leu Leu Glu His Ser Phe Glu Ile Asp Asp Ser Ala Asn
             55                  60                  65 ttc cgg aag cgg ggc tca ctg ctc tgg aac cag cag gat ggt acc ttg       295
Phe Arg Lys Arg Gly Ser Leu Leu Trp Asn Gln Gln Asp Gly Thr Leu
         70                  75                  80 tcc ctg tca cag cgg cag ctc agc gag gag gag cgg ggc cga ctc cgg       343
Ser Leu Ser Gln Arg Gln Leu Ser Glu Glu Glu Arg Gly Arg Leu Arg
     85                  90                  95 gat gtg gca gcc ctg aat ggc ctg tac cgg gtc cgg atc cca agg cga       391
Asp Val Ala Ala Leu Asn Gly Leu Tyr Arg Val Arg Ile Pro Arg Arg
100                 105                 110                 115 ccc ggg gcc ctg gat ggc ctg gaa gct ggt ggc tat gtc tcc tcc ttt       439
Pro Gly Ala Leu Asp Gly Leu Glu Ala Gly Gly Tyr Val Ser Ser Phe
                120                 125                 130 gtc cct gcg tgc tcc ctg gtg gag tcg cac ctg tcg gac cag ctg acc       487
Val Pro Ala Cys Ser Leu Val Glu Ser His Leu Ser Asp Gln Leu Thr
            135                 140                 145 ctg cac gtg gat gtg gcc ggc aac gtg gtg ggc gtg tcg gtg gtg acg       535
Leu His Val Asp Val Ala Gly Asn Val Val Gly Val Ser Val Val Thr
        150                 155                 160 cac cct ggg ggc tgc cgg ggc cat gag gtg gag gac gtg gac ctg gag       583
His Pro Gly Gly Cys Arg Gly His Glu Val Glu Asp Val Asp Leu Glu
    165                 170                 175 ctg ttc aac acc tcg gtg cag ctg cag ccg ccc acc aca gcc cca ggc       631
Leu Phe Asn Thr Ser Val Gln Leu Gln Pro Pro Thr Thr Ala Pro Gly
180                 185                 190                 195 cct gag acg gcg gcc ttc att gag cgc ctg gag atg gaa cag gcc cag       679
Pro Glu Thr Ala Ala Phe Ile Glu Arg Leu Glu Met Glu Gln Ala Gln
                200                 205                 210 aag gcc aag aac ccc cag gag cag aag tcc ttc ttc gcc aaa tac tgg       727
Lys Ala Lys Asn Pro Gln Glu Gln Lys Ser Phe Phe Ala Lys Tyr Trp
            215                 220                 225
```

```
<210> SEQ ID NO 12
<211> LENGTH: 721
<212> TYPE: DNA
<213> ORGANISM: Mus musculus
<220> FEATURE:
<221> NAME/KEY: CDS
<222> LOCATION: (38)..(721)

<400> SEQUENCE: 12
```

| | | |
|---|---|---|
| gggctgtatg gctctcggtt tttctcaacg ctcccgt atg gtg gcc gcg ggt gcc<br>                       Met Val Ala Ala Gly Ala<br>                        1       5 | | 55 |
| ggg gtg acc cgg ctg cta gtg ctc ttg ctg atg gta gcc gcg gct cct<br>Gly Val Thr Arg Leu Leu Val Leu Leu Leu Met Val Ala Ala Ala Pro<br>      10         15         20 | | 103 |
| agc aga gcc cga ggc agc ggc tgc cgg gtc ggg gcc tcc gcg cgt ggg<br>Ser Arg Ala Arg Gly Ser Gly Cys Arg Val Gly Ala Ser Ala Arg Gly<br>  25         30         35 | | 151 |
| acc ggg gcc gat ggc cgt gaa gct gag ggc tgt ggc acc gtg gct ttg<br>Thr Gly Ala Asp Gly Arg Glu Ala Glu Gly Cys Gly Thr Val Ala Leu<br>40         45         50 | | 199 |
| ctg ctg gag cat tca ttt gag ctc ggt gat gga gcc aac ttc cag aag<br>Leu Leu Glu His Ser Phe Glu Leu Gly Asp Gly Ala Asn Phe Gln Lys<br>55         60         65         70 | | 247 |
| cga ggc ttg ctg ctc tgg aac cag cag gat ggc acc ctg tcg gca aca<br>Arg Gly Leu Leu Leu Trp Asn Gln Gln Asp Gly Thr Leu Ser Ala Thr<br>      75         80         85 | | 295 |
| cag cga cag ctc agt gag gag gag cgt ggc cga ctc cgg gat gtg gct<br>Gln Arg Gln Leu Ser Glu Glu Glu Arg Gly Arg Leu Arg Asp Val Ala<br>  90         95         100 | | 343 |
| gct gtc aat ggc ctc tac agg gtc cgg gtc ccg agg cgg cct ggg aca<br>Ala Val Asn Gly Leu Tyr Arg Val Arg Val Pro Arg Arg Pro Gly Thr<br>105         110         115 | | 391 |
| ctt gat ggt tca gaa gct ggc ggc cat gtg tct tcc ttc gtc cca gcg<br>Leu Asp Gly Ser Glu Ala Gly Gly His Val Ser Ser Phe Val Pro Ala<br>120         125         130 | | 439 |
| tgc tcc ctg gtg gag tcg cac ctt tcg gac cag ctg acc ttg cac gtg<br>Cys Ser Leu Val Glu Ser His Leu Ser Asp Gln Leu Thr Leu His Val<br>135         140         145         150 | | 487 |
| gat gtg gct ggc aac gtg gtg ggc ctg tct gtg gtg tac cct ggg<br>Asp Val Ala Gly Asn Val Val Gly Leu Ser Val Val Tyr Pro Gly<br>         155         160         165 | | 535 |
| ggc tgc cgg ggc tcc gag gtg gaa gat gag gac ctg gag ctg ttc aat<br>Gly Cys Arg Gly Ser Glu Val Glu Asp Glu Asp Leu Glu Leu Phe Asn<br>      170         175         180 | | 583 |
| aca tct gtg cag ctg cgg cct ccc agc act gct cca ggc ccc gag act<br>Thr Ser Val Gln Leu Arg Pro Pro Ser Thr Ala Pro Gly Pro Glu Thr<br>  185        190         195 | | 631 |
| gca gcc ttc att gag cgc ctg gag atg gag cag gcc cag aag gcc aag<br>Ala Ala Phe Ile Glu Arg Leu Glu Met Glu Gln Ala Gln Lys Ala Lys<br>200         205         210 | | 679 |
| aac cca cag gag cag aag tct ttc ttt gcc aaa tac tgg tga<br>Asn Pro Gln Glu Gln Lys Ser Phe Phe Ala Lys Tyr Trp<br>215         220         225 | | 721 |

```
<210> SEQ ID NO 13
<211> LENGTH: 225
<212> TYPE: PRT
<213> ORGANISM: Homo sapiens
```

```
<400> SEQUENCE: 13

Met Ala Ala Ala Ser Ala Gly Ala Thr Arg Leu Leu Leu Leu Leu Leu
1               5                   10                  15

Met Ala Val Ala Ala Pro Ser Arg Ala Arg Gly Ser Gly Cys Arg Ala
            20                  25                  30

Gly Thr Gly Ala Arg Gly Ala Gly Ala Glu Gly Arg Glu Gly Glu Ala
        35                  40                  45

Cys Gly Thr Val Gly Leu Leu Leu Glu His Ser Phe Glu Ile Asp Asp
    50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95

Arg Leu Arg Asp Val Ala Ala Leu Asn Gly Leu Tyr Arg Val Arg Ile
            100                 105                 110

Pro Arg Arg Pro Gly Ala Leu Asp Gly Leu Glu Ala Gly Gly Tyr Val
        115                 120                 125

Ser Ser Phe Val Pro Ala Cys Ser Leu Val Glu Ser His Leu Ser Asp
    130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
    210                 215                 220

Lys
225

<210> SEQ ID NO 14
<211> LENGTH: 225
<212> TYPE: PRT
<213> ORGANISM: Mus musculus

<400> SEQUENCE: 14

Met Val Ala Ala Gly Ala Gly Val Thr Arg Leu Leu Val Leu Leu Leu
1               5                   10                  15

Met Val Ala Ala Ala Pro Ser Arg Ala Arg Gly Ser Gly Cys Arg Val
            20                  25                  30

Gly Ala Ser Ala Arg Gly Thr Gly Ala Asp Gly Arg Glu Ala Glu Gly
        35                  40                  45

Cys Gly Thr Val Ala Leu Leu Leu Glu His Ser Phe Glu Leu Gly Asp
    50                  55                  60

Gly Ala Asn Phe Gln Lys Arg Gly Leu Leu Leu Trp Asn Gln Gln Asp
65                  70                  75                  80

Gly Thr Leu Ser Ala Thr Gln Arg Gln Leu Ser Glu Glu Glu Arg Gly
                85                  90                  95

Arg Leu Arg Asp Val Ala Ala Val Asn Gly Leu Tyr Arg Val Arg Val
            100                 105                 110

Pro Arg Arg Pro Gly Thr Leu Asp Gly Ser Glu Ala Gly Gly His Val
        115                 120                 125
```

```
Ser Ser Phe Val Pro Ala Cys Ser Leu Val Glu Ser His Leu Ser Asp
    130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Pro Ser Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
210                 215                 220

Lys
225

<210> SEQ ID NO 15
<211> LENGTH: 724
<212> TYPE: DNA
<213> ORGANISM: Homo sapiens
<220> FEATURE:
<221> NAME/KEY: CDS
<222> LOCATION: (47)..(724)

<400> SEQUENCE: 15
ggctcttggc tcacagccgt cccttcgctg gtgggaagaa gccgag atg gcg gca        55
                                                Met Ala Ala
                                                  1 gcc agc gct ggg gca acc cgg ctg ctc ctg ctc ttg ctg atg gcg gta      103
Ala Ser Ala Gly Ala Thr Arg Leu Leu Leu Leu Leu Leu Met Ala Val
  5                  10                  15 gca gcg ccc agt cga gcc cgg ggc agc ggc tgc cgg gcc ggg act ggt      151
Ala Ala Pro Ser Arg Ala Arg Gly Ser Gly Cys Arg Ala Gly Thr Gly
 20                  25                  30                  35 gcg cga ggg gct ggg gcg gaa ggt cga gag ggc gag gcc tgt ggc acg      199
Ala Arg Gly Ala Gly Ala Glu Gly Arg Glu Gly Glu Ala Cys Gly Thr
                 40                  45                  50 gtg ggg ctg ctg ctg gag cac tca ttt gag atc gat gac agt gcc aac      247
Val Gly Leu Leu Leu Glu His Ser Phe Glu Ile Asp Asp Ser Ala Asn
             55                  60                  65 ttc cgg aag cgg ggc tca ctg ctc tgg aac cag cag gat ggt acc ttg      295
Phe Arg Lys Arg Gly Ser Leu Leu Trp Asn Gln Gln Asp Gly Thr Leu
         70                  75                  80 tcc ctg tca cag cgg cag ctc agc gag gag gag cgg ggc cga ctc cgg      343
Ser Leu Ser Gln Arg Gln Leu Ser Glu Glu Glu Arg Gly Arg Leu Arg
 85                  90                  95 gat gtg gca gcc ctg aat ggc ctg tac cgg gtc cgg atc cca agg cga      391
Asp Val Ala Ala Leu Asn Gly Leu Tyr Arg Val Arg Ile Pro Arg Arg
100                 105                 110                 115 ccc ggg gcc ctg gat ggc ctg gaa gct ggt ggc tat gtc tcc tcc ttt      439
Pro Gly Ala Leu Asp Gly Leu Glu Ala Gly Gly Tyr Val Ser Ser Phe
                 120                 125                 130 gtc cct gcg tgc tcc ctg gtg gag tcg cac ctg tcg gac cag ctg acc      487
Val Pro Ala Cys Ser Leu Val Glu Ser His Leu Ser Asp Gln Leu Thr
             135                 140                 145 ctg cac gtg gat gtg gcc ggc aac gtg gtg ggc gtg tcg gtg gtg acg      535
Leu His Val Asp Val Ala Gly Asn Val Val Gly Val Ser Val Val Thr
         150                 155                 160 cac cct ggg ggc tgc cgg ggc cat gag gtg gag gac gtg gac ctg gag      583
His Pro Gly Gly Cys Arg Gly His Glu Val Glu Asp Val Asp Leu Glu
165                 170                 175
```

-continued

```
ctg ttc aac acc tcg gtg cag ctg cag ccg ccc acc aca gcc cca ggc      631
Leu Phe Asn Thr Ser Val Gln Leu Gln Pro Pro Thr Thr Ala Pro Gly
180             185                 190                 195 cct gag acg gcg gcc ttc att gag cgc ctg gag atg gaa cag gcc cag      679
Pro Glu Thr Ala Ala Phe Ile Glu Arg Leu Glu Met Glu Gln Ala Gln
                200                 205                 210 aag gcc aag aac ccc cag gag cag aag tcc ttc ttc gcc aaa tga          724
Lys Ala Lys Asn Pro Gln Glu Gln Lys Ser Phe Phe Ala Lys
            215                 220                 225

<210> SEQ ID NO 16
<211> LENGTH: 715
<212> TYPE: DNA
<213> ORGANISM: Mus musculus
<220> FEATURE:
<221> NAME/KEY: CDS
<222> LOCATION: (38)..(715)

<400> SEQUENCE: 16
gggctgtatg gctctcggtt tttctcaacg ctcccgt atg gtg gcc gcg ggt gcc     55
                                         Met Val Ala Ala Gly Ala
                                         1               5 ggg gtg acc cgg ctg cta gtg ctc ttg ctg atg gta gcg gct cct          103
Gly Val Thr Arg Leu Leu Val Leu Leu Leu Met Val Ala Ala Ala Pro
        10                  15                  20 agc aga gcc cga ggc agc ggc tgc cgg gtc ggg gcc tcc gcg cgt ggg      151
Ser Arg Ala Arg Gly Ser Gly Cys Arg Val Gly Ala Ser Ala Arg Gly
            25                  30                  35 acc ggg gcc gat ggc cgt gaa gct gag ggc tgt ggc acc gtg gct ttg      199
Thr Gly Ala Asp Gly Arg Glu Ala Glu Gly Cys Gly Thr Val Ala Leu
        40                  45                  50 ctg ctg gag cat tca ttt gag ctc ggt gat gga gcc aac ttc cag aag      247
Leu Leu Glu His Ser Phe Glu Leu Gly Asp Gly Ala Asn Phe Gln Lys
55                  60                  65                  70 cga ggc ttg ctg ctc tgg aac cag cag gat ggc acc ctg tcg gca aca      295
Arg Gly Leu Leu Leu Trp Asn Gln Gln Asp Gly Thr Leu Ser Ala Thr
                75                  80                  85 cag cga cag ctc agt gag gag gag cgt ggc cga ctc cgg gat gtg gct      343
Gln Arg Gln Leu Ser Glu Glu Glu Arg Gly Arg Leu Arg Asp Val Ala
            90                  95                  100 gct gtc aat ggc ctc tac agg gtc cgg gtc ccg agg cgg cct ggg aca      391
Ala Val Asn Gly Leu Tyr Arg Val Arg Val Pro Arg Arg Pro Gly Thr
        105                 110                 115 ctt gat ggt tca gaa gct ggc ggc cat gtg tct tcc ttc gtc cca gcg      439
Leu Asp Gly Ser Glu Ala Gly Gly His Val Ser Ser Phe Val Pro Ala
120                 125                 130 tgc tcc ctg gtg gag tcg cac ctt tcg gac cag ctg acc ttg cac gtg      487
Cys Ser Leu Val Glu Ser His Leu Ser Asp Gln Leu Thr Leu His Val
135                 140                 145                 150 gat gtg gct ggc aac gtg gtg ggc ctg tct gtg gtg tac cct ggg          535
Asp Val Ala Gly Asn Val Val Gly Leu Ser Val Val Val Tyr Pro Gly
                155                 160                 165 ggc tgc cgg ggc tcc gag gtg gaa gat gag gac ctg gag ctg ttc aat      583
Gly Cys Arg Gly Ser Glu Val Glu Asp Glu Asp Leu Glu Leu Phe Asn
            170                 175                 180 aca tct gtg cag ctg cgg cct ccc agc act gct cca ggc ccc gag act      631
Thr Ser Val Gln Leu Arg Pro Pro Ser Thr Ala Pro Gly Pro Glu Thr
        185                 190                 195 gca gcc ttc att gag cgc ctg gag atg gag cag gcc cag aag gcc aag      679
Ala Ala Phe Ile Glu Arg Leu Glu Met Glu Gln Ala Gln Lys Ala Lys
200                 205                 210
```

```
      aac cca cag gag cag aag tct ttc ttt gcc aaa tga              715
      Asn Pro Gln Glu Gln Lys Ser Phe Phe Ala Lys
      215                 220                 225
```

<210> SEQ ID NO 17
<211> LENGTH: 221
<212> TYPE: PRT
<213> ORGANISM: Homo sapiens

<400> SEQUENCE: 17

```
Met Ala Ala Ala Ser Gly Ala Thr Arg Leu Leu Leu Leu Leu
1               5                   10                  15

Met Ala Val Ala Ala Pro Ser Arg Ala Arg Gly Ser Gly Cys Arg Ala
                20                  25                  30

Gly Thr Gly Ala Arg Gly Ala Gly Glu Gly Arg Glu Gly Glu Ala
            35                  40                  45

Cys Gly Thr Val Gly Leu Leu Leu Glu His Ser Phe Glu Ile Asp Asp
50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95

Arg Leu Arg Asp Val Ala Ala Leu Asn Gly Leu Tyr Arg Val Arg Ile
            100                 105                 110

Pro Arg Arg Pro Gly Ala Leu Asp Gly Leu Glu Ala Gly Gly Tyr Val
        115                 120                 125

Ser Ser Phe Val Pro Ala Cys Ser Leu Val Glu Ser His Leu Ser Asp
    130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser
    210                 215                 220
```

<210> SEQ ID NO 18
<211> LENGTH: 221
<212> TYPE: PRT
<213> ORGANISM: Mus musculus

<400> SEQUENCE: 18

```
Met Val Ala Ala Gly Ala Gly Val Thr Arg Leu Leu Val Leu Leu Leu
1               5                   10                  15

Met Val Ala Ala Ala Pro Ser Arg Ala Arg Gly Ser Gly Cys Arg Val
                20                  25                  30

Gly Ala Ser Ala Arg Gly Thr Gly Ala Asp Gly Arg Glu Ala Glu Gly
            35                  40                  45

Cys Gly Thr Val Ala Leu Leu Leu Glu His Ser Phe Glu Leu Gly Asp
50                  55                  60

Gly Ala Asn Phe Gln Lys Arg Gly Leu Leu Leu Trp Asn Gln Gln Asp
65                  70                  75                  80

Gly Thr Leu Ser Ala Thr Gln Arg Gln Leu Ser Glu Glu Glu Arg Gly
```

```
                            85                  90                  95
Arg Leu Arg Asp Val Ala Ala Val Asn Gly Leu Tyr Arg Val Arg Val
            100                 105                 110

Pro Arg Arg Pro Gly Thr Leu Asp Gly Ser Glu Ala Gly Gly His Val
            115                 120                 125

Ser Ser Phe Val Pro Ala Cys Ser Leu Val Glu Ser His Leu Ser Asp
            130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Pro Ser Thr
            180                 185                 190

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser
            210                 215                 220

<210> SEQ ID NO 19
<211> LENGTH: 712
<212> TYPE: DNA
<213> ORGANISM: Homo sapiens
<220> FEATURE:
<221> NAME/KEY: CDS
<222> LOCATION: (47)..(712)

<400> SEQUENCE: 19
ggctcttggc tcacagccgt cccttcgctg gtgggaagaa gccgag atg gcg gca              55
                                                   Met Ala Ala
                                                     1 gcc agc gct ggg gca acc cgg ctg ctc ctg ctc ttg ctg atg gcg gta           103
Ala Ser Ala Gly Ala Thr Arg Leu Leu Leu Leu Leu Leu Met Ala Val
  5                  10                  15 gca gcg ccc agt cga gcc cgg ggc agc ggc tgc cgg gcc ggg act ggt           151
Ala Ala Pro Ser Arg Ala Arg Gly Ser Gly Cys Arg Ala Gly Thr Gly
20                  25                  30                  35 gcg cga ggg gct ggg gcg gaa ggt cga gag ggc gag gcc tgt ggc acg           199
Ala Arg Gly Ala Gly Ala Glu Gly Arg Glu Gly Glu Ala Cys Gly Thr
                40                  45                  50 gtg ggg ctg ctg ctg gag cac tca ttt gag atc gat gac agt gcc aac           247
Val Gly Leu Leu Leu Glu His Ser Phe Glu Ile Asp Asp Ser Ala Asn
            55                  60                  65 ttc cgg aag cgg ggc tca ctg ctc tgg aac cag cag gat ggt acc ttg           295
Phe Arg Lys Arg Gly Ser Leu Leu Trp Asn Gln Gln Asp Gly Thr Leu
        70                  75                  80 tcc ctg tca cag cgg cag ctc agc gag gag gag cgg ggc cga ctc cgg           343
Ser Leu Ser Gln Arg Gln Leu Ser Glu Glu Glu Arg Gly Arg Leu Arg
    85                  90                  95 gat gtg gca gcc ctg aat ggc ctg tac cgg gtc cgg atc cca agg cga           391
Asp Val Ala Ala Leu Asn Gly Leu Tyr Arg Val Arg Ile Pro Arg Arg
100                 105                 110                 115 ccc ggg gcc ctg gat ggc ctg gaa gct ggt ggc tat gtc tcc tcc ttt           439
Pro Gly Ala Leu Asp Gly Leu Glu Ala Gly Gly Tyr Val Ser Ser Phe
                120                 125                 130 gtc cct gcg tgc tcc ctg gtg gag tcg cac ctg tcg gac cag ctg acc           487
Val Pro Ala Cys Ser Leu Val Glu Ser His Leu Ser Asp Gln Leu Thr
            135                 140                 145 ctg cac gtg gat gtg gcc ggc aac gtg gtg ggc gtg tcg gtg gtg acg           535
Leu His Val Asp Val Ala Gly Asn Val Val Gly Val Ser Val Val Thr
```

-continued

```
                150                 155                 160
cac cct ggg ggc tgc cgg ggc cat gag gtg gag gac gtg gac ctg gag      583
His Pro Gly Gly Cys Arg Gly His Glu Val Glu Asp Val Asp Leu Glu
        165                 170                 175 ctg ttc aac acc tcg gtg cag ctg cag ccg ccc acc aca gcc cca ggc      631
Leu Phe Asn Thr Ser Val Gln Leu Gln Pro Pro Thr Thr Ala Pro Gly
180                 185                 190                 195 cct gag acg gcg gcc ttc att gag cgc ctg gag atg gaa cag gcc cag      679
Pro Glu Thr Ala Ala Phe Ile Glu Arg Leu Glu Met Glu Gln Ala Gln
                200                 205                 210 aag gcc aag aac ccc cag gag cag aag tcc tga                          712
Lys Ala Lys Asn Pro Gln Glu Gln Lys Ser
            215                 220

<210> SEQ ID NO 20
<211> LENGTH: 703
<212> TYPE: DNA
<213> ORGANISM: Mus musculus
<220> FEATURE:
<221> NAME/KEY: CDS
<222> LOCATION: (38)..(703)

<400> SEQUENCE: 20
gggctgtatg gctctcggtt tttctcaacg ctcccgt atg gtg gcc gcg ggt gcc      55
                                        Met Val Ala Ala Gly Ala
                                          1               5 ggg gtg acc cgg ctg cta gtg ctc ttg ctg atg gta gcc gcg gct cct      103
Gly Val Thr Arg Leu Leu Val Leu Leu Leu Met Val Ala Ala Ala Pro
             10                  15                  20 agc aga gcc cga ggc agc ggc tgc cgg gtc ggg gcc tcc gcg cgt ggg      151
Ser Arg Ala Arg Gly Ser Gly Cys Arg Val Gly Ala Ser Ala Arg Gly
         25                  30                  35 acc ggg gcc gat ggc cgt gaa gct gag ggc tgt ggc acc gtg gct ttg      199
Thr Gly Ala Asp Gly Arg Glu Ala Glu Gly Cys Gly Thr Val Ala Leu
     40                  45                  50 ctg ctg gag cat tca ttt gag ctc ggt gat gga gcc aac ttc cag aag      247
Leu Leu Glu His Ser Phe Glu Leu Gly Asp Gly Ala Asn Phe Gln Lys
55                  60                  65                  70 cga ggc ttg ctg ctc tgg aac cag cag gat ggc acc ctg tcg gca aca      295
Arg Gly Leu Leu Leu Trp Asn Gln Gln Asp Gly Thr Leu Ser Ala Thr
                 75                  80                  85 cag cga cag ctc agt gag gag gag cgt ggc cga ctc cgg gat gtg gct      343
Gln Arg Gln Leu Ser Glu Glu Glu Arg Gly Arg Leu Arg Asp Val Ala
             90                  95                 100 gct gtc aat ggc ctc tac agg gtc cgg gtc ccg agg cgg cct ggg aca      391
Ala Val Asn Gly Leu Tyr Arg Val Arg Val Pro Arg Arg Pro Gly Thr
         105                 110                 115 ctt gat ggt tca gaa gct ggc ggc cat gtg tct tcc ttc gtc cca gcg      439
Leu Asp Gly Ser Glu Ala Gly Gly His Val Ser Ser Phe Val Pro Ala
     120                 125                 130 tgc tcc ctg gtg gag tcg cac ctt tcg gac cag ctg acc ttg cac gtg      487
Cys Ser Leu Val Glu Ser His Leu Ser Asp Gln Leu Thr Leu His Val
135                 140                 145                 150 gat gtg gct ggc aac gtg gtg ggc ctg tct gtg gtg tac cct ggg          535
Asp Val Ala Gly Asn Val Val Gly Leu Ser Val Val Tyr Pro Gly
                155                 160                 165 ggc tgc cgg ggc tcc gag gtg gaa gat gag gac ctg gag ctg ttc aat      583
Gly Cys Arg Gly Ser Glu Val Glu Asp Glu Asp Leu Glu Leu Phe Asn
             170                 175                 180 aca tct gtg cag ctg cgg cct ccc agc act gct cca ggc ccc gag act      631
Thr Ser Val Gln Leu Arg Pro Pro Ser Thr Ala Pro Gly Pro Glu Thr
         185                 190                 195
```

```
                185                 190                 195
gca gcc ttc att gag cgc ctg gag atg gag cag gcc cag aag gcc aag      679
Ala Ala Phe Ile Glu Arg Leu Glu Met Glu Gln Ala Gln Lys Ala Lys
    200                 205                 210 aac cca cag gag cag aag tct tga                                      703
Asn Pro Gln Glu Gln Lys Ser
215                 220

<210> SEQ ID NO 21
<211> LENGTH: 227
<212> TYPE: PRT
<213> ORGANISM: Homo sapiens

<400> SEQUENCE: 21

Ser Gly Cys Arg Ala Gly Thr Gly Ala Arg Gly Ala Gly Ala Glu Gly
1               5                   10                  15

Arg Glu Gly Glu Ala Cys Gly Thr Val Gly Leu Leu Leu Glu His Ser
            20                  25                  30

Phe Glu Ile Asp Asp Ser Ala Asn Phe Arg Lys Arg Gly Ser Leu Leu
        35                  40                  45

Trp Asn Gln Gln Asp Gly Thr Leu Ser Leu Ser Gln Arg Gln Leu Ser
    50                  55                  60

Glu Glu Glu Arg Gly Arg Leu Arg Asp Val Ala Ala Leu Asn Gly Leu
65                  70                  75                  80

Tyr Arg Val Arg Ile Pro Arg Arg Pro Gly Ala Leu Asp Gly Leu Glu
                85                  90                  95

Ala Gly Gly Tyr Val Ser Ser Phe Val Pro Ala Cys Ser Leu Val Glu
            100                 105                 110

Ser His Leu Ser Asp Gln Leu Thr Leu His Val Asp Val Ala Gly Asn
        115                 120                 125

Val Val Gly Val Ser Val Val Thr His Pro Gly Gly Cys Arg Gly His
    130                 135                 140

Glu Val Glu Asp Val Asp Leu Glu Leu Phe Asn Thr Ser Val Gln Leu
145                 150                 155                 160

Gln Pro Pro Thr Thr Ala Pro Gly Pro Glu Thr Ala Ala Phe Ile Glu
                165                 170                 175

Arg Leu Glu Met Glu Gln Ala Gln Lys Ala Lys Asn Pro Gln Glu Gln
            180                 185                 190

Lys Ser Phe Phe Ala Lys Tyr Trp His Ile Ile Leu Gly Gly Ala Val
        195                 200                 205

Leu Leu Thr Ala Leu Arg Pro Ala Ala Pro Gly Pro Ala Pro Pro Pro
    210                 215                 220

Gln Glu Ala
225

<210> SEQ ID NO 22
<211> LENGTH: 227
<212> TYPE: PRT
<213> ORGANISM: Mus musculus

<400> SEQUENCE: 22

Ser Gly Cys Arg Val Gly Ala Ser Ala Arg Gly Thr Gly Ala Asp Gly
1               5                   10                  15

Arg Glu Ala Glu Gly Cys Gly Thr Val Ala Leu Leu Leu Glu His Ser
            20                  25                  30

Phe Glu Leu Gly Asp Gly Ala Asn Phe Gln Lys Arg Gly Leu Leu Leu
        35                  40                  45
```

```
Trp Asn Gln Gln Asp Gly Thr Leu Ser Ala Thr Gln Arg Gln Leu Ser
     50                  55                  60

Glu Glu Glu Arg Gly Arg Leu Arg Asp Val Ala Ala Val Asn Gly Leu
 65                  70                  75                  80

Tyr Arg Val Arg Val Pro Arg Arg Pro Gly Thr Leu Asp Gly Ser Glu
                 85                  90                  95

Ala Gly Gly His Val Ser Ser Phe Val Pro Ala Cys Ser Leu Val Glu
             100                 105                 110

Ser His Leu Ser Asp Gln Leu Thr Leu His Val Asp Val Ala Gly Asn
         115                 120                 125

Val Val Gly Leu Ser Val Val Tyr Pro Gly Gly Cys Arg Gly Ser
    130                 135                 140

Glu Val Glu Asp Glu Asp Leu Glu Leu Phe Asn Thr Ser Val Gln Leu
145                 150                 155                 160

Arg Pro Pro Ser Thr Ala Pro Gly Pro Glu Thr Ala Ala Phe Ile Glu
                165                 170                 175

Arg Leu Glu Met Glu Gln Ala Gln Lys Ala Lys Asn Pro Gln Glu Gln
            180                 185                 190

Lys Ser Phe Phe Ala Lys Tyr Trp His Leu Ile Leu Gly Gly Ala Val
        195                 200                 205

Leu Leu Thr Ala Leu Arg Pro Ala Ala Pro Gly Pro Ala Pro Ala Pro
    210                 215                 220

Thr Glu Ala
225

<210> SEQ ID NO 23
<211> LENGTH: 235
<212> TYPE: PRT
<213> ORGANISM: Homo sapiens

<400> SEQUENCE: 23

Ser Gly Cys Arg Ala Gly Thr Gly Ala Arg Gly Ala Gly Ala Glu Gly
1               5                  10                  15

Arg Glu Gly Glu Ala Cys Gly Thr Val Gly Leu Leu Leu Glu His Ser
             20                  25                  30

Phe Glu Ile Asp Asp Ser Ala Asn Phe Arg Lys Arg Gly Ser Leu Leu
         35                  40                  45

Trp Asn Gln Gln Asp Gly Thr Leu Ser Leu Ser Gln Arg Gln Leu Ser
     50                  55                  60

Glu Glu Glu Arg Gly Arg Leu Arg Asp Val Ala Ala Leu Asn Gly Leu
 65                  70                  75                  80

Tyr Arg Val Arg Ile Pro Arg Arg Pro Gly Ala Leu Asp Gly Leu Glu
                 85                  90                  95

Ala Gly Gly Tyr Val Ser Ser Phe Val Pro Ala Cys Ser Leu Val Glu
             100                 105                 110

Ser His Leu Ser Asp Gln Leu Thr Leu His Val Asp Val Ala Gly Asn
         115                 120                 125

Val Val Gly Val Ser Val Thr His Pro Gly Gly Cys Arg Gly His
    130                 135                 140

Glu Val Glu Asp Val Asp Leu Glu Leu Phe Asn Thr Ser Val Gln Leu
145                 150                 155                 160

Gln Pro Pro Thr Thr Ala Pro Gly Pro Glu Thr Ala Ala Phe Ile Glu
                165                 170                 175

Arg Leu Glu Met Glu Gln Ala Gln Lys Ala Lys Asn Pro Gln Glu Gln
```

```
                180               185               190
Lys Ser Phe Phe Ala Lys Tyr Trp Met Tyr Ile Ile Pro Val Val Leu
            195                 200                 205
Phe Leu Met Met Ser Gly Ala Pro Asp Ala Gly Gly Gln Gly Gly Gly
            210                 215                 220
Gly Gly Gly Gly Gly Gly Gly Ser Gly Arg
225                 230                 235

<210> SEQ ID NO 24
<211> LENGTH: 231
<212> TYPE: PRT
<213> ORGANISM: Mus musculus

<400> SEQUENCE: 24

Ser Gly Cys Arg Val Gly Ala Ser Ala Arg Gly Thr Gly Ala Asp Gly
1               5                   10                  15
Arg Glu Ala Glu Gly Cys Gly Thr Val Ala Leu Leu Leu Glu His Ser
            20                  25                  30
Phe Glu Leu Gly Asp Gly Ala Asn Phe Gln Lys Arg Gly Leu Leu Leu
            35                  40                  45
Trp Asn Gln Gln Asp Gly Thr Leu Ser Ala Thr Gln Arg Gln Leu Ser
        50                  55                  60
Glu Glu Glu Arg Gly Arg Leu Arg Asp Val Ala Ala Val Asn Gly Leu
65                  70                  75                  80
Tyr Arg Val Arg Val Pro Arg Arg Pro Gly Thr Leu Asp Gly Ser Glu
                85                  90                  95
Ala Gly Gly His Val Ser Ser Phe Val Pro Ala Cys Ser Leu Val Glu
            100                 105                 110
Ser His Leu Ser Asp Gln Leu Thr Leu His Val Asp Val Ala Gly Asn
            115                 120                 125
Val Val Gly Leu Ser Val Val Tyr Pro Gly Gly Cys Arg Gly Ser
        130                 135                 140
Glu Val Glu Asp Glu Asp Leu Glu Leu Phe Asn Thr Ser Val Gln Leu
145                 150                 155                 160
Arg Pro Pro Ser Thr Ala Pro Gly Pro Glu Thr Ala Ala Phe Ile Glu
                165                 170                 175
Arg Leu Glu Met Glu Gln Ala Gln Lys Ala Lys Asn Pro Gln Glu Gln
            180                 185                 190
Lys Ser Phe Phe Ala Lys Tyr Trp Met Tyr Ile Ile Pro Val Val Leu
            195                 200                 205
Phe Leu Met Met Ser Gly Ala Pro Asp Ala Gly Gly Gln Gly Gly Gly
            210                 215                 220
Gly Gly Gly Gly Ser Ser Arg
225                 230

<210> SEQ ID NO 25
<211> LENGTH: 200
<212> TYPE: PRT
<213> ORGANISM: Homo sapiens

<400> SEQUENCE: 25

Ser Gly Cys Arg Ala Gly Thr Gly Ala Arg Gly Ala Gly Ala Glu Gly
1               5                   10                  15
Arg Glu Gly Glu Ala Cys Gly Thr Val Gly Leu Leu Leu Glu His Ser
            20                  25                  30
Phe Glu Ile Asp Asp Ser Ala Asn Phe Arg Lys Arg Gly Ser Leu Leu
```

```
                35                  40                  45
Trp Asn Gln Gln Asp Gly Thr Leu Ser Leu Ser Gln Arg Gln Leu Ser
         50                  55                  60
Glu Glu Glu Arg Gly Arg Leu Arg Asp Val Ala Ala Leu Asn Gly Leu
 65                  70                  75                  80
Tyr Arg Val Arg Ile Pro Arg Arg Pro Gly Ala Leu Asp Gly Leu Glu
                 85                  90                  95
Ala Gly Gly Tyr Val Ser Ser Phe Val Pro Ala Cys Ser Leu Val Glu
            100                 105                 110
Ser His Leu Ser Asp Gln Leu Thr Leu His Val Asp Val Ala Gly Asn
            115                 120                 125
Val Val Gly Val Ser Val Val Thr His Pro Gly Gly Cys Arg Gly His
        130                 135                 140
Glu Val Glu Asp Val Asp Leu Glu Leu Phe Asn Thr Ser Val Gln Leu
145                 150                 155                 160
Gln Pro Pro Thr Thr Ala Pro Gly Pro Glu Thr Ala Ala Phe Ile Glu
                165                 170                 175
Arg Leu Glu Met Glu Gln Ala Gln Lys Ala Lys Asn Pro Gln Glu Gln
            180                 185                 190
Lys Ser Phe Phe Ala Lys Tyr Trp
        195                 200

<210> SEQ ID NO 26
<211> LENGTH: 200
<212> TYPE: PRT
<213> ORGANISM: Mus musculus

<400> SEQUENCE: 26

Ser Gly Cys Arg Val Gly Ala Ser Ala Arg Gly Thr Gly Ala Asp Gly
 1               5                  10                  15
Arg Glu Ala Glu Gly Cys Gly Thr Val Ala Leu Leu Leu Glu His Ser
             20                  25                  30
Phe Glu Leu Gly Asp Gly Ala Asn Phe Gln Lys Arg Gly Leu Leu Leu
         35                  40                  45
Trp Asn Gln Gln Asp Gly Thr Leu Ser Ala Thr Gln Arg Gln Leu Ser
     50                  55                  60
Glu Glu Glu Arg Gly Arg Leu Arg Asp Val Ala Ala Val Asn Gly Leu
 65                  70                  75                  80
Tyr Arg Val Arg Val Pro Arg Arg Pro Gly Thr Leu Asp Gly Ser Glu
                 85                  90                  95
Ala Gly Gly His Val Ser Ser Phe Val Pro Ala Cys Ser Leu Val Glu
            100                 105                 110
Ser His Leu Ser Asp Gln Leu Thr Leu His Val Asp Val Ala Gly Asn
            115                 120                 125
Val Val Gly Leu Ser Val Val Val Tyr Pro Gly Gly Cys Arg Gly Ser
        130                 135                 140
Glu Val Glu Asp Glu Asp Leu Glu Leu Phe Asn Thr Ser Val Gln Leu
145                 150                 155                 160
Arg Pro Pro Ser Thr Ala Pro Gly Pro Glu Thr Ala Ala Phe Ile Glu
                165                 170                 175
Arg Leu Glu Met Glu Gln Ala Gln Lys Ala Lys Asn Pro Gln Glu Gln
            180                 185                 190
Lys Ser Phe Phe Ala Lys Tyr Trp
        195                 200
```

```
<210> SEQ ID NO 27
<211> LENGTH: 198
<212> TYPE: PRT
<213> ORGANISM: Homo sapiens

<400> SEQUENCE: 27

Ser Gly Cys Arg Ala Gly Thr Gly Ala Arg Gly Ala Gly Ala Glu Gly
  1               5                  10                  15

Arg Glu Gly Glu Ala Cys Gly Thr Val Gly Leu Leu Leu Glu His Ser
             20                  25                  30

Phe Glu Ile Asp Asp Ser Ala Asn Phe Arg Lys Arg Gly Ser Leu Leu
         35                  40                  45

Trp Asn Gln Gln Asp Gly Thr Leu Ser Leu Ser Gln Arg Gln Leu Ser
     50                  55                  60

Glu Glu Glu Arg Gly Arg Leu Arg Asp Val Ala Ala Leu Asn Gly Leu
 65                  70                  75                  80

Tyr Arg Val Arg Ile Pro Arg Arg Pro Gly Ala Leu Asp Gly Leu Glu
                 85                  90                  95

Ala Gly Gly Tyr Val Ser Ser Phe Val Pro Ala Cys Ser Leu Val Glu
            100                 105                 110

Ser His Leu Ser Asp Gln Leu Thr Leu His Val Asp Val Ala Gly Asn
        115                 120                 125

Val Val Gly Val Ser Val Val Thr His Pro Gly Gly Cys Arg Gly His
    130                 135                 140

Glu Val Glu Asp Val Asp Leu Glu Leu Phe Asn Thr Ser Val Gln Leu
145                 150                 155                 160

Gln Pro Pro Thr Thr Ala Pro Gly Pro Glu Thr Ala Ala Phe Ile Glu
                165                 170                 175

Arg Leu Glu Met Glu Gln Ala Gln Lys Ala Lys Asn Pro Gln Glu Gln
            180                 185                 190

Lys Ser Phe Phe Ala Lys
            195

<210> SEQ ID NO 28
<211> LENGTH: 198
<212> TYPE: PRT
<213> ORGANISM: Mus musculus

<400> SEQUENCE: 28

Ser Gly Cys Arg Val Gly Ala Ser Ala Arg Gly Thr Gly Ala Asp Gly
  1               5                  10                  15

Arg Glu Ala Glu Gly Cys Gly Thr Val Ala Leu Leu Leu Glu His Ser
             20                  25                  30

Phe Glu Leu Gly Asp Gly Ala Asn Phe Gln Lys Arg Gly Leu Leu Leu
         35                  40                  45

Trp Asn Gln Gln Asp Gly Thr Leu Ser Ala Thr Gln Arg Gln Leu Ser
     50                  55                  60

Glu Glu Glu Arg Gly Arg Leu Arg Asp Val Ala Ala Val Asn Gly Leu
 65                  70                  75                  80

Tyr Arg Val Arg Val Pro Arg Arg Pro Gly Thr Leu Asp Gly Ser Glu
                 85                  90                  95

Ala Gly Gly His Val Ser Ser Phe Val Pro Ala Cys Ser Leu Val Glu
            100                 105                 110

Ser His Leu Ser Asp Gln Leu Thr Leu His Val Asp Val Ala Gly Asn
        115                 120                 125
```

-continued

Val Val Gly Leu Ser Val Val Tyr Pro Gly Gly Cys Arg Gly Ser
    130             135             140

Glu Val Glu Asp Glu Asp Leu Glu Leu Phe Asn Thr Ser Val Gln Leu
145                 150                 155                 160

Arg Pro Pro Ser Thr Ala Pro Gly Pro Glu Thr Ala Ala Phe Ile Glu
                165                 170                 175

Arg Leu Glu Met Glu Gln Ala Gln Lys Ala Lys Asn Pro Gln Glu Gln
            180                 185                 190

Lys Ser Phe Phe Ala Lys
        195

<210> SEQ ID NO 29
<211> LENGTH: 194
<212> TYPE: PRT
<213> ORGANISM: Homo sapiens

<400> SEQUENCE: 29

Ser Gly Cys Arg Ala Gly Thr Gly Ala Arg Gly Ala Gly Ala Glu Gly
1               5                   10                  15

Arg Glu Gly Glu Ala Cys Gly Thr Val Gly Leu Leu Leu Glu His Ser
                20                  25                  30

Phe Glu Ile Asp Asp Ser Ala Asn Phe Arg Lys Arg Gly Ser Leu Leu
            35                  40                  45

Trp Asn Gln Gln Asp Gly Thr Leu Ser Leu Ser Gln Arg Gln Leu Ser
    50                  55                  60

Glu Glu Glu Arg Gly Arg Leu Arg Asp Val Ala Ala Leu Asn Gly Leu
65                  70                  75                  80

Tyr Arg Val Arg Ile Pro Arg Arg Pro Gly Ala Leu Asp Gly Leu Glu
                85                  90                  95

Ala Gly Gly Tyr Val Ser Ser Phe Val Pro Ala Cys Ser Leu Val Glu
            100                 105                 110

Ser His Leu Ser Asp Gln Leu Thr Leu His Val Asp Val Ala Gly Asn
        115                 120                 125

Val Val Gly Val Ser Val Val Thr His Pro Gly Gly Cys Arg Gly His
    130             135             140

Glu Val Glu Asp Val Asp Leu Glu Leu Phe Asn Thr Ser Val Gln Leu
145                 150                 155                 160

Gln Pro Pro Thr Thr Ala Pro Gly Pro Glu Thr Ala Ala Phe Ile Glu
                165                 170                 175

Arg Leu Glu Met Glu Gln Ala Gln Lys Ala Lys Asn Pro Gln Glu Gln
            180                 185                 190

Lys Ser

<210> SEQ ID NO 30
<211> LENGTH: 194
<212> TYPE: PRT
<213> ORGANISM: Mus musculus

<400> SEQUENCE: 30

Ser Gly Cys Arg Val Gly Ala Ser Ala Arg Gly Thr Gly Ala Asp Gly
1               5                   10                  15

Arg Glu Ala Glu Gly Cys Gly Thr Val Ala Leu Leu Leu Glu His Ser
                20                  25                  30

Phe Glu Leu Gly Asp Gly Ala Asn Phe Gln Lys Arg Gly Leu Leu Leu
            35                  40                  45

Trp Asn Gln Gln Asp Gly Thr Leu Ser Ala Thr Gln Arg Gln Leu Ser

-continued

```
                50                      55                      60
Glu Glu Glu Arg Gly Arg Leu Arg Asp Val Ala Ala Val Asn Gly Leu
 65                      70                      75                      80

Tyr Arg Val Arg Val Pro Arg Arg Pro Gly Thr Leu Asp Gly Ser Glu
                 85                      90                      95

Ala Gly Gly His Val Ser Ser Phe Val Pro Ala Cys Ser Leu Val Glu
                100                     105                     110

Ser His Leu Ser Asp Gln Leu Thr Leu His Val Asp Val Ala Gly Asn
            115                     120                     125

Val Val Gly Leu Ser Val Val Val Tyr Pro Gly Gly Cys Arg Gly Ser
    130                     135                     140

Glu Val Glu Asp Glu Asp Leu Glu Leu Phe Asn Thr Ser Val Gln Leu
145                     150                     155                     160

Arg Pro Pro Ser Thr Ala Pro Gly Pro Glu Thr Ala Ala Phe Ile Glu
                165                     170                     175

Arg Leu Glu Met Glu Gln Ala Gln Lys Ala Lys Asn Pro Gln Glu Gln
                180                     185                     190

Lys Ser
```